(12) United States Patent
Platzek et al.

(10) Patent No.: US 12,258,343 B2
(45) Date of Patent: Mar. 25, 2025

(54) METHOD FOR PREPARING 2-[(3R)-3-METHYLMORPHOLIN-4-YL]-4-[1-METHYL-1H-PYRAZOL-5-YL)-8-(1H-PYRAZOL-5-YL)-1,7-NAPHTHYRIDINE

(71) Applicants: Bayer Aktiengesellschaft, Leverkusen (DE); Bayer Pharma Aktiengesellschaft, Berlin (DE)

(72) Inventors: Johannes Platzek, Berlin (DE); Philipp Rubenbauer, Bensheim (DE); Hendricus Nicolaas Sebastiaan Van Der Haas, Nijmegen (NL); Sonja Elisabeth Hoogeveen, Oss (NL); Matthijs Cornelis Maria Van Oers, Nijmegen (NL); Reinerus Gerardus Gieling, Beuningen (NL); Jeroen Alexander Dekker, Ede (NL)

(73) Assignees: BAYER AKTIENGESELLSCHAFT, Leverkusen (DE); BAYER PHARMA AKTIENGESELLSCHAFT, Berlin (DE)

( * ) Notice: Subject to any disclaimer, the term of this patent is extended or adjusted under 35 U.S.C. 154(b) by 1035 days.

(21) Appl. No.: 17/271,141

(22) PCT Filed: Aug. 22, 2019

(86) PCT No.: PCT/EP2019/072467
§ 371 (c)(1),
(2) Date: Feb. 24, 2021

(87) PCT Pub. No.: WO2020/039025
PCT Pub. Date: Feb. 27, 2020

(65) Prior Publication Data
US 2021/0253573 A1   Aug. 19, 2021

(30) Foreign Application Priority Data
Aug. 24, 2018 (EP) .................................. 18190731

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .... C07D 471/04; C07B 2200/13; Y02P 20/55
(Continued)

(56) References Cited

U.S. PATENT DOCUMENTS

2016/0287604 A1   10/2016   Wortmann et al.

FOREIGN PATENT DOCUMENTS

WO         2016020320 A1      2/2016

OTHER PUBLICATIONS

International Preliminary Report on Patentability issued in International Application No. PCT/EP2019/072467, dated Mar. 2, 2021.
(Continued)

*Primary Examiner* — Taylor V Oh
(74) *Attorney, Agent, or Firm* — James Dilmore

(57) ABSTRACT

The present invention covers a method for preparing 2-[(3R)-3-methylmorpholin-4-yl]-4-(1-methyl-1H-pyrazol-5-yl)-8-(1H-pyrazol-5-yl)-1,7-naphthyridine ("the compound of formula (I)" in the following) as well as intermediate compounds useful in the preparation of the compound of formula (I). The present invention also covers polymorphic form B of the compound of formula (I) with very high purity.

(Continued)

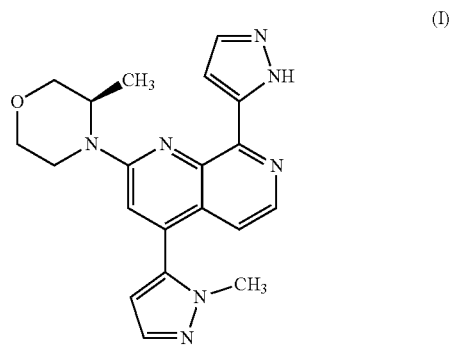

(I)

16 Claims, 1 Drawing Sheet

(58) Field of Classification Search
USPC .......................................................... 546/113
See application file for complete search history.

(56) References Cited

OTHER PUBLICATIONS

Kubasov, A. A., "Chemical kinetics and catalysis. Part 1", Moscow: Moscow University, pp. 3-4. (Year:2004).

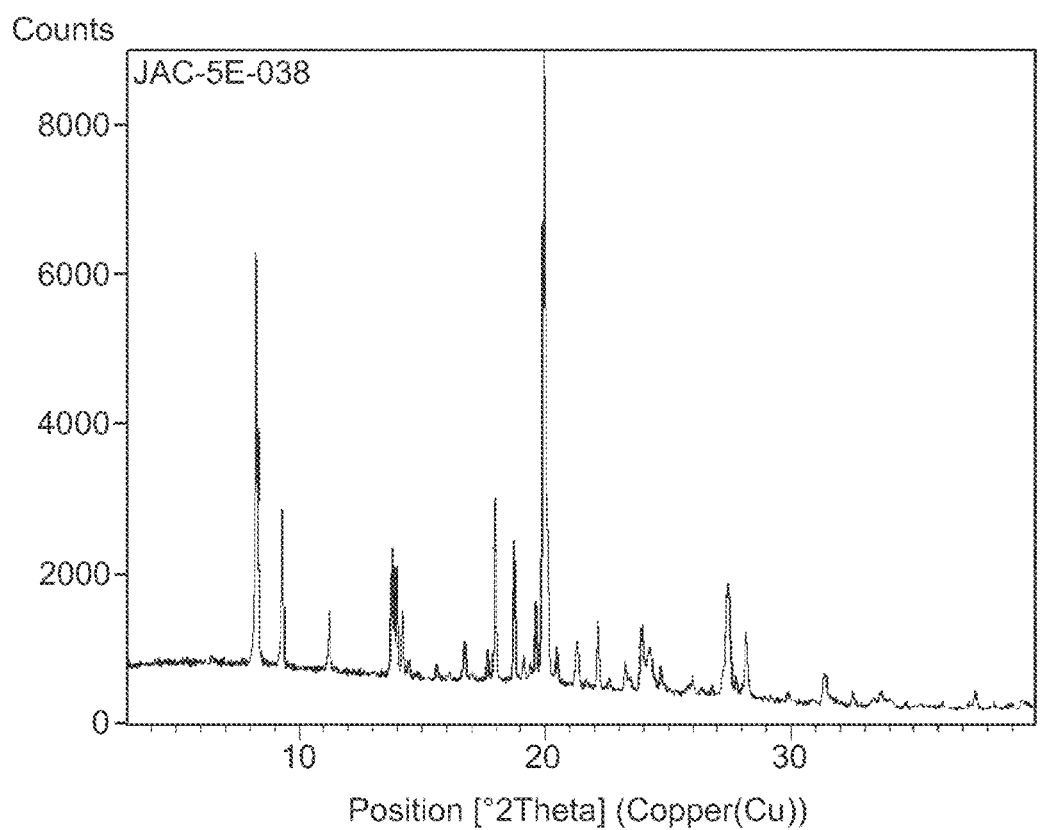

METHOD FOR PREPARING 2-[(3R)-3-METHYLMORPHOLIN-4-YL]-4-[1-METHYL-1H-PYRAZOL-5-YL)-8-(1H-PYRAZOL-5-YL)-1,7-NAPHTHYRIDINE

CROSS REFERENCE TO RELATED APPLICATIONS

This application is a national stage application under 35 U.S.C. § 371 of International Application No. PCT/EP2019/072467, filed internationally on Aug. 22, 2019, which claims priority benefit of European Application No. 18190731.2, filed Aug. 24, 2018.

The present invention covers a method for preparing 2-[(3R)-3-methylmorpholin-4-yl]-4-(1-methyl-1H-pyrazol-5-yl)-8-(1H-pyrazol-5-yl)-1,7-naphthyridine ("the compound of formula (I)" in the following) as well as intermediate compounds useful in the preparation of the compound of formula (I). The present invention also covers polymorphic form B of the compound of formula (I) with very high purity.

BACKGROUND

Example 111 of WO2016020320A1 describes a method for the synthesis of 2-[(3R)-3-methylmorpholin-4-yl]-4-(1-methyl-1H-pyrazol-5-yl)-8-(1H-pyrazol-5-yl)-1,7-naphthyridine of formula (I) by using the following synthesis route:

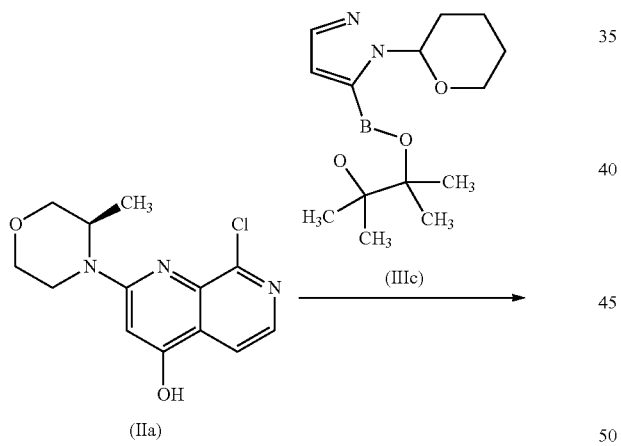

(IIa)

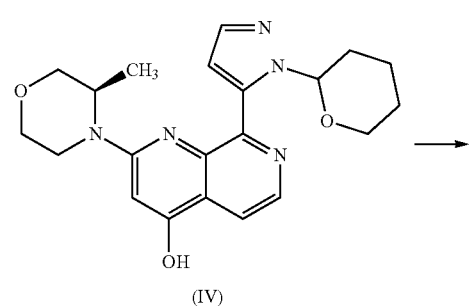

(IV)

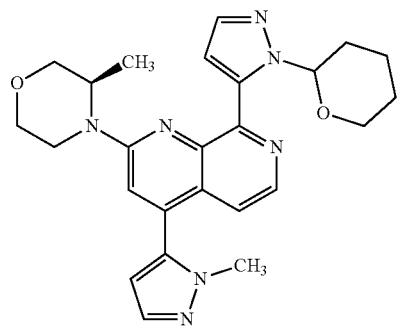

(V)

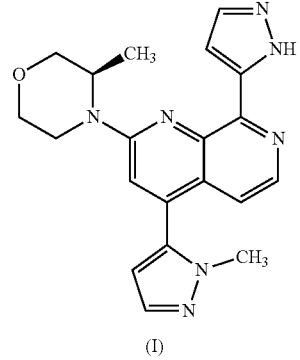

(VIIc/VIId)

(I)

The synthesis of compound (IIa) (=8-chloro-2-((R)-3-methylmorpholin-4-yl)-[1,7]naphthyridin-4-ol) is described in Example "Intermediate-7", step c of WO2016020320A1.

According to WO2016020320A1 "Intermediate-9", which corresponds to compound (IV) (=2-[((R)-3-methylmorpholin-4-yl)-8-[2-(tetrahydropyran-2-yl)-2H-pyrazol-3-yl]-[1,7]naphthyridin-4-ol), was prepared by a Suzuki coupling of the compound of formula (IIa) and the tetrahydropyranyl-protected boronic ester compound (IIIc) (=1-(tetrahydropyran-2-yl)-5-(4,4,5,5-tetramethyl-[1,3,2]dioxaborolane-2-yl)-1H-pyrazole) under argon using [1,1' bis(diphenylphosphino)ferrocene]dichloropalladium(II) complex with dichloromethane (1:1) as catalyst and cesium carbonate in absolute 1,4-dioxane. The reaction mixture was stirred at 90° C. for 16 h. The brown reaction solution was purified via column chromatography [silica gel 60; ethyl acetate]. 506 mg (72% of theory) of 2-[(R)-3-methylmorpholin-4-yl)-8-[2-(tetrahydropyran-2-yl)-2H-pyrazol-3-yl]-[1,7]naphthyridin-4-ol were isolated as a yellow oil.

For the following exemplary reasons the lab scale preparation of the compound of formula (IV), which is described in WO2016020320A1, is unsuitable for a large scale production process:

The use of absolute solvent (e.g. 1,4-dioxane) is difficult to handle on large scale.

Cesium carbonate is a relatively expensive inorganic base.

A long reaction time (16 h at 90° C.) is required.

The compound of formula (IV) is an oil, so it cannot be purified by an easy crystallization step, which is the preferred method on larger scale.

Purification via column chromatography is time consuming and expensive.

According to WO2016020320A1 "Intermediate 9", the oily compound of formula (IV), is then converted to "Intermediate 10", which corresponds to the compound of formula (V) (=2-[(3R)-3-methylmorpholin-4-yl]-8-[1-(tetrahydro-2H-pyran-2-yl)-1H-pyrazol-5-yl]-1,7-naphthyridin-4-yl trifluoromethanesulfonate) by treatment with N-phenylbis-(trifluoromethanesulfonimide) and N,N-diisopropylethylamine under argon in absolute dichloromethane. The reaction time was three days at room temperature. The solvent was distilled off under reduced pressure and the residue was chromatographed twice [silica gel 60 (400 g); dichloromethane:methanol, 98:2/ethyl acetate]. The compound of formula (V) was obtained in 2.6 g (42% of theory) as yellow solid after evaporation to dryness.

The drawbacks of this procedure are, for example:

The use of absolute solvent (expensive).

Very long reaction time (three days at room temperature), which is expensive.

Two chromatographic purification steps, which are very time consuming and expensive.

Very low yield (42%) for this step.

Isolation via evaporation of the chromatography fractions. This is not feasible for scale up because this is very energy- and cost-intensive.

The compound of formula (V) is converted to the compound of formula (VIIc/VIId) via a Suzuki reaction, using 1-methyl-5-(4,4,5,5-tetramethyl-1,3,2-dioxaborolan-2-yl)-1H-pyrazole (VIb), aq. potassium carbonate (1.4 ml, 2 M) and bis(triphenylphosphine)palladium(II) dichloride-(67 mg, 0.094 mmol), which were solubilised in dimethoxyethane (60 ml). The reaction mixture was stirred for 20 minutes at 130° C. under microwave irradiation. After cooling to room temperature, the reaction mixture was filtered through a silicon filter and concentrated under reduced pressure. The crude material was purified by flash column chromatography (hexane/ethyl acetate/ethanol mixture). The desired fractions were concentrated under reduced pressure and solubilised in conc. sulphuric acid (5 ml). The mixture was stirred for 3 h at room temperature. The mixture was then poured into ice and basified using solid sodium hydrogen carbonate. The suspension was filtered and the solid was stirred with ethanol at 40° C., filtered and dried under reduced pressure. The compound of formula (I) was obtained in 78% yield (0.28 g).

At least the following points are critical for scale up:

Using a microwave reactor on scale is not feasible. Running a large scale reaction at 130° C. for just 20 minutes is challenging and cannot be realized on a multi-kg scale.

Chromatography for isolation and purification is time consuming and expensive on scale.

Evaporation of the compound containing chromatography fractions is not feasible on larger scale, because this is very energy- and cost-intensive.

The purity of the compound of formula (I) does not meet GMP requirements.

In summary, the described process for the production of desired compound (I) starting from the compound of formula (IIa) (=8-chloro-2-((R)-3-methylmorpholin-4-yl)-[1,7]naphthyridin-4-ol) is very inefficient, time consuming and expensive as it involves three chromatographic steps and results in long reaction times and in a very low overall yield (from compound of formula (II) to (I): 23.6% theoretical yield.

It was therefore an object of the present invention to provide a method for preparing 2-[(3R)-3-methylmorpholin-4-yl]-4-(1-methyl-1H-pyrazol-5-yl)-8-(1H-pyrazol-5-yl)-1,7-naphthyridine of formula (I), which does not have one or more of the aforementioned disadvantages.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means 1, 2, 3, 4 or 5, particularly 1, 2, 3 or 4, more particularly 1, 2 or 3, even more particularly 1 or 2.

The term "comprising" when used in the specification includes "consisting of".

If within the present text any item is referred to as "as mentioned herein", it means that it may be mentioned anywhere in the present text.

The terms as mentioned in the present text have the following meanings:

The term "$C_1$-$C_6$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_1$-$C_6$", as used in the present text, e.g. in the context of the definition of "$C_1$-$C_6$-alkyl" means an alkyl group having a finite number of carbon atoms of 1 to 6, i.e. 1, 2, 3, 4, 5 or 6 carbon atoms.

When a range of values is given, said range encompasses each value and sub-range within said range.

For example: "$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$.

The compound of formula (I) may exist as a tautomer of formula (Ia)

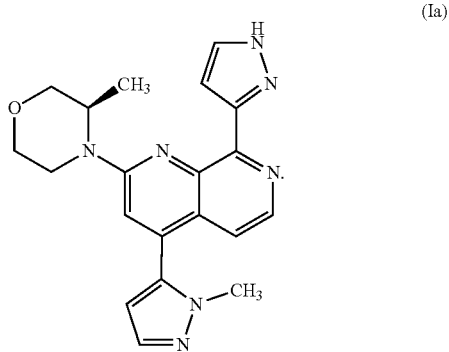 [SMILES: C[C@@H]1COCCN1c1cc(-c2ccnn2C)c2ccnc(-c3cc[nH]n3)c2n1]

(Ia)

The person skilled in the art also knows that the compounds of formula (I) and (Ia) may exist as mixtures of both tautomers (I) and (Ia).

The compounds of the present invention of formula (VIIIa) or (IXa) optionally contain more than one, particularly two, asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres.

Separated, pure or partially purified isomers and stereoisomers or racemic or diastereomeric mixtures of the compounds of the present invention are also included within the scope of the present invention. The purification and the separation of such materials can be accomplished by standard techniques known in the art. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention of formula (VIIIa) or (IXa) as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, of formula (VIIIa) or (IXa) such as hydrates, solvates, salts, in particular pharmaceutically acceptable salts, and/or co-precipitates.

Further, it is possible for the compounds of the present invention of formula (VIIIa) or (IXa) to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention of formula (VIIIa) or (IXa). For example, see S. M. Berge, et al. "Pharmaceutical Salts," J. Pharm. Sci. 1977, 66, 1-19.

A suitable pharmaceutically acceptable salt of the compounds of the present invention of formula (VIIIa) or (IXa) may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention of formula (VIIIa) or (IXa) which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methylglucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds of formula (VIIIa) or (IXa) to be prepared by reaction of the compounds with the appropriate inorganic or organic acid via any of a number of known methods. Alternatively, alkali and alkaline earth metal salts of acidic compounds of the present invention of formula (VIIIa) or (IXa) are prepared by reacting the compounds of the present invention with the appropriate base via a variety of known methods.

The present invention includes all possible salts of the compounds of the present invention of formula (VIIIa) or (IXa) as single salts, or as any mixture of said salts, in any ratio.

Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

Furthermore, the present invention includes all possible crystalline forms, or polymorphs, of the compounds of the present invention of formula (VIIIa) or (IXa), either as single polymorph, or as a mixture of more than one polymorph, in any ratio.

It is possible for the compounds of formula (VIIIa) or (IXa) to exist as isotopic variants. The invention therefore includes one or more isotopic variant(s) of the compounds of formula (VIIIa) or (IXa) particularly deuterium-containing of formula (VIIIa) or (IXa).

The term "Isotopic variant" of a compound or a reagent is defined as a compound exhibiting an unnatural proportion of one or more of the isotopes that constitute such a compound.

The term "Isotopic variant of the compound of formula (VIIIa) or (IXa)" is defined as a compound of formula (VIIIa) or of formula (IXa) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the present invention the isotopic variant(s) of the compounds of general formula (VIIIa) or (IXa) preferably contain deuterium ("deuterium-containing compounds of formula (VIIIa) or (IXa)").

Isotopic variants of the compounds of formula (VIIIa) or (IXa) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from D$_2$O can be incorporated either directly into the compounds or into reagents that are useful for synthesizing such compounds Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of formula (VIIIa) or (IXa)" is defined as a compound of formula (VIIIa) or of formula (IXa), in which one or more hydrogen atom(s) is/are replaced by one or more deuterium atom(s) and in which the abundance of deuterium at each deuterated position of the compound of formula (VIIIa) or (IXa) is higher than the natural abundance of deuterium, which is about 0.015%. Particularly, in a deuterium-containing compound of formula (VIIIa) or (IXa) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

DESCRIPTION OF THE INVENTION

The method for preparing the the compound of formula (I) according to the invention is characterized by various advantageous preparation steps and also intermediates, which can be illustrated by the following scheme:

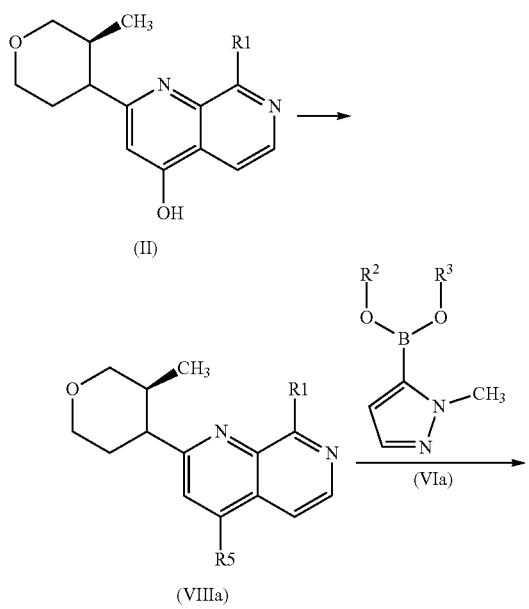

-continued

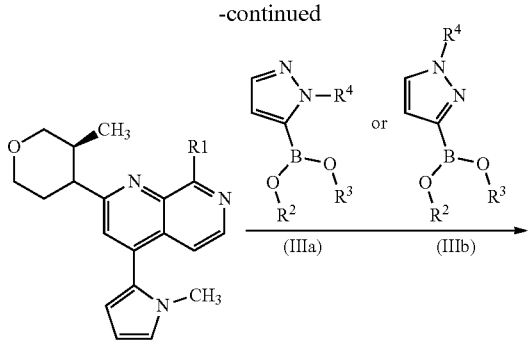

(IXa)

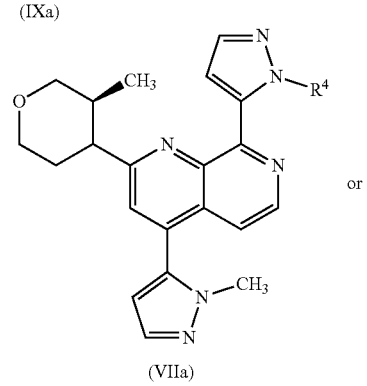

(VIIa)

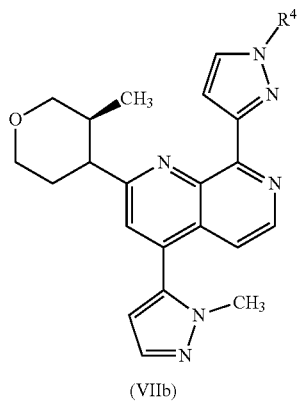

(VIIb)

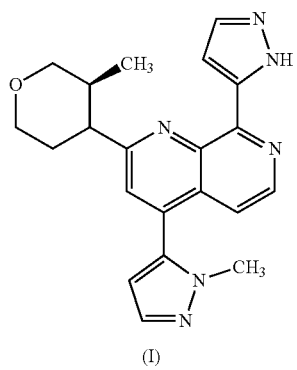

(I)

The new synthetic route from the intermediate compound (II) to the compound of formula (I) has several advantages compared to the route described in WO2016020320A1. The new route provides at least one or more of the following advantages compared to the previously described process:

No chromatographic purification step is necessary, neither for intermediates of formula (VIIIa) or (IXa) nor for the intermediate compounds of formula (VIIa) or (VIIb).

No microwave reactor is used.

The two new intermediates (VIIIa)/(VIIIb) and (IXa)/(IXb) are crystalline, can be easily isolated and purified by crystallization, in particular by using environmentally friendly solvents, such as for example isopropanol and n-butanol.

Shorter reaction times.

The overall yield is significantly increased. When taking the best yields of each step into account the overall yield is increased by a factor of about 2, resulting in about 49.0% theoretical yield of the new route compared to 23.6% theoretical yield of the route described in WO2016020320A1.

The purity of the compound of formula (I) is significantly increased, e.g.:

Residual palladium values are very low (<10 ppm)

Residual boron values are very low (<10 ppm)

Residual solvents comply with regulatory requirements.

The new process allows large scale production of the polymorphic form B of the compound of formula (I).

The process according to the invention for the preparation of compound of formula (I)/(Ia) is characterized by at least one of the following steps:

1. Synthesis of the compound of formula (I) or (Ia) via the intermediate compound of formula (VIIa) or (VIIb) starting from the intermediate compound of formula (IXa) or (IXb).

2. Synthesis of the intermediate compound of formula (IXa) or (IXb) by reacting an intermediate compound of formula (VIIIa) or (VIIIb) with a compound of formula (VIa) or (VIb).

3. Synthesis of the intermediate compound of formula (VIIIa) or (VIIIb) starting from the compound of formula (II) or (IIa).

The process according to the invention for the preparation of compound of formula (I) and its individual process steps is further characterized by new intermediates (IXa)/(IXb) (see section 4.) and (VIIIa)/(VIIIb) (see section 5.) and provides the compound of formula (I) with high purity (see section 6.).

1. Synthesis of the Compound of Formula (I) or (Ia) Via the Intermediate Compound of Formula (VIIa) or (VIIb) Starting from the Intermediate Compound of Formula (IXa) or (IXb)

In accordance with one aspect, the present invention relates to a method for preparing the compound of formula (I)

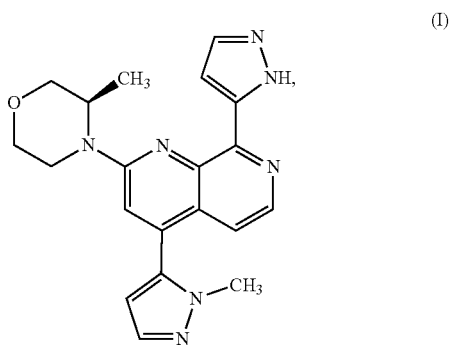 [SMILES: C[C@@H]1COCCN1c1cc(-c2ccnn2C)c2ccnc(-c3ccn[nH]3)c2n1]

(I)

or its tautomer of formula (Ia)

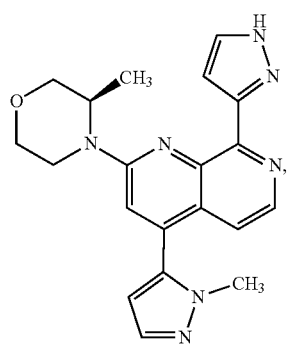
(Ia)

or a mixture thereof, said method comprising the successive steps of:

(a) reacting an intermediate compound of formula (IXa)

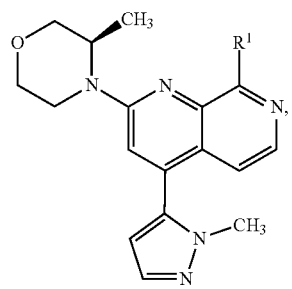
(IXa)

in which $R^1$ represents a chlorine, bromine or iodine atom or represents a group selected from [(trifluoromethyl) sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl] oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl) sulfonyl]oxy and [(4-methoxyphenyl)sulfonyl]oxy;

with a compound of formula (IIIa) or (IIIb)

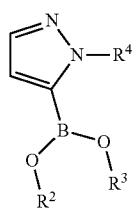
(IIIa)

or

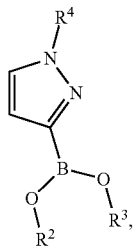
(IIIb)

or a mixture thereof, in which $R^2$ and $R^3$ represent, independently from each other, a hydrogen atom or a $C_1$-$C_6$-alkyl group;

or $R^2$ and $R^3$ together represent a —$CH_2$—$CH_2$— group or a —$CH_2$—$CH_2$—$CH_2$— group, wherein said —$CH_2$—$CH_2$— group or —$CH_2$—$CH_2$—$CH_2$— group is optionally substituted one, two, three or four times with a group selected from methyl and ethyl;

or $R^2$ and $R^3$ together represent a group

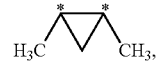

wherein "*" represents the point of attachment to the rest of the molecule;

and $R^4$ represents a group selected from tetrahydro-2H-pyran-2-yl, 1-methyl-1-methoxyethyl, 1-methyl-1-phenoxyethyl, 1-methyl-1-benzyloxyethyl;

to give an intermediate compound of formula (VIIa) or (VIIb)

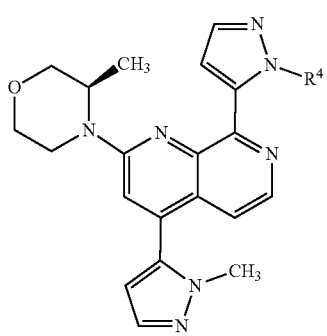
(VIIa)

or

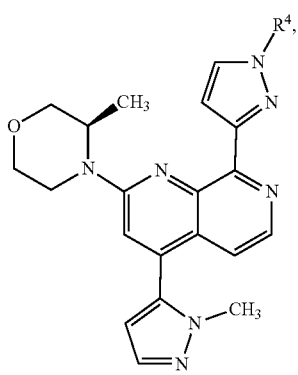

(VIIb)

or a mixture thereof,
in which
R⁴ represents a group selected from tetrahydro-2H-pyran-2-yl, 1-methyl-1-methoxyethyl, 1-methyl-1-phenoxyethyl, 1-methyl-1-benzyloxyethyl; and (b) removing the group R⁴ from the intermediate compound of formula (VIIa) or (VIIb), thus providing a compound of formula (I), or its tautomer of formula (Ia), or a mixture thereof.

In another embodiment of the method according to the present invention R¹ of the compound of formula (IXa) represents a chlorine or bromine atom, preferably a chlorine atom.

The compound of formula (IXa), in which R¹ represents a chlorine atom is the preferred compound of formula (IXb):

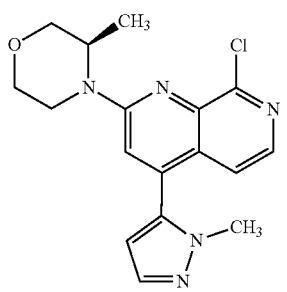

(IXb)

In another embodiment of the method according to the present invention, R¹ of the compound of formula (IXa) represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment of the method according to the present invention, R¹ of the compound of formula (IXa) represents a group selected from [(trifluoromethyl)sulfonyl]oxy, [(nonafluorobutyl)sulfonyl]oxy, (methylsulfonyl)oxy and (p-toluenesulfonyl)oxy.

In another embodiment of the present invention, R² and R³ of the compound of formula (IIIa) or (IIIb) represent, independently from each other, a hydrogen atom or a C₁-C₃ alkyl group, particularly a methyl or ethyl group.

In another embodiment of the present invention, R² and R³ of the compound of formula (IIIa) or (IIIb) together represent a —CH₂—CH₂— group or a —CH₂—CH₂—CH₂— group, wherein said —CH₂—CH₂— group or —CH₂—CH₂—CH₂— group is optionally substituted one, two, three or four times with a group selected from methyl and ethyl.

If R² and R³ of the compound of formula (IIIa) or (IIIb) together represent a —CH₂—CH₂— group or a —CH₂—CH₂—CH₂— group, said —CH₂—CH₂— group or said —CH₂—CH₂—CH₂— group together with the boron atom and the oxygen atoms to which said group is bound forms a 5- or 6-membered ring.

In another embodiment of the present invention, R² and R³ of the compound of formula (IIIa) or (IIIb) together represent a group

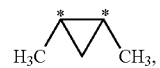

wherein "*" represents the point of attachment to the rest of the molecule.

In another embodiment of the present invention, R² and R³ of the compound of formula (IIIa) or (IIIb) together represent a —C(CH₃)₂—C(CH₃)₂— or a —CH₂—C(CH₃)₂—CH₂— group.

In a preferred embodiment of the present invention, R² and R³ of the compound of formula (IIIa) or (IIIb) together represent a —C(CH₃)₂—C(CH₃)₂— group.

In a preferred embodiment of the present invention, the compound of formula (IIIa) is 1-(tetrahydro-2H-pyran-2-yl)-1H-pyrazole-5-boronic acid pinacol ester (of formula IIIc):

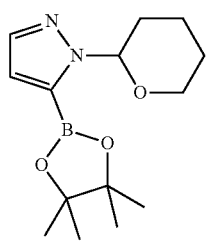

(IIIc)

The compounds of formula (IIIa), (IIIb) or (IIIc) are commercially available or can be synthesized by methods known to the person skilled in the art.

In another embodiment of the present invention, R⁴ of the compound of of formula (IIIa), (IIIb), (VIIa) or (VIIb) represents a group selected from tetrahydro-2H-pyran-2-yl, 1-methyl-1-methoxyethyl, 1-methyl-1-phenoxyethyl, 1-methyl-1-benzyloxyethyl.

In a preferred embodiment of the present invention, R⁴ of the compound of of formula (IIIa), (IIIb), (VIIa) or (VIIb) represents a tetrahydro-2H-pyran-2-yl group.

In another preferred embodiment of the present invention the intermediate compound of formula (VIIa) is the compound of formula (VIIc)

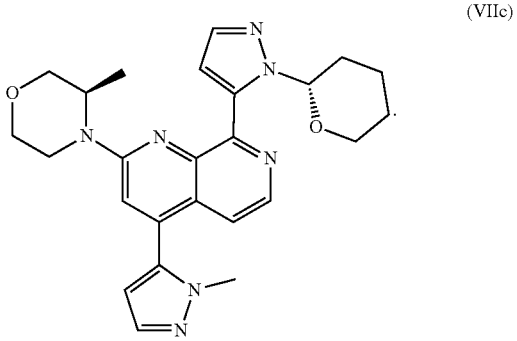 [SMILES: C[C@@H]1COCCN1c1cc(-c2ccnn2C)c2ccnc(-c3ccnn3[C@@H]3CCCCO3)c2n1]

(VIIc)

In another preferred embodiment of the present invention the intermediate compound of formula (VIIa) is the compound of formula (VIId)

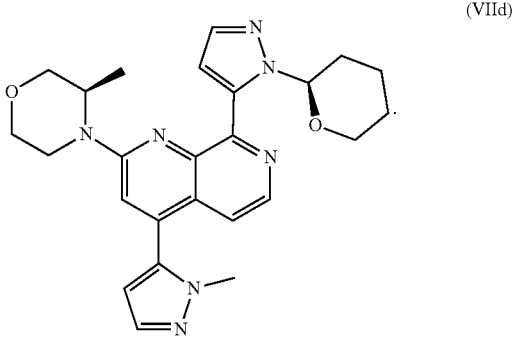 [SMILES: C[C@@H]1COCCN1c1cc(-c2ccnn2C)c2ccnc(-c3ccnn3[C@H]3CCCCO3)c2n1]

(VIId)

In another preferred embodiment of the present invention the intermediate compound of formula (VIIa) is a mixture, particularly a 1:1 mixture, of the compounds of formula (VIIc) and (VIId). Said 1:1 mixture is (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl)morpholine, which is also called compound of formula (VIIc/VIId) in the following:

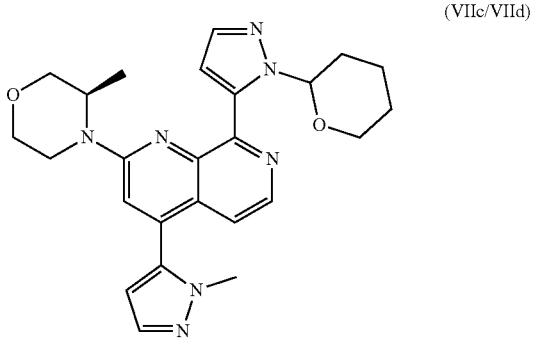 [SMILES: C[C@@H]1COCCN1c1cc(-c2ccnn2C)c2ccnc(-c3ccnn3C3CCCCO3)c2n1]

(VIIc/VIId)

In another embodiment of the method according to the present invention the intermediate compound of formula (IXa) is reacted with a compound of formula (IIIa).

In a preferred embodiment of the method according to the present invention (R)-4-(8-chloro-4-(1-methyl-1H-pyrazol-5-yl)-1,7-naphthyridin-2-yl)-3-methyl-morpholine (IXb) is reacted with 1-(tetrahydro-2H-pyran-2-yl)-1H-pyrazole-5-boronic acid pinacol ester (IIIc).

In a preferred embodiment of the method according to the present invention, the compound of formula (IXa) is (R)-4-(8-chloro-4-(1-methyl-1H-pyrazol-5-yl)-1,7-naphthyridin-2-yl)-3-methyl-morpholine; and/or the compound of formula (IIIa) is 1-(tetrahydro-2H-pyran-2-yl)-1H-pyrazole-5-boronic acid pinacol ester; and/or the compound of formula (VIIa) is (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl)morpholine.

In another embodiment of the method according to the present invention the intermediate compound of formula (IXa) is reacted with 0.95-2.0 molar equivalents of the compound of formula (IIIa) or (IIIb), preferably with 1.0-1.7 molar equivalents of the compound of formula (IIIa) or (IIIb), most preferably with 1.2-1.5 molar equivalents of the compound of formula (IIIa) or (IIIb).

In another embodiment of the method according to the present invention the intermediate compound of formula (IXa) is reacted with 0.95-2.0 molar equivalents of 1-(tetrahydro-2H-pyran-2-yl)-1H-pyrazole-5-boronic acid pinacol ester (IIIc), preferably with 1.0-1.7 molar equivalents of 1-(tetrahydro-2H-pyran-2-yl)-1H-pyrazole-5-boronic acid pinacol ester (IIIc), most preferably with 1.2-1.5 molar equivalents of 1-(tetrahydro-2H-pyran-2-yl)-1H-pyrazole-5-boronic acid pinacol ester (IIIc).

In another embodiment of the method according to the present invention (R)-4-(8-chloro-4-(1-methyl-1H-pyrazol-5-yl)-1,7-naphthyridin-2-yl)-3-methyl-morpholine (IXb) is reacted with 0.95-2.0 molar equivalents of 1-(tetrahydro-2H-pyran-2-yl)-1H-pyrazole-5-boronic acid pinacol ester (IIIc), preferably with 1.0-1.7 molar equivalents of 1-(tetrahydro-2H-pyran-2-yl)-1H-pyrazole-5-boronic acid pinacol ester (IIIc), most preferably with 1.2-1.5 molar equivalents of 1-(tetrahydro-2H-pyran-2-yl)-1H-pyrazole-5-boronic acid pinacol ester (IIIc).

In another embodiment of the method according to the present invention the compound of formula (IIIa) or (IIIb), particularly 1-(tetrahydro-2H-pyran-2-yl)-1H-pyrazole-5-boronic acid pinacol ester (IIIc), is dissolved in a solvent, for example in isopropylacetate, ethyl acetate, 1,2-dimethoxyethane, dioxane, N,N-dimethylformamide (=DMF), 1,2-dimethoxyethane (=DME), tetrahydrofuran (=THF), 2-methyl-tetrahydrofuran (=2-Me-THF) or isopropanol.

In a preferred embodiment of the method according to the present invention the compound of formula (IIIa) or (IIIb), particularly 1-(tetrahydro-2H-pyran-2-yl)-1H-pyrazole-5-boronic acid pinacol ester (IIIc), is dissolved in isopropyl acetate or ethyl acetate, most preferred is ethyl acetate.

In another embodiment of the method according to the present invention the compound of formula (IXa) or (IXb) is dissolved in a solvent, for example in isopropylacetate, ethyl acetate, 1,2-dimethoxyethane, dioxane, N,N-dimethylformamide (=DMF), 1,2-dimethoxyethane (=DME), tetrahydrofuran (=THF), 2-methyl-tetrahydrofuran (=2-Me-THF) or isopropanol.

In a preferred embodiment of the method according to the present invention the compound of formula (IXa) or (IXb), particularly (IXb), is dissolved in isopropyl acetate or ethyl acetate, most preferred is ethyl acetate.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methyl-morpholine, with a compound of formula (IIIa) or (IIIb), particularly with 1-(tetrahydro-2H-pyran-2-yl)-1H-pyrazole-5-boronic acid pinacol ester, is performed for 1-36 hours, particularly for 1.5-5 hours, preferably for 1.5-3 hours, most preferably for 100-140 minutes.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine, with a compound of formula (IIIa) or (IIIb), particularly with 1-(tetrahydro-2H-pyran-2-yl)-1H-pyrazole-5-boronic acid pinacol ester, is performed in the presence of a suitable catalyst system, like for example a palladium catalyst.

In another embodiment of the method according to the present invention the palladium catalyst is selected from the group consisting of [1,1'-bis(diphenylphosphino)ferrocene]dichloro palladium(II), palladium (II) acetate, bis(triphenylphosphine)palladium(II)dichloride, dichlorobis(tricyclohexylphosphine)palladium(II), (2-dicyclohexylphosphino-2',4',6'-triisopropyl-1,1'-biphenyl)[2-(2-aminoethyl)phenyl)]palladium(II)chloride, chloro (2-dicyclohexylphosphino-2',4',6'-triisopropyl-1,1'-biphenyl)[2-(2'-amino-1,1'-biphenyl)]palladium(II), tetrakis(triphenylphosphine)palladium(0), bis(tri-tert-butylphosphine)palladium(0), bis[tris(2-methylphenyl)phosphine]palladium(0), tris(dibenzylideneacetone)dipalladium(0).

In a preferred embodiment of the method according to the present invention the palladium catalyst is [1,1'-bis(diphenylphosphino)ferrocene]dichloro palladium(II).

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine, with a compound of formula (IIIa) or (IIIb), particularly with 1-(tetrahydro-2H-pyran-2-yl)-1H-pyrazole-5-boronic acid pinacol ester, is performed in the presence of 0.001-0.1 molar equivalents, preferably of 0.005-0.05 molar equivalents, most preferably of 0.01-0.03 molar equivalents of the palladium catalyst, preferably of [1,1'-bis(diphenylphosphino)ferrocene]dichloro palladium(II).

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine (IXb), with a compound of formula (IIIa) or (IIIb), particularly with 1-(tetrahydro-2H-pyran-2-yl)-1H-pyrazole-5-boronic acid pinacol ester (IIIc), is performed in an organic solvent, wherein the solvent comprises isopropyl acetate, ethyl acetate, 1,2-dimethoxyethane, 1,4-dioxane, dimethylformamide, tetrahydrofuran, 2-methyltetrahydrofuran, methanol, ethanol, 1-propanol, isopropanol, 1-butanol or 2-butanol; or wherein said reaction is performed in a solvent mixture comprising one or more of said solvents and water.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine, with a compound of formula (IIIa) or (IIIb), particularly with 1-(tetrahydro-2H-pyran-2-yl)-1H-pyrazole-5-boronic acid pinacol ester, is performed in an organic solvent, wherein the solvent comprises isopropyl acetate and ethyl acetate; or wherein said reaction is performed in a solvent mixture comprising isopropyl acetate and water or comprising ethyl acetate and water. Preferably the solvent mixture comprises ethyl acetate and water.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine, with a compound of formula (IIIa) or (IIIb), particularly with 1-(tetrahydro-2H-pyran-2-yl)-1H-pyrazole-5-boronic acid pinacol ester, per kg of compound of formula (IXa) 5-20 kg of the organic solvent, preferably 6-15 kg of the organic solvent, most preferably 7-11 kg of the organic solvent is used. Preferred organic solvent comprises isopropyl acetate or ethyl acetate, preferred solvent mixture comprises isopropyl acetate and water or it comprises ethyl acetate and water.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine (IXb), with a compound of formula (IIIa) or (IIIb), particularly with 1-(tetrahydro-2H-pyran-2-yl)-1H-pyrazole-5-boronic acid pinacol ester (IIIc), per kg of compound of formula (IXa) or (IXb) 5-20 kg of the organic solvent and 1-5 kg of water, preferably 6-15 kg of the organic solvent and 1-4 kg of water, most preferably 7-11 kg of the organic solvent and 1.5-2.5 kg of water are used.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine (IXb), with a compound of formula (IIIa) or (IIIb), particularly with 1-(tetrahydro-2H-pyran-2-yl)-1H-pyrazole-5-boronic acid pinacol ester (IIIc), is performed in the presence of a base. Bases like potassium phosphate, potassium carbonate, potassium hydrogen carbonate, sodium phosphate, sodium carbonate, sodium hydrogen carbonate, barium hydroxide, barium carbonate, cesium carbonate or lithium carbonate can be used. Potassium phosphate or sodium phosphate are preferred, most preferred is potassium phosphate.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine (IXb), with a compound of formula (IIIa) or (IIIb), particularly with 1-(tetrahydro-2H-pyran-2-yl)-1H-pyrazole-5-boronic acid pinacol ester (IIIc), is performed in the presence of 1-15 molar equivalents, preferably of 2-11 molar equivalents, most preferably of 3-10 molar equivalents of base.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine (IXb), with a compound of formula (IIIa) or (IIIb) is performed in the presence of a palladium catalyst and/or a base.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine (IXb), with a compound of formula (IIIa) or (IIIb), particularly with 1-(tetrahydro-2H-pyran-2-yl)-1H-pyrazole-5-boronic acid pinacol ester (IIIc), is performed at temperatures ranging from room temperature to the boiling point of the solvent.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine (IXb), with a compound of formula (IIIa) or (IIIb), particularly with 1-(tetrahydro-2H-pyran-2-yl)-1H-pyrazole-5-boronic acid pinacol ester (IIIc), is performed under pressure at temperatures above the boiling point.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine, with a compound of formula (IIIa) or (IIIb), particularly with 1-(tetrahydro-2H-pyran-2-yl)-1H-pyrazole-5-boronic acid pinacol ester, is performed in isopropyl acetate or in isopropyl acetate and water at a temperature of 55-75° C., preferably at 60-70° C., most preferably at 65° C.

In another embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine, with a compound of formula (IIIa) or (IIIb), particularly with 1-(tetrahydro-2H-pyran-2-yl)-1H-pyrazole-5-boronic acid pinacol ester, is performed in ethyl acetate or in ethyl acetate and water at a temperature of 45-65° C., preferably at 50-60° C., most preferably at 55° C.

Particularly, if the reaction of the intermediate compound of formula (IXa), preferably of (R)-4-(8-chloro-4-(1-methyl-1H-pyrazol-5-yl)-1,7-naphthyridin-2-yl)-3-methylmorpholine, with a compound of formula (IIIa) or (IIIb), preferably with 1-(tetrahydro-2H-pyran-2-yl)-1H-pyrazole-5-boronic acid pinacol ester, is performed in a mixture of ethyl acetate and water, said ethyl acetate and said water are stirred, particularly vigorously stirred. Preferably ethyl acetate and water are stirred at conditions which ensure that the ethyl acetate phase and the water phase are sufficiently mixed.

In a preferred embodiment of the method according to the present invention the reaction of the intermediate compound of formula (IXa), particularly of (R)-4-(8-chloro-4-(1-methyl-1H-pyrazol-5-yl)-1,7-naphthyridin-2-yl)-3-methylmorpholine (IXb), with a compound of formula (IIIa) or (IIIb), particularly with 1-(tetrahydro-2H-pyran-2-yl)-1H-pyrazole-5-boronic acid pinacol ester (IIIc), is performed under inert gas atmosphere, wherein the inert gas is nitrogen or argon, preferably nitrogen.

1.1 Further Processing of the Crude Intermediate Compound of Formula (VIIa), (VIIb), (VIIc), (VIId) or (VIIc/VIId)

In another embodiment of the method according to the present invention the intermediate compound of formula (VIIa) or (VIIb), which is obtained by the reaction of the intermediate compound of formula (IXa) with the intermediate compound of formula (IIIa) or (IIIb), is not isolated after said reaction ("the crude intermediate compound of formula (VIIa) or (VIIb)" in the following) and/or the intermediate compound of formula (VIIa) or (VIIb) is not purified.

In a preferred embodiment of the method according to the present invention the intermediate compound of formula (VIIc/VIId), which is obtained by the reaction of the intermediate compound of formula (IXb) with the intermediate compound of formula (IIIc), is not isolated after said reaction ("the crude intermediate compound of formula (VIIc/VIId)" in the following) and/or the intermediate compound of formula (VIIc/VIId) is not purified.

In another embodiment of the method according to the present invention the intermediate compound of formula (VIIa) or (VIIb) is not isolated and/or is not purified prior to removing the group $R^4$ from the intermediate compound of formula (VIIa) or of formula (VIIb). The crude intermediate compound of formula (VIIa) or (VIIb) is directly converted to the compound of formula (I), or to its tautomer of formula (Ia), by removing the group $R^4$ from the compound of formula (VIIa) or (VIIb).

In a preferred embodiment of the method according to the present invention the intermediate compound of formula (VIIc), (VIId) or (VIIc/VIId) is not isolated and/or is not purified prior to removing the group $R^4$ from the intermediate compound of formula (VIIc), (VIId) or (VIIc/VIId). The crude intermediate compound of formula (VIIc), (VIId) or (VIIc/VIId) is directly converted to the compound of formula (I), or to its tautomer of formula (Ia), by removing the group $R^4$ from the compound of formula (VIIc), (VIId) or (VIIc/VIId).

In another embodiment of the method according to the present invention the intermediate compound of formula (VIIa), (VIIb), (VIIc), (VIId) or (VIIc/VIId) is not isolated and/or is/are not purified prior to removing the group $R^4$ from the intermediate compound of formula (VIIa), (VIIb), (VIIc), (VIId) or (VIIc/VIId), and after the reaction of the intermediate compound of formula (IXa) or (IXb) with a compound of formula (IIIa), (IIIb) or (IIIc) and before removing the group $R^4$ from the intermediate compound of formula (VIIa), (VIIb), (VIIc), (VIId) or (VIIc/VIId), the solvent or solvent mixture of said reaction is replaced by another solvent ("solvent X" in the following), wherein solvent X comprises a solvent selected from dichloromethane, ethyl acetate, isopropyl acetate, tetrahydrofuran, 2-methyl-tetrahydrofuran, toluoyl, chloroform or mixtures thereof; and, optionally, a) solvent X is washed with an aqueous solution of a base selected from potassium hydroxide, potassium carbonate, potassium hydrogen carbonate, potassium hydroxide, potassium tert-butoxide, sodium hydroxide, sodium phosphate, sodium carbonate, sodium hydroxide, sodium tert-butoxide, barium hydroxide, cesium carbonate, triethylamine; preferably solvent X is washed with potassium hydroxide; and, optionally, b) the solvent X is treated with an adsorbent; preferably the adsorbent is activated charcoal; and optionally c) the adsorbent, particularly the activated charcoal, is filtered;

to give a solution of the compound of formula (VIIa), (VIIb), (VIIc), (VIId) or (VIIc/VIId) in solvent X.

Suitable adsorbents, such as for example activated charcoal (=activated carbon), oxides such as those of Al, Mg, Th, Ti, Zr and B, and their mixtures, silicic acid, boric acid, silicates such as diatomaceous earth, kieselguhr and silica gel; fuller's earth, florida earth, and clays such as bentonites, montmorillonites and acid-treated clays, resins, activated alumina or zeolites are known to the person skilled in the art.

In another embodiment of the method according to the present invention the intermediate compound of formula (VIIa), (VIIb), (VIIc), (VIId) or (VIIc/VIId) is not isolated and/or is not purified prior to removing the group $R^4$ from the intermediate compound of formula (VIIa), (VIIb), (VIIc), (VIId) or (VIIc/VIId), and after the reaction of the intermediate compound of formula (IXa) or (IXb) with a compound of formula (IIIa), (IIIb) or (IIIc) and before removing the group $R^4$ from the intermediate compound of formula (VIIa), (VIIb), (VIIc), (VIId) or (VIIc/VIId), the solvent or solvent mixture of said reaction, particularly ethyl acetate with/without water, or isopropyl acetate with/without water, is replaced by another solvent comprising dichloromethane; and, optionally, a) the resulting dichloromethane solution is washed with an aqueous solution of a base selected from potassium hydroxide, potassium carbonate, potassium hydrogen carbonate, potassium hydroxide, potassium tert-butoxide, sodium hydroxide, sodium phosphate, sodium carbonate, sodium hydroxide, sodium tert-butoxide, barium hydroxide, cesium carbonate, triethylamine; preferably dichloromethane is washed with potassium hydroxide; and, optionally, b) the resulting dichloromethane solution is treated with an adsorbent; preferably the adsorbent is activated charcoal; and optionally c) the adsorbent, particularly the activated charcoal, is filtered;

to give a solution of the compound of formula (VIIa), (VIIb), (VIIc), (VIId) or (VIIc/VIId) in dichloromethane.

In another embodiment of the method according to the present invention the intermediate compound of formula (VIIc/VIId) is not isolated and/or is not purified prior to removing the group $R^4$ from the intermediate compound of formula (VIIc/VIId), and after the reaction of (R)-4-(8-chloro-4-(1-methyl-1H-pyrazol-5-yl)-1,7-naphthyridin-2-yl)-3-methyl-morpholine (IXb) with 1-(tetrahydro-2H-pyran-2-yl)-1H-pyrazole-5-boronic acid pinacol ester (IIIc) and before removing the group $R^4$ from the intermediate compound of formula (VIIc/VIId), the solvent or solvent mixture of said reaction, particularly isopropyl acetate with/without water or ethyl acetate with/without water, is replaced by another solvent comprising dichloromethane; and, a) the resulting dichloromethane solution is washed with an aqueous solution of a base selected from potassium hydroxide, potassium carbonate, potassium hydrogen carbonate, potassium hydroxide, potassium tert-butoxide, sodium hydroxide, sodium phosphate, sodium carbonate, sodium hydroxide, sodium tert-butoxide, barium hydroxide, cesium carbonate, trimethylamine, preferably dichloromethane is washed with potassium hydroxide; and/or b) the resulting dichloromethane solution is treated with an adsorbent; preferably the adsorbent is activated charcoal; and the adsorbent is filtered;

to give a purified solution of the intermediate compound of formula (VIIc/VIId) in dichloromethane ("the purified solution of the intermediate compound of formula (VIIc/VIId) in dichloromethane" in the following).

In another embodiment of the method according to the present invention the intermediate compound of formula (VIIa), (VIIb), (VIIc), (VIId) or (VIIc/VIId) is not isolated and/or is not purified prior to removing the group $R^4$ from the intermediate compound of formula (VIIa), (VIIb), (VIIc), (VIId) or (VIIc/VIId), and after the reaction of the intermediate compound of formula (IXa) or (IXb) with a compound of formula (IIIa), (IIIb) or (IIIc) and before removing the group $R^4$ from the intermediate compound of formula (VIIa), (VIIb), (VIIc), (VIId) or (VIIc/VIId), the solvent of said reaction, particularly ethyl acetate with/without water or isopropyl acetate with/without water, preferably ethyl acetate and water, is washed with water and/or treated with an adsorbent, defined supra, particularly with activated charcoal, to give a purified solution of the intermediate compound of formula (VIIa), (VIIb), (VIIc), (VIId) or (VIIc/VIId), particularly a purified solution in ethyl acetate or isopropyl acetate ("the purified solution of the intermediate compound of formula (VIIa), (VIIb), (VIIc), (VIId) or (VIIc/VIId) in ethyl acetate or isopropyl acetate" in the following).

In another embodiment of the method according to the present invention the intermediate compound of formula (VIIc/VIId) is not isolated and/or is not purified prior to removing the group $R^4$ from the intermediate compound of formula (VIIc/VIId), and after the reaction of the intermediate compound of formula (IXb) with a compound of formula (IIIc) and before removing the group $R^4$ from the intermediate compound of formula (VIIc/VIId), the solvent of said reaction, particularly ethyl acetate with/without water or isopropyl acetate with/without water, preferably ethyl acetate and water, is washed with water and/or treated with an adsorbent, defined supra, particularly with activated charcoal, to give a purified solution of the intermediate compound of formula (VIIc/VIId) ("the purified solution of the intermediate compound of formula (VIIc/VIId)"), particularly a solution of (VIIc/VIId) in ethyl acetate or in isopropyl acetate ("the purified solution of the intermediate compound of formula (VIIc/VIId) in ethyl acetate or isopropyl acetate" in the following), preferably a solution of the intermediate compound of formula (VIIc/VIId) in ethyl acetate ("the purified solution of the intermediate compound of formula (VIIc/VIId) in ethyl acetate" in the following).

1.2 Removing the $R^4$ Group from the Intermediate Compound of Formula (VIIa), (VIIb), (VIIc), (VIId) or (VIIc/VIId) to Obtain the Crude Compound of Formula (I)

In another embodiment of the method according to the present invention the group $R^4$ is removed from the intermediate compound of formula (VIIa) or of formula (VIIb) by reacting the intermediate compound of formula (VIIa) or of formula (VIIb) with an acid, like for example aqueous hydrochloric acid, aqueous hydrochloric acid with methanol, hydrochloric acid with methanol, aqueous hydrochloric acid with ethanol, hydrochloric acid with ethanol, aqueous hydrochloric acid with 1-propanol, hydrochloric acid with 1-propanol, aqueous hydrochloric acid with isopropanol, hydrochloric acid with isopropanol, aqueous hydrochloric acid with 1-butanol, hydrochloric acid with 1-butanol, aqueous hydrochloric acid with 2-butanol, hydrochloric acid with 2-butanol, aqueous sulfuric acid, methane sulfonic acid, p-toluenesulfonic acid, trifluoro acetic acid or phosphoric acid or mixtures of one or more of said acids (hydrochloric acid, aqueous sulfuric acid, methane sulfonic acid, p-toluenesulfonic acid, trifluoro acetic acid and/or phosphoric acid) with one or more alcohols, such as methanol, ethanol, 1-propanol, isopropanol, 1-butanol, 2-butanol. Preferably, the acid comprises aqueous hydrochloric acid with methanol.

In another embodiment of the method according to the present invention the group $R^4$ is removed from the intermediate compound of formula (VIIc), (VIId) or (VIIc/VIId), by reacting the intermediate compound of formula (VIIc), (VIId) or (VIIc/VIId), with an acid, as defined supra.

0.7-10 molar equivalents of acid can be used, preferably 1-7.5 molar equivalents, most preferably 1.5-5 molar equivalents. Aqueous hydrochloric acid is preferred, particularly aqueous hydrochloric acid with methanol or aqueous hydrochloric acid with methanol with ethyl acetate.

Particularly, when removing the group $R^4$ according to the method of the present invention the pH is less than 3 (pH<3), preferably less than 2 (pH<2), most preferably less than 1.5 (pH<1.5).

In another embodiment of the method according to the present invention when removing the group $R^4$ from the intermediate compound of formula (VIIa), (VIIb), (VIIc), (VIId) or (VIIc/VIId) with an acid in a solvent, the solvent is a protic or aprotic solvent, like for example methanol, ethanol, propanol, butanol, dichloromethane, tetrahydrofuran (=THF), 2-methyl-tetrahydrofuran (=2-Me-THF), 1,4-dioxane, 1,2-dimethoxyethane, ethyl acetate, isopropyl acetate; or the solvent is a solvent mixture of said solvent(s) optionally further comprising water. Preferred solvent comprises dichloromethane, preferred solvent mixture comprises dichloromethane with methanol, or methanol with ethyl acetate, or methanol with ethyl acetate and water, or methanol with isopropyl acetate or methanol with isopropyl acetate and water.

In another embodiment of the method according to the present invention when removing the group $R^4$ from the intermediate compound of formula (VIIa), (VIIb), (VIIc), (VIId) or (VIIc/VIId) the acid is selected from the group consisting of hydrochloric acid, aqueous hydrochloric acid, aqueous hydrochloric acid in methanol, aqueous hydrochloric acid in isopropanol, aqueous hydrochloric acid in methanol and dichloromethane, and aqueous hydrochloric acid in methanol and ethyl acetate.

In a preferred embodiment of the method according to the present invention when removing the group $R^4$ from the intermediate compound of formula (VIIc/VIId) the acid is aqueous hydrochloric acid and the solvent mixture comprises dichloromethane and methanol, particularly dichloromethane, methanol and water.

In a preferred embodiment of the method according to the present invention when removing the group $R^4$ from the purified solution of the intermediate compound of formula (VIIc/VIId) in dichloromethane, defined above, the acid is aqueous hydrochloric acid and the solvent mixture comprises dichloromethane, methanol and water.

When using aqueous hydrochloric acid in methanol and dichloromethane, per kg of compound of formula (VIIa), (VIIb), (VIIc), (VIId) or (VIIc/VIId) 1-20 kg of 1N aqueous hydrochloric acid in 1-20 kg methanol and 1-20 kg dichloromethane is used. Preferably 5-15 kg of 1N aqueous hydrochloric acid in 2-15 kg methanol and 2-15 kg dichloromethane is used.

In a preferred embodiment of the method according to the present invention when removing the group $R^4$ from the intermediate compound of formula (VIIc/VIId) the acid is aqueous hydrochloric acid and the solvent mixture comprises methanol with ethyl acetate, or methanol with isopropyl acetate, preferably the solvent mixture comprises methanol with ethyl acetate and water.

In a preferred embodiment of the method according to the present invention when removing the group $R^4$ from the purified solution of the intermediate compound of formula (VIIc/VIId) in ethyl acetate or isopropyl acetate, defined above, the acid is aqueous hydrochloric acid, particularly 1N aqueous hydrochloric acid, and the solvent mixture comprises methanol with ethyl acetate with/without water, or methanol with isopropyl acetate with/without water, preferably the solvent mixture comprises methanol with ethyl acetate and water.

The use of solvent mixtures comprising methanol is particularly advantageous in order to prevent the formation of side products such as for example

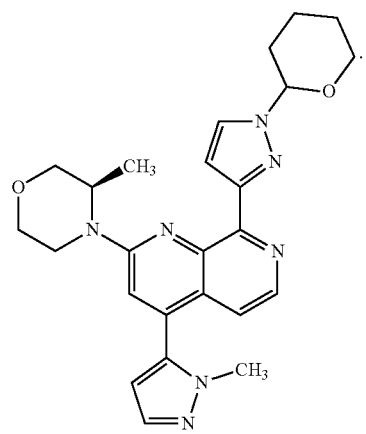 [SMILES: C[C@@H]1COCCN1c1cc(-c2ccnn2C)c2ccnc(-c3ccn(C4CCCCO4)n3)c2n1]

When using aqueous hydrochloric acid in methanol and ethyl acetate, per kg of compound of formula (VIIa), (VIIb), (VIIc), (VIId) or (VIIc/VIId) 1-20 kg of 1N aqueous hydrochloric acid in 1-20 kg methanol and 1-20 kg ethyl acetate is used. Preferably 5-15 kg of 1N aqueous hydrochloric acid in 2-15 kg methanol and 2-15 kg of ethyl acetate is used.

In another embodiment of the method according to the present invention the reaction of the intermediate compound of formula (VIIa) or of formula (VIIb), preferably of the compound of formula (VIIc) or (VIId) or of the mixture of the compounds of formula (VIIc) and (VIId), with an acid is performed at a temperature of −10-40° C., preferred at 0-30° C., most preferred at 10-25° C. The reaction time is 2-60 min, preferably 2-30 min, most preferably 5-20 min.

In another embodiment of the method according to the present invention the reaction to remove the group $R^4$ from the intermediate compound of formula (VIIa), (VIIb), (VIIc), (VIId) or (VIIc/VIId) with an acid is performed under inert gas atmosphere, wherein the inert gas is nitrogen or argon, preferably nitrogen.

Directly after completion of the reaction of the intermediate compound of formula (VIIa), (VIIb), (VIIc), (VIId) or (VIIc/VIId) with an acid a crude compound of formula (I) ("the crude compound of formula (I)" in the following) is obtained.

After the removal of the group $R^4$ from the intermediate compound of formula (VIIc/VIId) with aqueous hydrochloric acid in a solvent mixture comprising dichloromethane, methanol and water the crude compound of formula (I) is dissolved in an acidified aqueous phase (in the following "the acidified aqueous solution of the crude compound of formula (I)"), wherein the pH of the resulting acidified aqueous solution is less than 3 (pH<3), preferably less than 2 (pH<2), most preferably less than 1.5 (pH<1.5).

The crude compound of formula (I) can be further processed (section 1.3) and/or crystallized (section 1.4).

1.3 Further Processing of the Crude Compound of Formula (I)

In another embodiment of the method according to the present invention for preparing the compound of formula (I),
a) the acidified aqueous solution of the crude compound of formula (I), described supra, is extracted one or more times with solvent A, defined infra, and/or is treated one or more times with a Pd scavenger, defined infra;
b) the acidified aqueous solution of the crude compound of formula (I) obtained by previous step a) is treated with solvent A and with an aqueous solution of a base, defined infra, to give a two-phase system, in which the aqueous phase of said two-phase system has a pH>12;

c) the aqueous phase is separated from said two-phase system to give a solution of the crude compound of formula (I) in solvent A; and, optionally, d) replacing the solvent A of the solution of the crude compound of formula (I) in solvent A by solvent B, defined infra, to give a solution of the crude compound of formula (I) in solvent B.

In a preferred embodiment of the method according to the present invention for preparing the compound of formula (I), a) the acidified aqueous solution of the crude compound of formula (I), described supra, is extracted one or more times with dichloromethane and/or is treated one or more times with a Pd scavenger, defined infra;

b) the acidified aqueous solution of the crude compound of formula (I) obtained by previous step a) is treated with dichloromethane and with an aqueous solution of potassium hydroxide, particularly with a 5N aqueous solution of potassium hydroxide, to give a two-phase system, in which the aqueous phase of said two-phase system has a pH>12;

c) the aqueous phase is separated from said two-phase system to give a solution of the crude compound of formula (I) in dichloromethane; and, optionally, d) replacing the dichloromethane of the solution of the crude compound of formula (I) in dichloromethane by n-butanol to give a solution of the crude compound of formula (I) in n-butanol.

In another embodiment of the method according to the present invention for preparing the compound of formula (I), the crude compound of formula (I) is dissolved in a solvent ("solvent A" in the following), wherein solvent A comprises a solvent selected from dichloromethane, ethyl acetate, isopropyl acetate, tetrahydrofuran, 2-methyl-tetrahydrofuran, toluoyl, chloroform; or in a solvent mixture of one or more of said solvents A ("solvent mixture A"); preferred solvent A is dichloromethane.

Preferably solvent A comprises the same solvent or solvent mixture as the solvent/solvent mixture which was used for the reaction to remove group $R^4$ from the intermediate compound of formula (VIIa), (VIIb), (VIIc), (VIId) or (VIIc/VIId).

In another embodiment of the method according to the present invention for preparing the compound of formula (I), the crude compound of formula (I) is dissolved in dichloromethane.

In another embodiment of the method according to the present invention for preparing the compound of formula (I), the crude compound of formula (I) dissolved in the solvent A is treated with an aqueous solution of a base selected from potassium hydroxide, potassium carbonate, potassium hydrogen carbonate, potassium hydroxide, potassium tert-butoxide, sodium hydroxide, sodium phosphate, sodium carbonate, sodium hydroxide, sodium tert-butoxide, barium hydroxide, cesium carbonate, triethylamine; preferably dichloromethane is washed with potassium hydroxide. Preferably the crude compound of formula (I) dissolved in the solvent A, particularly dichloromethane, is treated with potassium hydroxide.

Particularly, when treating the crude compound of formula (I) dissolved in the solvent A, particularly in dichloromethane, with an aqueous solution of a base, defined supra, the pH is more than 11 (pH>11), preferably more than 12 (pH>12), most preferably the pH=12-14, particularly pH=12.5-13.5.

In another embodiment of the method according to the present invention for preparing the compound of formula (I), the crude compound of formula (I) dissolved in the solvent A, preferably dissolved in dichloromethane, is treated with a palladium scavenger, defined infra.

In another embodiment of the method according to the present invention for preparing the compound of formula (I), the crude compound of formula (I) dissolved in the solvent A, preferably dissolved in dichloromethane, is treated with an aqueous solution of a base, defined supra, and is then treated with a palladium scavenger, defined infra.

In another embodiment of the method according to the present invention for preparing the compound of formula (I), the crude compound of formula (I) dissolved in the solvent A, preferably dissolved in dichloromethane, is treated with a palladium scavenger, defined infra, and is then treated with an aqueous solution of a base, defined supra.

A palladium scavenger is a reagent which can be used to separate the palladium of the palladium catalyst from the crude compound of formula (I). Different palladium scavengers are for example further described by Garret and Prasad (Advanced Synthesis & Catalysis (2004), 346 (8), 889-900CODEN: ASCAF7; ISSN: 1615-4150, Wiley-VCH Verlag GmbH & Co. KGaA). They include, for example, trimercaptotriazine (TMT), polystyrene-bound TMT, MP-TMT (a highly cross-linked macro-porous polystyrene-bound trimercaptotriazine resin), polystyrene-bound ethylenediamine, activated carbon, glass bead sponges, smopex (=polyethylene or cellulose based fibers containing grafted side chains with appropriate functional groups for the complexation of metals), polymer-bound ligands, and silica-bound ligands.

In one embodiment of the present invention the palladium scavenger is selected from the group consisting of N-acetyl cysteine, Quadrasil Mercaptopropyl (CAS Number 1225327-73-0) and Isolute Si-TMT (Pd scavenger from Biotage AB, Sweden, Part No. 9538-1000) the silica bound equivalent of 2,4,6-trimercaptotriazine, or is a mixture thereof.

In another embodiment of the present invention the palladium scavenger comprises a mixture of N-acetyl cysteine with Quadrasil Mercaptopropyl, of N-acetyl cysteine with Isolute Si-TMT, or of Isolute Si-TMT with Quadrasil Mercaptopropyl.

Most preferred palladium scavenger comprises a mixture of N-acetyl cysteine, Quadrasil Mercaptopropyl and Isolute Si-TMT.

In another embodiment of the method according to the present invention for preparing the compound of formula (I), the solvent A, defined supra, is replaced by a solvent ("solvent B" in the following) selected from ethanol, n-propanol, n-butanol, 2-butanol, isopropanol, preferably solvent A is replaced by n-butanol.

In another embodiment of the method according to the present invention for preparing the compound of formula (I), dichloromethane (solvent A) is replaced by n-butanol (solvent B).

In another embodiment of the method according to the present invention for preparing the compound of formula (I) the solvent A is replaced by the solvent B after the treatment of the solvent A with the Pd scavenger, and/or after the treatment of the solvent A with the aqueous solution of the base.

In another embodiment of the method according to the present invention for preparing the compound of formula (I), dichloromethane is replaced by n-butanol after the treatment of dichloromethane with the Pd scavenger and/or after the treatment of dichloromethane with the aqueous solution of the base.

In another embodiment of the method according to the present invention for preparing the compound of formula (I) the solvent A is replaced by solvent B after the treatment of solvent A with the Pd scavenger and/or after the treatment of solvent A with the aqueous solution of a base; and solvent B is then treated with the Pd scavenger.

In another embodiment of the method according to the present invention for preparing the compound of formula (I) the dichloromethane is replaced by n-butanol after the treatment of dichloromethane with the Pd scavenger, and/or after the treatment of dichloromethane with the aqueous solution of the base; and n-butanol is then treated with the Pd scavenger.

In another embodiment of the method according to the present invention for preparing the compound of formula (I) the solvent A is replaced by solvent B before the treatment of solvent A with the Pd scavenger, and solvent B is then treated with the Pd scavenger.

In another embodiment of the method according to the present invention for preparing the compound of formula (I), dichloromethane is replaced by n-butanol before the treatment of dichloromethane with the Pd scavenger, and n-butanol is then treated with the Pd scavenger.

1.4 Crystallization of the Crude Compound of Formula (I) to Give its Polymorphic Form B The crystallization step provides polymorphic form B of the compound of formula (I) (=Mod B) through a reproducible and robust process, which can be characterized, first, by a solvent switch from solvent A to solvent B, and, second, by a subsequent crystallization step.

1.4.1 Solvent Switch

In another embodiment of the method according to the present invention for preparing the compound of formula (I) the crude compound of formula (I) dissolved in solvent A, preferably in dichloromethane, is crystallized in solvent B to give the polymorphic form B of the compound of formula (I).

To crystallize the compound of formula (I) in its polymorphic form B solvent A first has to be replaced by solvent B ("solvent switch"). Therefore, in another embodiment of the method according to the present invention for preparing the compound of formula (I) solvent A, preferably dichloromethane, is replaced by solvent B, preferably n-butanol.

in another embodiment of the method according to the present invention for preparing the compound of formula (I) solvent A, preferably dichloromethane, is replaced by solvent B, preferably n-butanol, by, first, mixing solvent A and solvent B; and, second, distilling off solvent A at standard pressure or at reduced pressure.

In another embodiment of the method according to the present invention for preparing the compound of formula (I) solvent A is replaced by solvent B by, first, mixing solvent A and solvent B to form an azeotropic mixture; and, second, separating solvent A from solvent B by conventional methods, which are known to the person skilled in the art, to give "the compound of formula (I) dissolved in solvent B".

In another embodiment "the compound of formula (I) dissolved in solvent B" is heated to give "the compound of formula (I) dissolved in heated solvent B". Particularly solvent B is heated to a temperature of at least 40° C., preferably to a temperature of 60-120° C., preferably to a temperature of 90-110° C. to give "the compound of formula (I) dissolved in heated solvent B".

In another embodiment of the method according to the present invention for preparing the compound of formula (I) dichloromethane (solvent A) is replaced by n-butanol (solvent B) by, first, mixing dichloromethane and n-butanol; and, second, distilling off solvent A.

To distill off dichloromethane the mixture of dichloromethane and n-butanol is heated to a temperature of at least 60° C., particularly a temperature of 60-120° C., preferably a temperature of 90-110° C. to give "the compound of formula (I) dissolved in heated n-butanol".

1.4.2 Crystallization of Polymorphic Form B of the Compound of Formula (I)

To give polymorphic form B of the compound of formula (I) the compound of formula (I) dissolved in solvent B, particularly in heated solvent B, preferably in heated n-butanol, is cooled down.

The X-ray powder diffractogram of polymorphic form B of compound (I) is shown in FIG. 1.

In another embodiment of the present invention after the heating of the mixture of solvent A and solvent B and after replacement of the solvent A, preferably dichloromethane, by heated solvent B, preferably by heated n-butanol, heated solvent B, preferably heated n-butanol, is cooled down to 0-30° C.

The expression "after replacement of the solvent A, preferably dichloromethane by solvent B, preferably by n-butanol" particularly means that no solvent A, preferably no dichloromethane, is left, when solvent B, preferably n-butanol is cooled down.

In another embodiment of the present invention after the replacement of the solvent A, preferably dichloromethane, by solvent B, preferably by n-butanol, solvent B is heated to a temperature of at least 60° C., particularly a temperature of 60-120° C., preferably a temperature of 90-110° C., and then is cooled down to 0-30° C.

Preferably solvent B in a first step is cooled down to 15-30° C., preferably to 20-30° C., and in a second step then further cooled down to 0-5° C., preferably to 2-4° C.

In another embodiment of the method according to the present invention for preparing the compound of formula (I) solvent B is cooled down to 0-30° C., preferably to 20-30° C., within 2-36 hours, particularly within 3-24 hours, preferably within 4-12 hours, most preferred within 6-10 hours.

Preferably solvent B, first, within 2-36 hours, particularly within 3-24 hours, preferably within 4-12 hours, most preferred within 6-10 hours is cooled down from a temperature of 60-120° C., preferably a temperature of 90-110° C., to a temperature of 15-30° C., preferably to 20-30° C., and, second, solvent B is then further cooled down to 0-5° C., preferably to 2-4° C. and the temperature is kept constant for at least 0.5 hour, particularly for 0.5-12 hours, preferably for 1-8 hours.

Preferably solvent B,
a) first, within 2-36 hours, particularly within 3-24 hours, preferably within 4-12 hours, most preferred within 6-10 hours is cooled down to 15-30c, preferably to 20-30° C.; and
b) second, the temperature of solvent B is kept constant for at least 0.5 hour, particularly for 1-12 hours, preferably for 1-8 hours, most preferred for 1-2 hours; and
c) third, solvent B within 2-36 hours, particularly within 3-24 hours, preferably within 4-12 hours, most preferred within 6-10 hours is further cooled down to 0-5° C., preferably to 2-4° C.; and
d) fourth, the temperature of solvent B is kept constant for at least 0.5 hour, particularly for 0.5-12 hours, preferably for 0.5-8 hours, most preferred for 0.5-2 hours.

In another embodiment, e.g. to improve the filtration behavior of the suspension, after having cooled down solvent B, particularly cooled down to the temperatures defined above, solvent B is heated again to a temperature of at least 40° C., preferably to a temperature of 60-120° C., preferably to a temperature of 90-110° C. at 60-100° C. again, particularly for a time period of 0.5-10 hours, preferably for 1-4 hours, and is then cooled down again to 0-30° C., preferably to 20-30° C., within 2-36 hours, particularly within 3-24 hours, preferably within 4-12 hours, most preferred within 6-10 hours.

The crystallization of the compound of formula (I) in solvent B, preferably in n-butanol, is performed in per kg of the compound of formula (I) 2-10 kg, preferably 3-6 kg, most preferably in 3.5-5 kg solvent B, preferably n-butanol.

After having cooled down solvent B, particularly according to the cooling procedure described above, polymorphic form B of the compound of formula (I) is obtained in crystalline form.

In another embodiment of the method according to the present invention crystals of the polymorphic form B of the compound of formula (I) are isolated, particularly they are isolated by filtration.

In another embodiment of the method according to the present invention the isolated crystals of the polymorphic form B of the compound of formula (I) can be further purified by dissolving the isolated crystals of the polymorphic form B of the compound of formula (I) in the solvent A, preferably in dichloromethane, and by repeating one or more times, particularly once, the solvent switch described in section 1.4.1 and/or by repeating one or more times, particularly once, the crystallization of polymorphic form B of the compound of formula (I) described in section 1.4.2.

The isolated polymorphic form B of the compound of formula (I) may be further purified, particularly per kg of the polymorphic form B of the compound of formula (I) it may be washed with 1-10 kg, particularly with 1-7 kg, preferably with 1-3 kg n-butanol, preferably with cold n-butanol having a temperature of −5-10° C., prefer ably of −3°-5° C.

The polymorphic form B of the compound of formula (I) may be dried at 35-75° C., preferably at 50-75° C., most preferred at 40-60° C.

The polymorphic form B of the compound of formula (I) may be dried under vacuum at 20-100 mbar, preferably at 30-50 mbar, and under vacuum at 20-100 mbar, preferably at 30-50 mbar and, at temperatures of 35-75° C., preferably under vacuum at 20-100 mbar, preferably at 30-50 mbar and at 50-75° C., most preferred under vacuum at 20-100 mbar, preferably at 30-50 mbar and at 40-60° C.

The crystallization process to obtain polymorphic form B of the compound of formula (I) is very efficient in regard to purity of the compound of formula (I).

2. Synthesis of the Intermediate Compound of Formula (IXa) or (IXb) by Reacting an Intermediate Compound of Formula (VIIIa) or (VIIIb) with a Compound of Formula (VIa) or (VIb)

In accordance with another aspect the present invention covers a method for preparing the compound of formula (IXa) or (IXb) comprising the step of reacting an intermediate compound of formula (VIIIa)

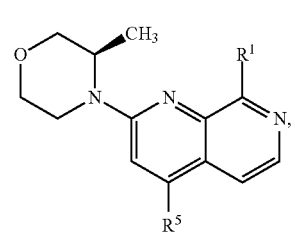

(VIIIa)

in which $R^1$ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy; and $R^5$ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy;

with a compound of formula (VIa)

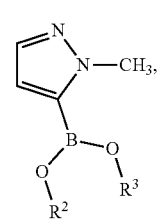

(VIa)

in which $R^2$ and $R^3$ represent, independently from each other, a hydrogen atom or a $C_1$-$C_6$-alkyl group;

or $R^2$ and $R^3$ together represent a —$CH_2$—$CH_2$— group or a —$CH_2$—$CH_2$—$CH_2$— group, wherein said —$CH_2$—$CH_2$— group or —$CH_2$—$CH_2$—$CH_2$— group is optionally substituted one, two, three or four times with a group selected from methyl and ethyl;

or $R^2$ and $R^3$ together represent a group

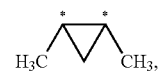

wherein "*" represents the point of attachment to the rest of the molecule;

to give an intermediate compound of formula (IXa)

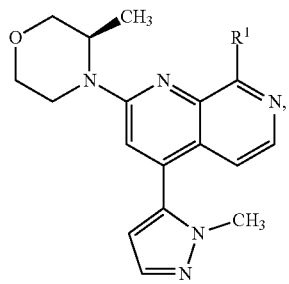

(IXa)

in which R¹ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment of the method according to the present invention for preparing the compound of formula (I) the method further comprises (prior to the reaction of the intermediate compound of formula (IXa) or (IXb) with a compound of formula (IIIa), (IIIb) or (IIIc)) the step of (a) reacting an intermediate compound of formula (VIIIa)

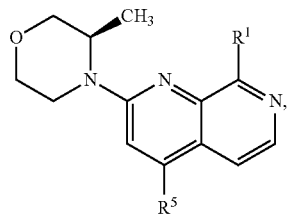

(VIIIa)

in which
R¹ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy; and
R⁵ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy;
with a compound of formula (VIa)

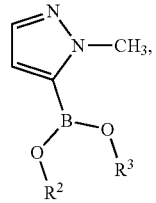

(VIa)

in which
R² and R³ represent, independently from each other, a hydrogen atom or a C₁-C₆-alkyl group;
or
R² and R³ together represent a —CH₂—CH₂— group or a —CH₂—CH₂—CH₂— group, wherein said —CH₂—CH₂— group or —CH₂—CH₂—CH₂— group is optionally substituted one, two, three or four times with a group selected from methyl and ethyl;
or
R² and R³ together represent a group

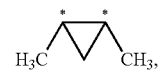

wherein "*" represents the point of attachment to the rest of the molecule;
to give an intermediate compound of formula (IXa)

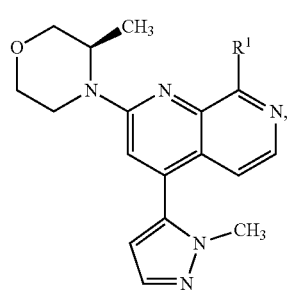

(IXa)

in which R¹ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment of the method according to the present invention, R¹ of the compound of formula (VIIIa) represents a chlorine or bromine atom, preferably a chlorine atom.

In another embodiment of the method according to the present invention, R¹ of the compound of formula (IXa) represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy,

[(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment of the method according to the present invention, $R^1$ of the compound of formula (VIIIa) represents a group selected from [(trifluoromethyl)sulfonyl]oxy, [(nonafluorobutyl)sulfonyl]oxy, (methylsulfonyl)oxy and (p-toluenesulfonyl)oxy.

In another embodiment of the method according to the present invention, $R^5$ of the compound of formula (VIIIa) represents a chlorine, bromine or iodine atom.

In another embodiment of the method according to the present invention, $R^5$ of the compound of formula (IXa) represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In a preferred embodiment of the method according to the present invention, $R^5$ of the compound of formula (VIIIa) represents a [(trifluoromethyl)sulfonyl]oxy group.

In another embodiment of the method according to the present invention, $R^1$ of the compound of formula (VIIIa) represents a chlorine or bromine atom, preferably a chlorine atom, and $R^5$ represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy, preferably a [(trifluoromethyl)sulfonyl]oxy group.

The compound of formula (VIIIa), in which $R^1$ represents a chlorine atom and in which $R^5$ represents a [(trifluoromethyl)sulfonyl]oxy group is (R)-8-chloro-2-(3-methylmorpholino)-1,7-naphthyridin-4-yl trifluoro-methanesulfonate, which is the preferred compound of formula (VIIIb):

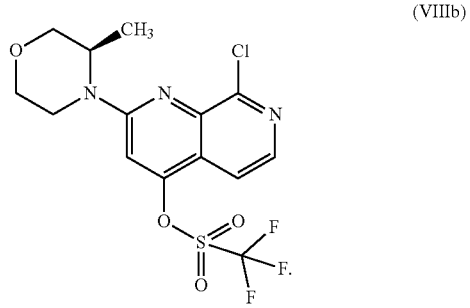 [SMILES: C[C@@H]1COCCN1c1cc(OS(=O)(=O)C(F)(F)F)c2ccnc(Cl)c2n1]

(VIIIb)

In another embodiment of the present invention, $R^2$ and $R^3$ of the compound of formula (VIa) represent, independently from each other, a hydrogen atom or a $C_1$-$C_3$ alkyl group, particularly a methyl or ethyl group.

In another embodiment of the present invention, $R^2$ and $R^3$ of the compound of formula (VIa) together represent a —$CH_2$—$CH_2$— group or a —$CH_2$—$CH_2$—$CH_2$— group, wherein said —$CH_2$—$CH_2$— group or —$CH_2$—$CH_2$— $CH_2$— group is optionally substituted one, two, three or four times with a group selected from methyl and ethyl.

If $R^2$ and $R^3$ of the compound of formula (VIa) together represent a —$CH_2$—$CH_2$— group or a —$CH_2$—$CH_2$—$CH_2$— group, said —$CH_2$—$CH_2$— group or said —$CH_2$—$CH_2$—$CH_2$— group together with the boron atom and the oxygen atoms to which said group is bound forms a 5- or 6-membered ring.

In another embodiment of the present invention, $R^2$ and $R^3$ of the compound of formula (VIa) together represent a group

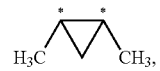

wherein "*" represents the point of attachment to the rest of the molecule.

In another embodiment of the present invention, $R^2$ and $R^3$ of the compound of formula (VIa) together represent a —$C(CH_3)_2$—$C(CH_3)_2$— or a —$CH_2$—$C(CH_3)_2$—$CH_2$— group.

In a preferred embodiment of the present invention, $R^2$ and $R^3$ of the compound of formula (VIa) together represent a —$C(CH_3)_2$—$C(CH_3)_2$— group.

In another embodiment of the present invention, the compound of formula (VIa) is 1-methyl-1H-pyrazole-5-boronic acid.

In a preferred embodiment of the present invention, the compound of formula (VIa) is 1-methyl-1H-pyrazole-5-boronic acid pinacol ester (of formula VIb):

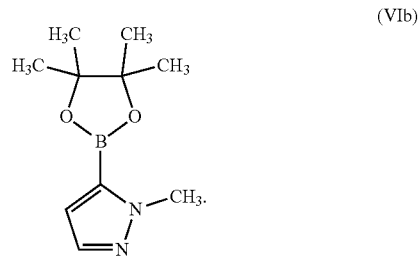

(VIb)

The compounds of formula (VIa) or (VIb) are commercially available or can be synthesized by methods known to the person skilled in the art.

In a preferred embodiment of the present invention, the compound of formula (VIIIa) is (R)-8-chloro-2-(3-methylmorpholino)-1,7-naphthyridin-4-yl trifluoro-methanesulfonate (VIIIb) and the compound of formula (VIa) is 1-methyl-1H-pyrazole-5-boronic acid pinacol ester (VIb).

In another embodiment of the method according to the present invention the intermediate compound of formula (VIIIa) is reacted with 0.7-2.0 molar equivalents of the compound of formula (VIa), preferably with 0.8-1.5 molar equivalents of the compound of formula (VIa), most preferably with 0.9-1.2 molar equivalents of the compound of formula (VIa).

In another embodiment of the method according to the present invention the intermediate compound of formula (VIIIb) is reacted with 0.7-2.0 molar equivalents of the compound of formula (VIb), preferably with 0.8-1.5 molar equivalents of the compound of formula (VIb), most preferably with 0.9-1.2 molar equivalents of the compound of formula (VIb).

In another embodiment of the method according to the present invention the compound of formula (VIa) or (VIb), particularly 1-methyl-1H-pyrazole-5-boronic acid pinacol ester (VIb), is dissolved in a solvent, for example in isopropylacetate, ethyl acetate, 1,2-dimethoxyethane, dioxane, N,N-dimethylformamide (=DMF), 1,2-dimethoxyethane (=DME), tetrahydrofuran (=THF), 2-methyl-tetrahydrofuran (=2-Me-THF) or isopropanol.

In a preferred embodiment of the method according to the present invention the compound of formula (VIa) or (VIb), particularly 1-methyl-1H-pyrazole-5-boronic acid pinacol ester (VIb), is dissolved in isopropyl acetate or ethyl acetate, most preferred is ethyl acetate.

In another embodiment of the method according to the present invention the compound of formula (VIIIa) or (VIIIb) is dissolved in a solvent, for example in isopropylacetate, ethyl acetate, 1,2-dimethoxyethane, dioxane, N,N-dimethylformamide (=DMF), 1,2-dimethoxyethane (=DME), tetrahydrofuran (=THF), 2-methyl-tetrahydrofuran (=2-Me-THF) or isopropanol.

In a preferred embodiment of the method according to the present invention the compound of formula (VIIIa) or (VIIIb), particularly (VIIIa), is dissolved in isopropyl acetate or ethyl acetate, most preferred is ethyl acetate.

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly 1-methyl-1H-pyrazole-5-boronic acid pinacol ester (VIb), is performed in an organic solvent comprising a solvent, which is selected from the group consisting of isopropyl acetate, ethyl acetate, 1,2-dimethoxyethane, 1,4-dioxane, dimethylformamide, tetrahydrofuran, 2-methyltetrahydrofuran and isopropanol; or in a solvent mixture comprising one or more of said organic solvents and water.

In a preferred embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), is performed in a solvent comprising ethyl acetate or isopropyl acetate or in a solvent mixture comprising ethyl acetate and water or isopropyl acetate and water, most preferred is a solvent mixture comprising ethyl acetate and water.

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly 1-methyl-1H-pyrazole-5-boronic acid pinacol ester (VIb), is performed for 1-12 hours, particularly for 1-5 hours, preferably for 1-3 hours, most preferably for 60-90 minutes.

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), is performed in the presence of a suitable catalyst system, like for example a palladium catalyst.

In another embodiment of the method according to the present invention the palladium catalyst is selected from the group consisting of [1,1'-bis(diphenylphosphino)ferrocene]dichloro palladium(II), palladium (II) acetate, bis(triphenylphosphine)palladium(II)dichloride, dichlorobis(tricyclohexylphosphine)palladium(II), (2-dicyclohexylphosphino-2',4',6'-triisopropyl-1,1'-biphenyl)[2-(2-aminoethyl)phenyl)]palladium(II)chloride, chloro (2-dicyclohexylphosphino-2',4',6'-triisopropyl-1,1'-biphenyl)[2-(2'-amino-1,1'-biphenyl)]palladium(II), tetrakis (triphenylphosphine)palladium(0), bis(tri-tert-butylphosphine)palladium(0), bis[tris(2-methylphenyl)phosphine]palladium(0), tris(dibenzylideneacetone)dipalladium(0).

In a preferred embodiment of the method according to the present invention the palladium catalyst is [1,1'-bis(diphenylphosphino)ferrocene]dichloro palladium(II).

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), is performed in the presence of 0.001-0.1 molar equivalents, preferably of 0.005-0.05 molar equivalents, most preferably of 0.0-0.03 molar equivalents of the palladium catalyst, preferably of [1,1'-bis(diphenylphosphino)ferrocene]dichloro palladium(II).

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), is performed in the presence of a base. Bases like potassium phosphate, potassium carbonate, potassium hydrogen carbonate, sodium phosphate, sodium carbonate, sodium hydrogen carbonate, barium hydroxide, barium carbonate, cesium carbonate or lithium carbonate can be used. Potassium carbonate or potassium hydrogen carbonate are preferred, most preferred is potassium hydrogen carbonate.

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), is performed in the presence of 1-15 molar equivalents, preferably of 2-8 molar equivalents, most preferably of 3-5 or 3.5-4.5 molar equivalents of base.

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), is performed at temperatures ranging from room temperature to the boiling point of the solvent.

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5- boronic acid pinacol ester (VIb), is performed under pressure at temperatures above the boiling point.

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), is performed in isopropyl acetate or in isopropyl acetate and water at a temperature of 35-75° C., preferably at 40-60° C., most preferably at 45-55° C.

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), is performed in ethyl acetate or in ethyl acetate and water, preferably in ethyl acetate and water, at a temperature of 30-60° C., preferably at 35-50° C., most preferably at 38-45° C.

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), is performed under inert gas atmosphere, wherein the inert gas is nitrogen or argon, preferably nitrogen.

2.1 Further Processing of the Crude Compound of Formula (IXa) or (IXb) and Crystallization of the Compound of Formula (IXa) or (IXb)

In another embodiment of the method according to the present invention the reaction of the intermediate compound of formula (VIIIa) or (VIIIb), particularly of (R)-8-chloro-2-(3-methylmorpholino)-1,7-naphthyridin-4-yl trifluoromethanesulfonate (VIIIb), with a compound of formula (VIa) or (VIb), particularly with 1-methyl-1H-pyrazole-5-boronic acid pinacol ester (VIb), the organic solvent or solvent mixture, particularly ethyl acetate with/without water, or isopropyl acetate with/without water, is optionally
  a) washed with an aqueous solution of a base selected from potassium hydroxide, potassium carbonate, potassium hydrogen carbonate, potassium hydroxide, potassium tert-butoxide, sodium hydroxide, sodium phosphate, sodium carbonate, sodium hydroxide, sodium tert-butoxide, barium hydroxide, cesium carbonate, triethylamine; preferably with potassium hydroxide; and/or, optionally,
  b) washed with water; and/or optionally
  c) treated with an adsorbent; preferably the adsorbent is activated activated charcoal; and/or optionally
  d) the adsorbent, particularly the activated charcoal, is filtered;
to give a solution of the compound of formula (IXa) or (IXb) in said organic solvent or solvent mixture, preferably a solution of the compound of formula (IXa) or (IXb) in ethyl acetate or in isopropyl acetate, most preferred in ethyl acetate.

In another embodiment of the method according to the present invention the solvent or the solvent mixture of said solution of the compound of formula (IXa) or (IXb), preferably ethyl acetate or isopropyl acetate, most preferred ethyl acetate, is replaced by another solvent (solvent C in the following). Solvent C comprises a solvent selected from methanol, ethanol, n-propanol, n-butanol, 2-butanol, isopropanol, preferably the solvent is replaced by isopropanol.

Crystallization of the compound of formula (IXa) or (IXb) preferably is performed in solvent C, preferably in isopropanol.

The crystallization of the compound of formula (IXa) or (IXb) in solvent C, preferably in isopropanol, is performed in per kg of the compound of formula (IXa) or (IXb) 2-20 kg, preferably in 2.5-10 kg, most preferably in 2.5-6 kg solvent C, preferably isopropanol, and can then be isolated.

The isolated compound of formula (IXa) or (IXb) may be dried at 35-75° C., preferably at 40-65° C., most preferred at 45-55° C.

The isolated compound of formula (IXa) or (IXb) may be dried under vacuum at 20-100 mbar, preferably at 30-50 mbar, and under vacuum at 20-100 mbar, preferably at 30-50 mbar and, at temperatures of 35-75° C., preferably under vacuum at 20-100 mbar, preferably at 30-50 mbar and at 50-75° C., most preferred under vacuum at 20-100 mbar, preferably at 30-50 mbar and at 40-60° C.

3. Synthesis of the Intermediate Compound of Formula (VIIIa) or (VIIIb) Starting from the Compound of Formula (II) or (IIa)

In accordance with another aspect the present invention covers a method for preparing the compound of formula (VIIIa) comprising the step of reacting an intermediate compound of formula (II)

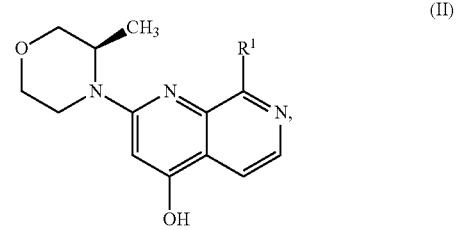

(II)

in which $R^1$ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy;

with a compound selected from N-phenyl-bis(trifluoromethanesulfonimide, trifluoromethanesulfonic anhydride, methanesulfonic acid chloride, p-toluenesulfonyl chloride, nonafluorobutanesulfonyl chloride, nonafluorobutanesulfonyl fluoride, benzenesulfonyl chloride, 4-bromobenzenesulfonyl chloride, 4-nitrobenzenesulfonyl chloride, 2-nitrobenzenesulfonyl chloride, 4-isopropylbenzenesulfonyl chloride, 2,4,6-triisopropylbenzenesulfonyl chloride, 2-mesitylenesulfonyl chloride (=2,4,6-trimethylbenzenesulfonyl chloride), 4-tert-butylbenzenesulfonyl chloride and 4-methoxybenzenesulfonyl chloride;

to give an intermediate compound of formula of formula (VIIIa)

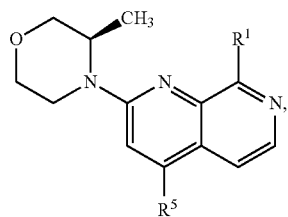

in which
R¹ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy;

$R^5$ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment of the method according to the present invention for preparing the compound of formula (I) the method further comprises (prior to the reaction of the intermediate compound of formula (VIIIa) or (VIIIb) with a compound of formula (VIa) or (VIb)) the step of reacting an intermediate compound of formula (II)

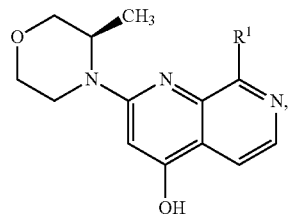

in which
R¹ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy;
with a compound selected from N-phenyl-bis(trifluoromethanesulfonimide, trifluoromethanesulfonic anhydride, methanesulfonic acid chloride, p-toluenesulfonyl chloride, nonafluorobutanesulfonyl chloride, nonafluorobutanesulfonyl fluoride, benzenesulfonyl chloride, 4-bromobenzenesulfonyl chloride, 4-nitrobenzenesulfonyl chloride, 2-nitrobenzenesulfonyl chloride, 4-isopropylbenzenesulfonyl chloride, 2,4,6-triisopropylbenzenesulfonyl chloride, 2-mesitylenesulfonyl chloride (=2,4,6-trimethylbenzenesulfonyl chloride), 4-tert-butylbenzenesulfonyl chloride and 4-methoxybenzenesulfonyl chloride;

to give an intermediate compound of formula of formula (VIIIa)

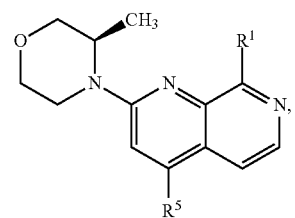

in which
R¹ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy;

$R^5$ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment of the method according to the present invention, R¹ of the compound of formula (II) represents a chlorine or bromine atom, preferably a chlorine atom. The compound of formula (II), in which R¹ represents a chlorine atom is the preferred compound of formula (IIa) (=(R)-8-chloro-2-(3-methylmorpholino)-1,7-naphthyridin-4-ol):

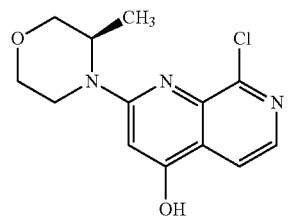

In another embodiment of the method according to the present invention, R¹ of the compound of formula (II)

represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment of the method according to the present invention, R$^1$ of the compound of formula (II) represents a group selected from [(trifluoromethyl)sulfonyl]oxy, [(nonafluorobutyl)sulfonyl]oxy, (methylsulfonyl)oxy and (p-toluenesulfonyl)oxy.

In another embodiment of the method according to the present invention, R$^1$ of the compound of formula (VIIIa) represents a chlorine or bromine atom, preferably a chlorine atom.

In another embodiment of the method according to the present invention, R$^1$ of the compound of formula (VIIIa) represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment of the method according to the present invention, R$^1$ of the compound of formula (VIIIa) represents a group selected from [(trifluoromethyl)sulfonyl]oxy, [(nonafluorobutyl)sulfonyl]oxy, (methylsulfonyl)oxy and (p-toluenesulfonyl)oxy.

In another embodiment of the method according to the present invention, R$^5$ of the compound of formula (VIIIa) represents a chlorine, bromine or iodine atom.

In another embodiment of the method according to the present invention, R$^5$ of the compound of formula (IXa) represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In a preferred embodiment of the method according to the present invention, R$^5$ of the compound of formula (VIIIa) represents a [(trifluoromethyl)sulfonyl]oxy group.

In another embodiment of the method according to the present invention, R$^1$ of the compound of formula (VIIIa) represents a chlorine or bromine atom, preferably a chlorine atom, and R$^5$ represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy, preferably a [(trifluoromethyl)sulfonyl]oxy group.

The compound of formula (VIIIa), in which R$^1$ represents a chlorine atom and in which R$^5$ represents a [(trifluoromethyl)sulfonyl]oxy group is (R)-8-chloro-2-(3-methylmorpholino)-1,7-naphthyridin-4-yl trifluoro-methanesulfonate, which is the preferred compound of formula (VIIIb):

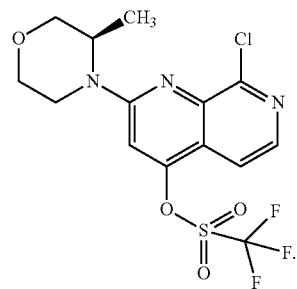

In a preferred embodiment of the present invention, the compound of formula (II) is (R)-8-chloro-2-(3-methylmorpholino)-1,7-naphthyridin-4-ol (IIa) and the compound of formula (VIIIa) is (R)-8-chloro-2-(3-methylmorpholino)-1,7-naphthyridin-4-yl trifluoro-methanesulfonate (VIIIb).

In another embodiment of the method according to the present invention the intermediate compound of formula (II), preferably the compound of formula (IIa), is reacted with 0.8-2.0, preferably with 0.9-1.7, most preferably with 1.0-1.5 molar equivalents of a compound selected from N-phenyl-bis(trifluoromethanesulfonimide, trifluoromethanesulfonic anhydride, methanesulfonic acid chloride, p-toluenesulfonyl chloride, nonafluorobutanesulfonyl chloride, nonafluorobutanesulfonyl fluoride, benzenesulfonyl chloride, 4-bromobenzenesulfonyl chloride, 4-nitrobenzenesulfonyl chloride, 2-nitrobenzenesulfonyl chloride, 4-isopropylbenzenesulfonyl chloride, 2,4,6-triisopropylbenzenesulfonyl chloride, 2-mesitylenesulfonyl chloride (=2,4,6-trimethylbenzenesulfonyl chloride), 4-tert-butylbenzenesulfonyl chloride and 4-methoxybenzenesulfonyl chloride.

Preferably the compound of formula (IIa) is reacted with 0.8-2.0, preferably with 0.9-1.7, most preferably with 1.0-1.5 molar equivalents of trifluoromethanesulfonic anhydride or N-phenyl-bis(trifluoromethanesulfonimide, most preferred with 0.8-2.0, preferably with 0.9-1.7, most preferably with 1.0-1.5 molar equivalents trifluoromethanesulfonic anhydride.

In another embodiment of the method the aforementioned reaction is performed in an aprotic solvent like dichloromethane, tetrahydrofuran, pyridine, ethylacetate, isopropylacetate, acetonitrile, 2-methyl-tetrahydrofuran, 1,4-dioxane, 1,2-dimethoxyethane, acetone, 2-butanone, butyl acetate, cyclopentyl methyl ether, methyl tert.-butylether, toluene, propionitrile, chlorobenzene, anisole, chloroform, the preferred solvent is dichloromethane.

Per kg of compound of formula (II) or (IIa) 4-20 kg of solvent is used, preferably 6-15 kg of solvent, most preferably 7-9 kg of solvent, preferably of dichloromethane.

In another embodiment the reaction of the intermediate compound of formula (II) with a compound selected from N-phenyl-bis(trifluoromethanesulfonimide, trifluoromethanesulfonic anhydride, methanesulfonic acid chloride, p-toluenesulfonyl chloride, nonafluorobutanesulfonyl chloride, nonafluorobutanesulfonyl fluoride, benzenesulfonyl chloride, 4-bromobenzenesulfonyl chloride, 4-nitrobenzenesulfonyl chloride, 2-nitrobenzenesulfonyl chloride, 4-isopropylbenzenesulfonyl chloride, 2,4,6-triisopropylbenzenesulfonyl chloride, 2-mesitylenesulfonyl chloride (=2,4,6-trimethylbenzenesulfonyl chloride), 4-tert-butylbenzenesulfonyl chloride and 4-methoxybenzenesulfonyl chloride, preferably with trifluoromethanesulfonic anhydride or N-phenyl-bis(trifluoromethanesulfonimide, is performed in the presence of a base, particularly of an organic base or of an inorganic base or of mixtures of one or more organic base(s) with one or more inorganic base(s).

Organic bases such as pyridine, N,N-diethylethanamine (=triethylamine), N,N-di(propan-2-yl)propan-2-amine (=triisopropylamine), N,N-dibutylbutan-1-amine (=tributylamine), 2,6-dimethylpyridine (=2,6 lutidine), —N-ethyl-N-(propan-2-yl)propan-2-amine (=N,N-diisopropylethylamine or Huenig's base), N-methyl morpholine can be used for the aforementioned reaction. Preferred bases are N,N-diethylethanamine (=triethylamine) and pyridine, most preferred is pyridine.

The use of pyridine is particularly advantageous to avoid unwanted discoloration of the compound of formula (VIIIa) or (VIIIb).

Inorganic bases, which can be used for the aforementioned reaction, are for example potassium carbonate, potassium hydrogen carbonate, sodium phosphate, sodium carbonate, sodium hydrogen carbonate, calcium carbonate, calcium hydrogen carbonate, or cesium carbonate.

In another embodiment of the method according to the present invention the intermediate compound of formula (II), preferably the compound of formula (IIa), is reacted with a compound selected from N-phenyl-bis(trifluoromethanesulfonimide, trifluoromethanesulfonic anhydride, methanesulfonic acid chloride, p-toluenesulfonyl chloride, nonafluorobutanesulfonyl chloride, nonafluorobutanesulfonyl fluoride, benzenesulfonyl chloride, 4-bromobenzenesulfonyl chloride, 4-nitrobenzenesulfonyl chloride, 2-nitrobenzenesulfonyl chloride, 4-isopropylbenzenesulfonyl chloride, 2,4,6-triisopropylbenzenesulfonyl chloride, 2-mesitylenesulfonyl chloride (=2,4,6-trimethylbenzenesulfonyl chloride), 4-tert-butylbenzenesulfonyl chloride and 4-methoxybenzenesulfonyl chloride, preferably with trifluoromethanesulfonic anhydride or N-phenyl-bis(trifluoromethanesulfonimide, in the presence of 0.7-4.0, preferably of 0.9-3.0, most preferably of 1.0-2.0 molar equivalents of the base, preferably of N,N-diethylethanamine or pyridine, most preferred of pyridine.

In a preferred embodiment of the method according to the present invention the intermediate compound of formula (II), preferably the compound of formula (IIa), is reacted with trifluoromethanesulfonic anhydride in the presence of 0.7-4.0, preferably of 0.9-3.0, most preferably with 1.0-2.0 molar equivalents of pyridine.

In another embodiment of the method according to the present invention the reaction of the intermediate compound of formula (II) with a compound selected from N-phenyl-bis(trifluoromethanesulfonimide, trifluoromethanesulfonic anhydride, methanesulfonic acid chloride, p-toluenesulfonyl chloride, nonafluorobutanesulfonyl chloride, nonafluorobutanesulfonyl fluoride, benzenesulfonyl chloride, 4-bromobenzenesulfonyl chloride, 4-nitrobenzenesulfonyl chloride, 2-nitrobenzenesulfonyl chloride, 4-isopropylbenzenesulfonyl chloride, 2,4,6-triisopropylbenzenesulfonyl chloride, 2-mesitylenesulfonyl chloride (=2,4,6-trimethylbenzenesulfonyl chloride), 4-tert-butylbenzenesulfonyl chloride and 4-methoxybenzenesulfonyl chloride, preferably with trifluoromethanesulfonic anhydride or N-phenyl-bis(trifluoromethanesulfonimide, is performed at temperatures of −30-30° C., preferably of −20-20° C., most preferred at −15 to 0° C. The reaction time can be 1 to 24 hours, preferred time is 1-4 hours.

In a preferred embodiment of the method according to the present invention the intermediate compound of formula (II), preferably the compound of formula (IIa), is reacted with trifluoromethanesulfonic anhydride in the presence of 0.7-4.0, preferably of 0.9-3.0, most preferably with 1.0-2.0 molar equivalents of pyridine at temperatures of −30-30° C., preferably of −20-5° C., most preferred at −15 to −5° C. The reaction time can be 1 to 24 hours, preferred time is 1-4 hours.

3.1 Further Processing of the Crude Compound of Formula (VIIIa) or (VIIIb) and Crystallization of the Compound of Formula (VIIIa) or (VIIIb)

In another embodiment of the method according to the present invention the reaction of the intermediate compound of formula (II) with a compound selected from N-phenyl-bis(trifluoromethanesulfonimide, trifluoromethanesulfonic anhydride, methanesulfonic acid chloride, p-toluenesulfonyl chloride, nonafluorobutanesulfonyl chloride, nonafluorobutanesulfonyl fluoride, benzenesulfonyl chloride, 4-bromobenzenesulfonyl chloride, 4-nitrobenzenesulfonyl chloride, 2-nitrobenzenesulfonyl chloride, 4-isopropylbenzenesulfonyl chloride, 2,4,6-triisopropylbenzenesulfonyl chloride, 2-mesitylenesulfonyl chloride (=2,4,6-trimethylbenzenesulfonyl chloride), 4-tert-butylbenzenesulfonyl chloride and 4-methoxybenzenesulfonyl chloride, preferably with trifluoromethanesulfonic anhydride or N-phenyl-bis(trifluoromethanesulfonimide, the organic solvent or solvent mixture, particularly dichloromethane, is optionally
   a) washed with water; and/or, optionally
   b) washed with an aqueous solution of a base selected from potassium hydroxide, potassium carbonate, potassium hydrogen carbonate, potassium hydroxide, potassium tert-butoxide, sodium hydroxide, sodium phosphate, sodium carbonate, sodium hydroxide, sodium tert-butoxide, barium hydroxide, cesium carbonate, triethylamine; preferably with aqueous potassium carbonate; and/or, optionally,
   c) after the wash with the aqueous solution of a base is washed again with water;
   d) treated with an adsorbent; preferably the adsorbent is activated charcoal; and/or optionally
   e) the adsorbent, particularly the activated charcoal, is filtered;
to give a solution of the compound of formula (VIIIa) or (VIIIb) in said organic solvent or solvent mixture, preferably a solution of the compound of formula (VIIIa) or (VIIIb) in dichloromethane.

The sequence of the further processing of the crude compound of formula (VIIIa) or (VIIIb) according to steps a) (washing with water), b) (washing with an aqueous solution of a base), c) (washing with water after washing with an aqueous solution of a base), d) (treatment with an adsorbent) and/or e) (filtration of the adsorbent), as described supra, can be changed. For example steps d) and e) can be performed prior to steps a), b) and c).

In another embodiment of the method according to the present invention the solvent or the solvent mixture of said solution of the compound of formula (VIIIa) or (VIIIb), preferably dichloromethane, is replaced by another solvent (solvent D in the following). Solvent D comprises a solvent selected from methanol, ethanol, n-propanol, n-butanol, 2-butanol, isopropanol, preferably the solvent is replaced by isopropanol.

In a preferred embodiment of the method according to the present invention the reaction of the intermediate compound of formula (II) with a compound selected from N-phenyl-bis(trifluoromethanesulfonimide, trifluoromethanesulfonic anhydride, methanesulfonic acid chloride, p-toluenesulfonyl chloride, nonafluorobutanesulfonyl chloride, nonafluorobutanesulfonyl fluoride, benzenesulfonyl chloride, 4-bromobenzenesulfonyl chloride, 4-nitrobenzenesulfonyl chloride, 2-nitrobenzenesulfonyl chloride, 4-isopropylbenzenesulfonyl chloride, 2,4,6-triisopropylbenzenesulfonyl chloride, 2-mesitylenesulfonyl chloride (=2,4,6-trimethylbenzenesulfonyl chloride), 4-tert-butylbenzenesulfonyl chloride and 4-methoxybenzenesulfonyl chloride is performed under inert gas atmosphere, wherein the inert gas is nitrogen or argon, preferably nitrogen.

Crystallization of the compound of formula (VIIIa) or (VIIIb) preferably is performed in solvent D, preferably in isopropanol.

Per kg of compound of formula (VIIIa) or (VIIIb) 2-6 kg of the organic solvent, preferably 3-5 kg of the organic solvent, most preferably 3-4 kg of the organic solvent, preferably of isopropanol, is used.

The product can be for example isolated by filtration or by centrifuge. It can be dried at 25-60° C., preferably at 40-50° C. It can be dried for 1-24 hours, preferably 8-15 hours, most preferably 10-14 hours.

The processing of the crude compound of formula (VIIIa) or (VIIIb) and its subsequent crystallization from isopropanol yielded the compound of formula (VIIIa) or (VIIIb) in high purity and in 64-87.7% of the theoretical yield, without using any chromatographic purification step. The reaction to give the compound of formula (VIIIa) or (VIIIb) can be performed in larger scales (e.g. multi-kg scale). The purities of the product obtained was very high (e.g. >98% (UHPLC, area %)).

4. Intermediate Compounds of Formula (IXa) or (IXb)

In accordance with another aspect, the present invention covers the intermediate compound of formula (IXa)

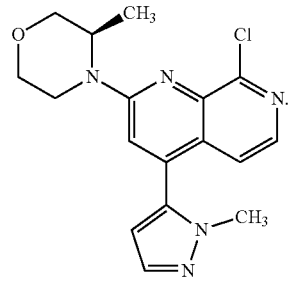

(IXa)

in which
R¹ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment the present invention relates to the intermediate compound of formula (IXa), in which R¹ represents a chlorine or bromine atom, preferably a chlorine atom.

In another embodiment the present invention relates to the intermediate compound of formula (IXa), in which R¹ represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment the present invention relates to the intermediate compound of formula (IXa), in which R¹ represents a group selected from [(trifluoromethyl)sulfonyl]oxy, [(nonafluorobutyl)sulfonyl]oxy, (methylsulfonyl)oxy and (p-toluenesulfonyl)oxy.

In a preferred embodiment, the present invention relates to the compound of formula (IXb):

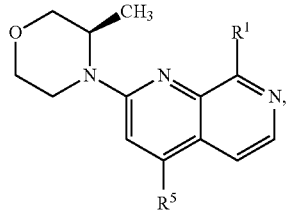

(IXb)

5. Intermediate Compounds of Formula (VIIIa) or (VIIIb)

In accordance with another aspect, the present invention covers the intermediate compound of formula (VIIIa)

(VIIIa)

in which
R¹ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy; and
R⁵ represents a chlorine, bromine or iodine atom or represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment the present invention relates to the intermediate compound of formula (VIIIa), in which R¹ represents a chlorine or bromine atom, preferably a chlorine atom.

In another embodiment the present invention relates to the intermediate compound of formula (VIIIa), in which $R^1$ represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In another embodiment the present invention relates to the intermediate compound of formula (VIIIa), in which $R^1$ represents a group selected from [(trifluoromethyl)sulfonyl]oxy, [(nonafluorobutyl)sulfonyl]oxy, (methylsulfonyl)oxy and (p-toluenesulfonyl)oxy.

In another embodiment the present invention relates to the intermediate compound of formula (VIIIa), in which $R^5$ represents a chlorine, bromine or iodine atom.

In another embodiment the present invention relates to the intermediate compound of formula (VIIIa), in which $R^5$ represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

In a preferred embodiment the present invention relates to the intermediate compound of formula (VIIIa), in which $R^5$ represents a [(trifluoromethyl)sulfonyl]oxy group.

In another embodiment the present invention relates to the intermediate compound of formula (VIIIa), in which $R^1$ represents a chlorine or bromine atom, preferably a chlorine atom, and in which $R^5$ represents a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy, preferably a [(trifluoromethyl)sulfonyl]oxy group.

In a most preferred embodiment the present invention relates to the intermediate compound of formula (VIIIa), in which $R^1$ represents a chlorine atom and in which $R^5$ represents a [(trifluoromethyl)sulfonyl]oxy group, to give the compound of formula (VIIIb) (=(R)-8-chloro-2-(3-methylmorpholino)-1,7-naphthyridin-4-yl trifluoro-methanesulfonate):

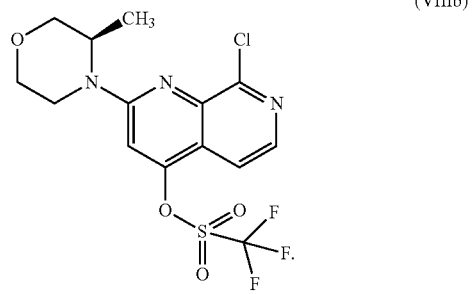

(VIIIb)

6. Polymorphic Form B of the Compound of Formula (I) with High Purity

The method for preparing the compound of formula (I) described in WO2016020320A1 results in polymorphic form B of the compound of formula (I). However, several attempts to up-scale this method to obtain polymorphic form B of the compound of formula (I) with a purity grade, which is acceptable for pharmaceutical uses, were not successful. Further, when trying to up-scale the method described in WO2016020320A1, the resulting product of the compound of formula (I) contained more than 0.15% of one or more side products, for example it contained more than 0.15% of the following compound:

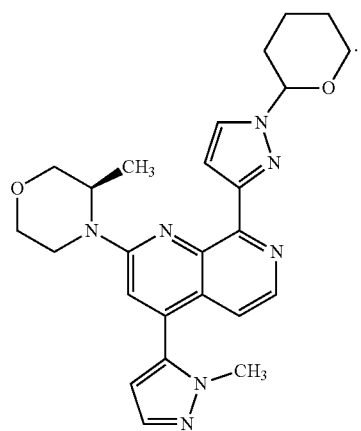

In contrast, the method for preparing the compound of formula (I) according to the present invention now provides polymorphic form B of the compound of formula (I) with a sufficiently high purity grade. The purity of the obtained batches (in the lab, kg lab and pilot plant) is very high. All the individual byproducts are known and had been specified and toxicologically characterized. Palladium (Pd) in the final drug substance was found to be always <10 ppm. Also boron (B) was less than 10 ppm.

In accordance with a further aspect, the present invention therefore covers polymorphic form B of the compound of formula (I), which is obtainable by the method for preparing the compound of formula (I) according to the invention, particularly by the processing method described in section 1.3. ("Further processing of the crude compound of formula (I)") in combination with the crystallization method described in section 1.4. ("Crystallization of the crude compound of formula (I) to give its polymorphic form B").

In another embodiment the polymorphic form B of the compound of formula (I) according to the present invention is characterized by a purity of at least 99.6% (=area %), particularly of at least 99.7% (=area %), preferably of at least 99.8% (=area %), most preferably of at least 99.9% (=area %) measured by UHPLC.

In another embodiment the present invention covers the polymorphic form B of the compound of formula (I) (=2-[(3R)-3-methylmorpholin-4-yl]-4-(1-methyl-1H-pyrazol-5-yl)-8-(1H-pyrazol-5-yl)-1,7-naphthyridine), which is characterized by a purity of at least 99.6% (=area %) particularly of at least 99.7% (=area %), preferably of at least 99.8% (=area %), most preferred of at least 99.9% (=area %) measured by UHPLC.

The purity of the polymorphic form B of the compound of formula (I) is determined by UHPLC, preferably by the method described in the Experimental Section—General Part ("UHPLC—method for the determination of the chemical purity and the assay of the compound of formula (I)").

The purity in "area %" is calculated as the percentage of the UHPLC peak area under the UHPLC peak of polymorphic form B of the compound of formula (I) in relation to total peak area of all UHPLC peaks.

Polymorphic form B of the compound of formula (I) is further characterized by a X-ray powder diffractogram (XRPD), which displays at least 3, particularly at least 5, preferably at least 7, more preferably at least 10, most preferably at least 12 of the following reflections, quoted as 2θ values: 8.3, 9.3, 13.8, 14.0, 18.0, 18.7, 19.6, 19.9, 20.1, 22.1, 23.9, 27.4.

In another embodiment polymorphic form B of the compound of formula (I) is further characterized by a X-ray powder diffractogram (XRPD) comprising the following reflections, quoted as 2θ values: 8.3, 18.0, 19.9.

In another embodiment polymorphic form B of the compound of formula (I) is further characterized by a X-ray powder diffractogram (XRPD) comprising the following reflections, quoted as 2θ values: 8.3, 9.3, 18.0, 19.9, 20.1.

In another embodiment polymorphic form B of the compound of formula (I) is further characterized by a X-ray powder diffractogram (XRPD) comprising the following reflections, quoted as 2θ values: 8.3, 9.3, 13.8, 14.0, 18.0, 19.9, 20.1.

In another embodiment polymorphic form B of the compound of formula (I) is further characterized by the X-ray powder diffractogram (XRPD) substantially as shown in FIG. 1.

In another embodiment form B of the compound of formula (I) is characterized by the X-ray powder diffractogram (XRPD) described in Table A1 (see Experimental Section—General Part).

In another embodiment the present invention covers the polymorphic form B of the compound of formula (I), which is characterized by the X-ray powder diffractogram (XRPD) comprising the above-defined reflections, quoted as 2θ values, and which is further characterized by a purity of at least 99.6% (=area %), particularly of at least 99.7% (=area %), preferably of at least 99.8% (=area %), most preferably of at least 99.9% (=area %) measured by UHPLC.

In another embodiment the present invention covers the polymorphic form B of the compound of formula (I), which is characterized by a purity of at least 99.6% (=area %), particularly of at least 99.7% (=area %), preferably of at least 99.8% (=area %), most preferably of at least 99.9% (=area %) measured by UHPLC, wherein the polymorphic form B of the compound of formula (I) comprises
  a) less than 15 mg boron measured by ICP-MS, preferably less than 10 mg boron, per kg of polymorphic form B of the compound of formula (I); and/or
  b) less than 0.4 mg palladium measured by ICP-MS, preferably 0.3 mg palladium or less than 0.3 mg palladium; and/or
  c) less than 0.05% (=area %) of the compound of formula (IXb) measured by UHPLC; and/or
  d) less than 0.05% (=area %) of the compound of formula (VIb) measured by UHPLC; and/or
  e) less than 0.05% (=area %) of dihydropyrane measured by UHPLC; and/or
  f) less than 0.05% (=area %) of the compound of formula (IIIc) measured by UHPLC; and/or
  g) less than 0.05% (=area %) of pinacol measured by GC; and/or
  h) less than 0.05% (=area %) of the compound of formula (VIIc/VIId) measured by UHPLC; and/or
  i) less than 0.05% (=area %) of the compound of formula

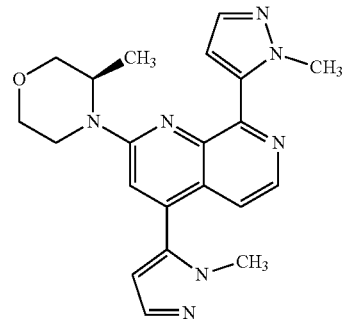 [SMILES: CN/C(=C\C=N)c1cc(N2CCOC[C@H]2C)nc2c(-c3ccnn3C)nccc12]

measured by UHPLC; and/or j) less than 0.05% (=area %) of the compound of formula

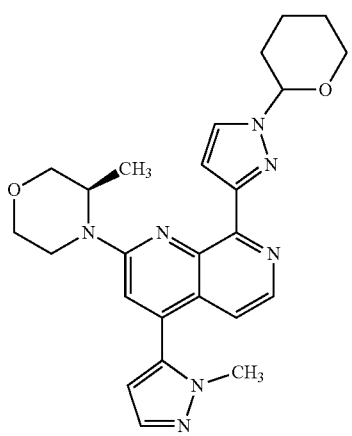

measured by UHPLC.

The boron and/or palladium content of the compound of formula (I) is determined by ICP-MS, preferably by the method described in the Experimental Section—General Part ("ICP-MS—method for the determination of the sum of elements, boron, palladium, iron, potassium, sodium").

The content of the compounds of formulas (IXb), (VIb), (IIIc), (VIIc/VIId), dihydropyrane,

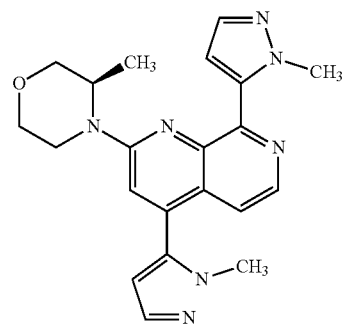 [SMILES: CN/C(=C\C=N)c1cc(N2CCOC[C@H]2C)nc2c(-c3ccnn3C)nccc12]

or is determined by UHPLC, preferably by the method described in the Experimental Section—General Part ("UHPLC—method for the determination of the chemical purity and the assay of the compound of formula (I)").

The pinacol content is determined by GC, preferably by the method described in the Experimental Section—General Part ("GC—method for the determination of pinacol").

In accordance with a further aspect, the present invention covers a pharmaceutical composition, in particular a medicament, comprising polymorphic form B of the compound of formula (I) according to the present invention, which is characterized by a purity of at least 99.6% (=area %) particularly of at least 99.7% (=area %), preferably of at least 99.8% (=area %), most preferred of at least 99.9% (=area %) measured by UHPLC, and one or more excipients, in particular one or more pharmaceutically suitable excipient(s).

Conventional procedures for preparing such pharmaceutical compositions in appropriate dosage forms can be utilized.

It is possible for the compound of formula (I) according to the invention to have systemic and/or local activity. For this purpose, it can be administered in a suitable manner, such as, for example, via the oral, parenteral, pulmonary, nasal, sublingual, lingual, buccal, rectal, vaginal, dermal, transdermal, conjunctival, optic route or as an implant or stent.

For these administration routes, it is possible for the compound of formula (I) according to the invention to be administered in suitable administration forms.

For oral administration, it is possible to formulate the compound of formula (I) according to the invention to dosage forms known in the art that deliver the compound of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compound of formula (I) according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compound of formula (I) according to the invention can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides, fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®), alginates, gelatine),
- disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)),
- flow regulators, lubricants, glidants and mould release agents (for example magnesium stearate, stearic acid, talc, highly-disperse silicas (such as, for example, Aerosil®)),
- coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and block copolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

EXPERIMENTAL SECTION

NMR peak forms are stated as they appear in the spectra, possible higher order effects have not been considered.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations
The following table lists the abbreviations used herein.

| Abbreviation | Meaning |
|---|---|
| aq. | aqueous |
| br | broad ($^1$H-NMR signal) |
| cat. | catalytic |
| conc. | concentrated |
| CI | chemical ionisation |
| d | doublet |
| DAD | diode array detector |
| DCM | dichloromethane |
| dd | double-doublet |
| DIC | N,N'-diisopropylcarbodiimide |
| DIPEA | diisopropylethylamine |
| DMA | N,N-dimethylacetamide |
| DMF | N,N-dimethylformamide |
| DMSO | dimethylsulfoxide |
| dt | double-triplet |
| EtOAc | ethyl acetate |
| EtOH | ethanol |
| equiv. | equivalent |
| ESI | electrospray (ES) ionisation |
| GC | gas chromatography |

TABLE 1-continued

Abbreviations
The following table lists the abbreviations used herein.

| Abbreviation | Meaning |
|---|---|
| h | hour(s) |
| HCl | hydrochloric acid |
| HPLC | high performance liquid chromatography |
| IC | ion Chromatography |
| ICP or ICP-MS | inductively coupled plasma mass spectrometry |
| LC-MS or LCMS | liquid chromatography mass spectrometry |
| L | liter |
| m | multiplet |
| mL | milliliter |
| min | minute(s) |
| MeOH | methanol |
| Mod B | polymorphic form B |
| MS | mass spectrometry |
| n-butanol | 1-butanol |
| n.d. | not detected |
| NMR | nuclear magnetic resonance spectroscopy: chemical shifts (δ) are given in ppm. |
| n.n. | not found |
| n-propanol | 1-propanol |
| Pd/C | palladium on activated charcoal |
| PdCl$_2$(dppf) | [1,1'-bis(diphenylphosphino)ferrocene]dichloro palladium(II) |
| Pd(dba)$_2$ | bis(dibenzylideneacetone)palladium |
| Ph. Eur. | European Pharmacopoeia |
| q | quartet |
| qNMR | quantitative NMR |
| r.t. or rt or RT | room temperature |
| rac | racemic |
| Rt | retention time (as measured either with HPLC or UPLC) in minutes |
| RRT | relative retention time |
| S | singlet |
| sat. | saturated |
| t | triplet |
| td | triple-doublet |
| THF | tetrahydrofuran |
| UHPLC | ultra high performance liquid chromatography |
| USP | United States Pharmacopoeia |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

Analytical Methods and Equipment $^1$H-NMR spectra were recorded in CDCl$_3$, DMSO-d6 or D$_2$O using a Bruker Biospin NMR apparatus with a 400 MHz magnet, chemical shifts (δ) are reported versus TMS as internal standard.

HPLC Chromatograms

HPLC Method Scan base: Agilent system (1260 Binary Pump, G1312B, degasser; autosampler, ColCom, DAD detector: Agilent G1315C, 220-320 nm) Column: Waters XSelect™ CSH (50×2.1 mm 3.5 μm); Column temp 35° C.; Flow 0.8 mL/min; Injection vol. 1 μL; Gradient $t_{=0}$=min 2% B, $t_{3.5\ min}$=98% B, $t_{6\ min}$=98% B, Post time 3 min, 2% B. Eluent A: 10 mM ammonium bicarbonate in water pH 9.5; Eluent B: 95% acetonitrile+5% 10 mM ammonium bicarbonate in water (pH 9.5);

HPLC Method Scan acid: Agilent system (1100 Binary Pump, G1312A, degasser; autosampler, ColCom, DAD detector: Agilent G1315B, 220-320 nm) Column: Waters XSelect™ CSH (50×2.1 mm 3.5 µm); Column temp 35° C.; Flow 0.8 mL/min; Injection vol. 1 µL; Gradient: $t_0$=2% B, $t_{3.5\ min}$=98% B, $t_{6\ min}$=98% B, Post time: 3 min.; Eluent A: 0.1% formic acid in water. Eluent B: 0.1% formic acid in acetonitrile.

HPLC Method Scan acid: Agilent system (1100 Binary Pump, G1312A, degasser; autosampler, ColCom, DAD detector: Agilent G1315B, 220-320 nm) Column: Phenomex Kinetex C18 100A (100*4.6 mm 2.6 µm); Column temp 35° C.; Flow 1.5 mL/min; Injection vol. 1 µL; Gradient: $t_0$=2% D, $t_{8\ min}$=98% D, $t_{11\ min}$=98% D, Post time: 3 min.; Eluent C: 0.1% formic acid in water. Eluent D: 0.1% formic acid in acetonitrile.

LC-MS Chromatograms
LC-MS Method Scan Base

Agilent 1100 Bin. Pump: G1312A, degasser; autosampler, ColCom, DAD: Agilent G1315B, 220-320 nm, MSD: Agilent LC/MSD G6130B ESI, pos/neg 100-800; column: Waters XSelect™ C18, 30×2.1 mm, 3.5µ, Temp: 25° C., Flow: 1 mL/min, Gradient: $t_0$=2% A, $t_{1.6\ min}$=98% A, $t_3\ min$=98% A, Post time: 1.3 min, Eluent A: 95% acetonitrile+5% 10 mM ammonium bicarbonate in water in acetonitrile, Eluent B: 10 mM ammonium bicarbonate in water (pH=9.5).

LC-MS Method Scan Acid

Apparatus: Agilent 1260 Bin. Pump: G1312B, degasser; autosampler, ColCom, DAD: Agilent G1315C, 220-320 nm, MSD: Agilent LC/MSD G6130B ESI, pos/neg 100-800, column: Waters XSelect™ CSH C18, 30×2.1 mm, 3.5µ, Temp: 35° C., Flow: 1 mL/min, Gradient: $t_0$=5% A, $t_{1.6\ min}$=98% A, $t_{3\ min}$=98% A, Post time: 1.3 min, Eluent A: 0.1% formic acid in acetonitrile, Eluent B: 0.1% formic acid in water HPLC—Method for the Determination of the Enantiomeric Purity
Identity (HPLC)

The difference between the retention time of the tested sample and the calibration solution of the compound of formula (I) must be below 5%.

Enantiomeric Purity
HPLC
Isocratic Chiral-Phase Method
Detection: UV-range
Column
  Length: 25 cm
  Inner diameter: 4.6 mm
  Filling: ChiralCel OZ-H (e.g. Fa.Daicel), 5 µm
Sample Solution Solvent
  0.5% ethanolamine in ethanol
  (e.g. mix of 5 mL ethanolamine in 1000 mL ethanol
Sample Solution
  Dissolve sample at a concentration of 1 mg/mL in 0.5% ethanolamine in ethanol.
Mobile Phase
  n-heptane/ethanol+ethanolamine (80/20; V:V+0.5%)
  (e.g. mix 800 mL n-heptane, 200 mL ethanol and 5 mL ethanolamine)
Flow Rate
  1.0 mL/min
Column Oven Temperature
  25° C.
Detection Wave Length
  280 nm
Injection Volume
  5 µL
Run Time of Chromatogram
  60 min
Evaluation/Calculation
  Integrate the peak areas of the enantiomers and evaluate according to 100% area method $$\% = \frac{A_1}{A_1 + A_2} \cdot 100\%$$

%=Enantiomeric purity of target compound (I) in percentage
A1=Peak area (R): target compound (I)
A2=Peak area (S): enantiomer of target compound (I)
  %=Enantiomeric purity of target compound (I) in percentage
  A1=Peak area (R): target compound (I)
  A2=Peak area(S): enantiomer of target compound (I)

UHPLC—Method for the Determination of the Chemical Purity and the Assay of the Compound of Formula (I)
Chemical Purity of Compound (I)
  Reversed-Phase UHPLC Method
Sum of All Org. Impurities
  Detection: UV-range
  External standard method (assay)
Column
  Length: 50 mm
  Inner diameter: 2.1 mm
  Filling: ZORBAX SB-AQ 1.8 µm, 80 Å, (e.g. Agilent Technologies, USA)
Sample Solution
  Dissolve sample at a concentration of 0.4 mg/mL in acetonitrile/water (9:1; V/V).
Calibration Solution
  Dissolve reference standard of the compound of formula (I) at a concentration of 0.4 mg/mL in acetonitrile/water (9:1; V/V).
Mobile Phase
  A Water+0.04% phosphoric acid ($H_3PO_4$) (85%)
  (e.g. 400 µL $H_3PO_4$/1 water) pH 2.4
  B Acetonitrile
Flow Rate
  0.6 mL/min
Column Oven temperature
  45° C.
Detection Wavelength
  210 nm
Injection Volume
  1.0 µL

| Gradient | | |
|---|---|---|
| time [min] | % A | % B |
| 0.0 | 95 | 5 |
| 1.0 | 95 | 5 |
| 15.0 | 50 | 50 |
| 17.0 | 20 | 80 |

-continued

| Run time of chromatogram |||
|---|---|---|
| 17 min |||
| Retention times |||
| compound | Approx. RT (min) | RRT |
| (I) | 6.0 | 1.00 |
| (VIb) | 0.5 | 0.08 |
| (IIIc) | 1.6 | 0.27 |
| 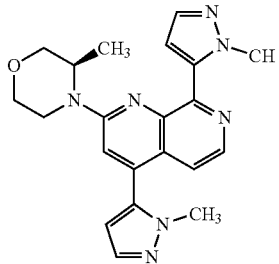 [SMILES: C[C@@H]1COCCN1c1cc(-c2ccnn2C)c2ccnc(-c3ccnn3C)c2n1] | 8.6 | 1.43 |
| (VIIc/VIId) | 9.6 | 1.60 |
| (IXb) | 10.2 | 1.70 |

Calculation of the Assay and the Purity of the Compound of Formula (I)

Assay: The peak areas of the sample solution are compared to those of the reference standard. Calculate the assay taking into account the weights of the reference standards using linear regression through zero with a validated chromatographic data system (e. g. Empower).

Purity: Impurities are evaluated according to the 100% area method. The purity in "area %" is calculated as the percentage of the HPLC peak area under the HPLC peak of polymorphic form B of the compound of formula (I) in relation to total peak area of all HPLC peaks UHPLC—Method for the Determination of N-Acetyl-Cysteine Assay
    Reversed-Phase UHPLC Method
    Detection: UV-range
    External standard method
Column
    Length: 100 mm
    Inner diameter: 3.0 mm
    Filling: YMC-Triart C18, 1.9 μm (e.g. YMC)
Sample Solution
    Dissolve sample at a concentration of 0.5 mg/mL in 0.1 n hydrochloric acid.
Calibration Solution
    Dissolve reference standard at a concentration of 0.00075 mg/mL (=in 0.15% of sample concentration) in 0.1 n hydrochloric acid.
Mobile Phase
    A. Water+ammonium dihydrogen phosphate+phosphoric acid ($H_3PO_4$) (85%)
    (e.g. 1.15 g ammonium dihydrogen phosphate+0.68 mL $H_3PO_4$/1 water) pH 2.4
    B. Acetonitrile
Flow Rate
    0.6 mL/min
Autosampler Temperature
    10° C.
Column Oven Temperature
    35° C.
Detection Wavelength
    195 nm
Injection Volume
    10 μL

| Gradient | time [min] | % A | % B |
|---|---|---|---|
| | 0.0 | 97 | 3 |
| | 2.5 | 97 | 3 |
| | 5.0 | 92 | 8 |
| | 6.0 | 20 | 80 |
| | 9.0 | 20 | 80 |
| Run time of chromatogram | 9 min | | |
| Retention times | | | |
| compound | | Approx. RT(min) | RRT |
| N-acetyl cysteine | | 2.84 | 1.00 |

Calculation of the Assay

Assay: The peak areas of the sample solution are compared to those of the reference standard. Calculate the assay taking into account the weights of the reference standards using linear regression through zero with a validated chromatographic data system (e. g. Empower).

GC—Method for the Determination of Pinacol

Procedure:
    Gas chromatograph with flame ionization (FID) and data evaluation system
Carrier Gas
    Hydrogen
Column Flow
    1.4 mL/min (const.)
Split Flow
    42 mL/min
Split Ratio
    30
Injector Temperature
    200° C.
Liner
    SGE Focus-Liner (P/N: 092219)
Capillary Column:
    Stationary phase: DB5-MS
    Length: approx.30 m
    Inner diameter: 0.25 mm
    Film thickness: 0.5 μm
Injection Volume
    1.0 μL
Temperature Program
    Start: 40° C. (2 min)
    Heating rate 1: 15° C./min
    to: 100° C. (2 min)
    Heating rate 2: 35° C./min
    to: 250° C. (2 min)
    Heating rate 3: 50° C./min
    to: 300° C. (4.7 min)
Total Run Time
    20 min
Detector Temperature
    325° C.
Combustion Gases
    Hydrogen 40 mL/min
    Synthetic Air 450 mL/min
    Nitrogen 30 mL/min Test Solution Dissolve the sample in acetonitrile in a concentration of 5 mg/mL (e. g. dissolve approx. 25 mg sample, accurately weighed, in 5.0 mL).

Control Solution

The control solution must be prepared like the test solution.

GC Conditions

The specified conditions are guide values. To achieve optimal separations they should, if necessary, be adapted to the technical possibilities of the chromatograph and the properties of the relevant column.

Procedure

Chromatograph test solution and control solution under the stated conditions.

The peaks in the chromatogram of the test solution must match the peaks of the control solution with regard to retention time on visual inspection.

| Name | RT [min] | RRT |
|---|---|---|
| Pinacol | 6.0 | — |
| Acetonitrile | 2.0 | — |

Evaluation

Electronic integration of the peak areas.

Assay Calculation

The peak area of the test solution is compared to that of the control solution. Calculate the assay taking into account the weights of the reference standards using linear regression 15 through zero with a validated chromatographic data system (e. g. Empower).

GC—method for the determination of 1-butanol, dichloromethane, ethyl acetate, isopropanol, methanol: GC-Headspace USP, version 41, chapter <467> "residual solvents"

Ion Chromatography (IC)—method for the determination of chloride, phosphate, sulfate: USP, version 41, chapter <1065> "ion chromatography"

ICP-MS—method for the determination of the sum of elements, boron, palladium, iron, potassium, sodium: USP, version 41, chapter <233> "elemental impurities", or Ph. Eur. ($9^{th}$ edition including supplements 9.1 to 9.5), chapter 2.2.58

Coulometric titration for the determination of water: Karl-Fischer, Coulometric titration Ph. Eur. ($9^{th}$ edition including supplements 9.1 to 9.5), chapter 2.5.32

X-Ray Powder Diffraction (XRPD):

XRPD analyses were performed using a "X'Pert Pro" diffractometer from PANalytical B.V., Netherlands, equipped with a Cu X-ray tube emitting (radiation Cu K alpha 1, wavelength 1.5406 Å). and a Pixcel detector system. The samples were analysed at 25° C. in transmission mode and held between low density polyethylene films. The HighScore Plus software, version 2.2c, from PANalytical B.V. was used applying the following parameters: range 3-40°2θ, step size 0.013°, counting time 99 sec, ~22 min run time. All X-ray reflections are quoted as °2θ (theta) values with a resolution of ±0.1°.

XRPD Reflections Listing (2θ Values) of Polymorphic Form B (=Mod B) of Compound of Formula (I)

TABLE A1

| Polymorphic Form B |
|---|
| 8.3 |
| 9.3 |

TABLE A1-continued

| Polymorphic Form B |
|---|
| 11.2 |
| 13.8 |
| 14.0 |
| 14.2 |
| 14.4 |
| 15.6 |
| 16.1 |
| 16.7 |
| 17.0 |
| 17.7 |
| 18.0 |
| 18.7 |
| 19.1 |
| 19.4 |
| 19.6 |
| 19.9 |
| 20.1 |
| 20.5 |
| 21.3 |
| 21.7 |
| 22.1 |
| 22.6 |
| 23.2 |
| 23.4 |
| 23.9 |
| 24.2 |
| 24.7 |
| 25.8 |
| 26.0 |
| 26.4 |
| 26.8 |
| 27.4 |
| 27.8 |
| 28.2 |
| 29.9 |
| 31.4 |
| 32.5 |
| 33.3 |
| 33.6 |
| 34.0 |
| 34.6 |
| 36.2 |
| 37.5 |
| 38.9 |
| 39.4 |

EXPERIMENTAL SECTION—EXAMPLES

Reactions were conducted under a nitrogen atmosphere unless stated otherwise.

Example 1a (R)-8-chloro-2-(3-methylmorpholino)-1,7-naphthyridin-4-yl trifluoromethanesulfonate (VIIIb)

To a mixture of (R)-8-chloro-2-(3-methylmorpholino)-1, 7-naphthyridin-4-ol (IIa) (20 g, 71.5 mmol) and triethylamine (19.88 mL, 143 mmol, 2 equiv.) in dichloromethane (100 mL) was added dropwise a solution of N-phenyl-bis(trifluoromethanesulfonimide) (25.5 g, 71.5 mmol, 1 equiv.) in dichloromethane (160 mL). The resulting reaction mixture was stirred at room temperature over night after which HPLC analysis of a sample indicated that all starting material had been consumed. The reaction mixture was poured into water (200 mL) and the resulting mixture was acidified with acetic acid (110 mL) until pH~3.5. after separation, the organic layer was stirred with aqueous acetic acid (100 ml, pH~3) for 5 min. The organic layer was separated, washed with water (200 mL) and then with 2M potassium carbonate (5×200 mL) until LCMS analysis of the organic layer indicated that all sulfonamide had been removed. Next, the organic layer was subsequently washed with water (200 mL) and brine (200 mL), dried over sodium sulfate, filtered and concentrated under reduced pressure. The residue (23 g) was recrystallized from hot 2-propanol (2 volumes, 46 mL). The next morning the solids were filtered off, rinsed with 2-propanol (5 mL) to give (R)-8-chloro-2-(3-methylmorpholino)-1,7-naphthyridin-4-yltrifluoromethane-sulfonate (VIIIb)). 18.91 g (64% th. yield) as a yellow solid.

$^1$H NMR (Chloroform-d) δ: 8.17 (d, J=5.5 Hz, 1H), 7.53 (d, J=5.5 Hz, 1H), 7.08 (s, 1H), 4.54-4.36 (m, 1H), 4.27 (d, J=12.0 Hz, 1H), 4.11 (dd, J=11.5, 3.8 Hz, 1H), 3.89 (d, J=11.5 Hz, 1H), 3.80 (dd, J=11.6, 3.1 Hz, 1H), 3.66 (td, J=12.0, 3.0 Hz, 1H), 3.42 (td, J=12.9, 3.9 Hz, 1H), 1.39 (d, J=6.8 Hz, 3H).

LC-MS (method: Scan base): Rt 2.33 min;
MS (ESI pos) m/z=412.1 [M+H]+.
HPLC (method: Scan base): Rt 3.88 min.

Example 1b (R)-4-(8-chloro-4-(1-methyl-1H-pyrazol-5-yl)-1,7-naphthyridin-2-yl)-3-methyl-morpholine (IXb)

To a solution of (R)-8-chloro-2-(3-methylmorpholino)-1,7-naphthyridin-4-yl trifluoro-methanesulfonate (VIIIb) (125.0 g, 304 mmol) in 300 mL degassed isopropyl acetate was added PdCl$_2$(dppf) (6.66 g, 9.1 mmol, 3 mol %). The mixture was heated to 50° C. after which a degassed solution of potassium hydrogen carbonate (122 g, 4 equiv.) in water (750 mL) at 50° C. was added to the reaction mixture. Immediately thereafter a solution of 1-methyl-1H-pyrazole-5-boronic acid pinacol ester (VIb) (63.2 g, 304 mmol, 1.0 equiv.) in 750 mL degassed isopropyl acetate was added over a period of 1.5 hours. After stirring for an additional hour at 50° C. complete conversion was observed in the HPLC analysis.

The reaction mixture was filtered over diatomaceous earth and the filter cake was rinsed with isopropyl acetate (300 mL). After this filtration the two layers were separated. The aqueous phase was extracted with isopropyl acetate (1×600 mL). The combined organic phases were washed with aqueous 1 N sodium hydroxide (4×600 mL) to remove traces of hydrolysed triflate (according to HPLC only ~1 area % was formed). The organic phase was subsequently washed with water (600 mL) and brine (600 mL) and dried over sodium sulfate. Forty minutes later activated charcoal (~10 g per 100 g starting material) was added and the resulting suspension was stirred overnight. The next morning the solids were filtered off over diatomaceous earth, the filter cake was rinsed with isopropyl acetate (200 mL) and the filtrate was concentrated to yield the crude (R)-4-(8-chloro-4-(1-methyl-1H-pyrazol-5-yl)-1,7-naphthyridin-2-yl)-3-methylmorpholine (intermediate (IXb)) as a brown foam (100.5 g, 96%). The crude product was purified by crystallization:

A 2 L round bottom flask was charged with crude (R)-4-(8-chloro-4-(1-methyl-1H-pyrazol-5-yl)-1,7-naphthyridin-2-yl)-3-methylmorpholine (IXb) (98 g, 268 mmol) and isopropanol (500 ml). Upon heating to 82° C. a clear brown solution was formed. Activated charcoal (10 g, 833 mmol) was added and the black suspension was stirred at 82° C. for 3 hours. The carbon was removed by filtration through diatomaceous earth using a preheated filtration setup. The filter was rinsed with 50 ml isopropanol and the filtrate was concentrated under reduced pressure to yield 92.87 g of a light brown solid. The filter used for removal of the activated charcoal was washed with DCM and the yellow filtrate was concentrated in vacuo. The material was redissolved in 400 ml isopropanol at 83° C. which gave a clear dark brown solution. Upon cooling a light brown solid precipitated. The suspension was stirred for 3 hours at room temperature. The solid material was collected by filtration and was washed on the filter with isopropanol (2×30 ml). After drying 72.5 g of purified (R)-4-(8-chloro-4-(1-methyl-1H-pyrazol-5-yl)-1,7-naphthyridin-2-yl)-3-methyl-morpholine (intermediate (IXb)) was collected (72.5 g, 79% th. yield).

The mother liquor still contained large amounts of the desired product and was concentrated in vacuo to yield 20.8 g of a brown solid.

$^1$H NMR (Chloroform-d) δ: 8.06 (d, J=5.5 Hz, 1H), 7.65 (d, J=1.9 Hz, 1H), 7.15 (d, J=5.4 Hz, 1H), 7.07 (s, 1H), 6.43 (d, J=1.9 Hz, 1H), 4.51 (dt, J=9.3, 4.5 Hz, 1H), 4.34 (dd, J=13.4, 2.8 Hz, 1H), 4.11 (dd, J=11.5, 3.8 Hz, 1H), 3.88 (d, J=11.4 Hz, 1H), 3.81 (dd, J=11.5, 3.2 Hz, 1H), 3.71 (s, 3H), 3.67 (td, J=11.8, 3.0 Hz, 1H), 3.42 (ddd, J=13.6, 12.4, 4.0 Hz, 1H), 1.40 (d, J=6.8 Hz, 3H).

LC-MS (method: Scan base): Rt 2.02 min; MS (ESI pos) m/z=344.2 [M+H]$^+$.

HPLC (method: Scan base): Rt 3.24 min.

Example 1c (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl)morpholine (VIIc/VIId)

A 100 mL three-neck round-bottom flask was charged with intermediate (IXb) (3.0 g, 8.73 mmol) and PdCl$_2$(dppf) (0.192 g, 0.262 mmol). Degassed ethyl acetate (12 mL) was added, followed by degassed water (6.0 mL) and anhydrous potassium phosphate (5.56 g, 26.2 mmol). The resulting two-phase reaction mixture was heated to 65° C., after which a solution of 1-(tetrahydro-2H-pyran-2-yl)-1H-pyrazole-5-boronic acid pinacol ester (IIIc) (2.91 g, 10.5 mmol) in degassed ethyl acetate (15 mL) was added dropwise to the reaction mixture over a period of 1 h (a syringe pump was used for the addition). An almost complete conversion was achieved directly after all boronic ester had been added. The reaction mixture was cooled down and concentrated to remove ethyl acetate. Dichloromethane (30 mL) was added, followed by water (30 mL, 10.0 volumes). The layers were separated and the organic phase was washed with a 2 M potassium carbonate solution (30 mL). Next, the organic phase was washed with water (4×30 mL), dried over sodium sulfate, filtered and concentrated. This afforded 4.16 g of crude (3R)-3-methyl-4-(4-(1-methyl-H-pyrazol-5-yl)-8-(1-(tetrahydro-2H-pyran-2-yl)-1H-pyrazol-5-yl)-1,7-naphthyridin-2-yl)morpholine (intermediate VIIc/VIId) as a brown solid.

According to ¹H-NMR the crude product consisted of a 1:1 mixture of diastereoisomers VIIc and VIId.

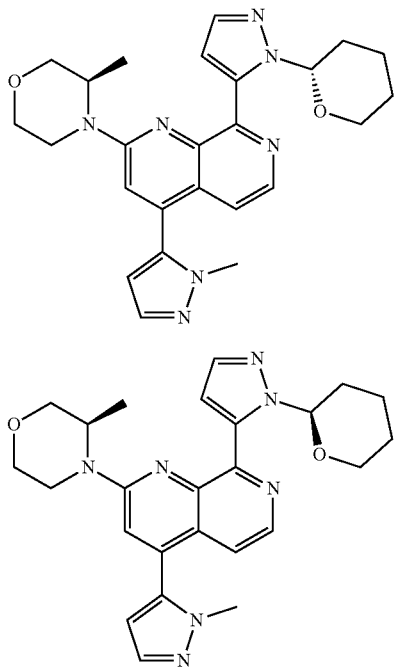

(VIIc)

(VIId)

¹H NMR (Chloroform-d) δ: 8.41 (dd, J=5.5, 2.2 Hz, 1H), 7.71 (d, J=1.8 Hz, 1H), 7.67 (d, J=1.9 Hz, 1H), 7.22 (dd, J=5.4, 1.4 Hz, 1H), 7.06 (d, J=3.8 Hz, 1H), 7.00 (dd, J=13.3, 1.8 Hz, 1H), 6.45 (t, J=1.7 Hz, 1H), 6.11 (dt, J=9.8, 2.7 Hz, 1H), 4.55-4.42 (m, 0.5H), 4.34 (dd, J=7.4, 2.7 Hz, 0.5H), 4.23 (dd, J=13.4, 2.8 Hz, 0.5H), 4.09-4.01 (m, 1.5H), 4.01-3.91 (m, 1H), 3.83 (dd, J=11.5, 5.7 Hz, 1H), 3.76 (s, 4H), 3.59 (tdd, J=11.5, 7.9, 2.9 Hz, 1H), 3.47 (tdd, J=11.1, 7.7, 2.5 Hz, 1H), 3.34 (dtd, J=21.7, 12.9, 3.9 Hz, 1H), 2.63-2.48 (m, 1H), 2.11 (td, J=12.9, 3.3 Hz, 2H), 1.81-1.58 (m, 3H), 1.35 (dd, J=6.8, 3.3 Hz, 3H).

LC-MS (method: Scan base): Rt 1.98 min;
MS (ESI pos) m/z=460.3 [M+H]⁺.
HPLC (method: Scan base): Rt 3.16 min.

The crude mixture of diastereoisomers VIIc and VIId was converted directly to the desired compound (I) (see Example 1d).

Example 1d

2-[(3R)-3-methylmorpholin-4-yl]-4-(1-methyl-1H-pyrazol-5-yl)-8-(1H-pyrazol-5-yl)-1,7-naphthyridine (I)

To a solution of crude intermediate (VIIc/VIId) (503 mg, 1.095 mmol) in a mixture of dichloromethane (1.50 mL) and methanol (0.15 mL) was added aqueous hydrochloric acid (1N, 1.50 mL, 1.5 mmol). The resulting dark brown biphasic mixture was stirred at room temperature for 30 minutes upon which HPLC analysis of both the organic and the aqueous phase indicated that complete conversion was achieved. The biphasic mixture was transferred into a separating funnel using aqueous hydrochloric acid (1N, 10 mL) and dichloromethane (10 ml). After vigorous shaking the aqueous layer was separated. The organic phase was further extracted with aqueous hydrochloric acid (1N, 10 mL). The combined aqueous phases were washed with dichloromethane (3×10 mL) and then poured out into 25 mL of 10% potassium carbonate which resulted in the formation of a blue-green suspension. The suspension was extracted with dichloromethane (4×10 ml). The combined organic layers were washed with brine, dried over sodium sulfate and concentrated under reduced pressure to yield 337 mg of bright yellow brittle foam. This material was taken up in dichloromethane (~8 mL), n-butanol (10 mL) was added and the resulting solution was concentrated under reduced pressure at 40° C. to remove the low boiling dichloromethane until approximately 6 mL of a greenish yellow solution was left in the flask. The remaining solution was stirred at room temperature overnight. The next morning, the crystallized product was filtered off using a glass filter, the bright yellow solid was washed with 1-butanol (3×2 mL) and dried on a stream of air to yield 203 mg of 2-[(3R)-3-methylmorpholin-4-yl]-4-(1-methyl-1H-pyrazol-5-yl)-8-(1H-pyrazol-5-yl)-1,7-naphthyridine (compound (1)) as a bright yellow (micro)-crystalline powder. Concentration of the filtrate yielded another 67 mg of compound (1) as a yellow-brown powder.

Yield: 203 mg+67 mg=270 mg (65.70% th. in total)
¹H NMR (Chloroform-d) δ: 12.81 (s, 1H, broad signal), 8.41 (d, J=5.5 Hz, 1H), 7.73 (d, J=1.9 Hz, 1H), 7.67 (d, J=1.9 Hz, 1H), 7.34 (d, J=1.8 Hz, 1H), 7.17 (t, J=2.7 Hz, 2H), 6.46 (d, J=1.9 Hz, 1H), 4.43 (tt, J=9.2, 4.4 Hz, 1H), 4.19 (dd, J=11.4, 3.9 Hz, 1H), 4.04 (dd, J=12.8, 2.8 Hz, 1H), 3.93 (d, J=11.6 Hz, 1H), 3.86 (dd, J=11.5, 3.1 Hz, 1H), 3.74 (s, 4H), 3.57 (td, J=12.4, 3.9 Hz, 1H), 1.47 (d, J=6.8 Hz, 3H).

LC-MS (method: Scan base): Rt 1.88 min;
MS (ESI pos) m/z=376.2 [M+H]⁺.
LC-MS (method: Scan acid): Rt 1.65 min;
MS (ESI pos) m/z=376.2 [M+H]⁺. HPLC (method: Scan acid): Rt 2.46 min. HPLC (method: An acid): Rt 3.41 min.

Example 1e (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl)morpholine (VIIc/VIId)

A 100 mL three-neck round-bottom flask was charged with intermediate (IXb) (3.0 g, 8.73 mmol) and PdCl₂(dppf) (0.192 g, 0.262 mmol). Degassed isopropyl acetate (12 mL) was added, followed by degassed water (6.0 mL) and anhydrous potassium phosphate (2.86 g, 17.5 mmol). The resulting two-phase reaction mixture was heated to 55° C., after which a solution of 1-(tetrahydro-2H-pyran-2-yl)-1H-pyrazole-5-boronic acid pinacol ester (IIIc) (2.91 g, 10.5 mmol) in degassed isopropyl acetate (15 mL) was added dropwise to the reaction mixture over a period of 1 h (a syringe pump was used for the addition). After completion of the addition the reaction mixture was continued to stir at 55° C. overnight (16 hours). The reaction mixture was subsequently cooled down to room temperature and filtered over a celite pad to remove interfacial material. The layers were separated and the organic phase was washed with a 2 M potassium carbonate solution (30 mL). Water (30 mL) was added to the organic phase and the layers were allowed to partition. Before complete separation of the two phases, the mixture was filtered over a celite pad to remove interfacial material. The organic phase was washed 3 more times with water (3×30 mL), dried over sodium sulfate, filtered and concentrated. This afforded 2.88 g of crude (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl)

morpholine (intermediate VIIc/VIId) as a brown solid. According to $^1$H-NMR the crude product consisted of a 1:1 mixture of diastereoisomers.

Example 2a (R)-8-chloro-2-(3-methylmorpholino)-1,7-naphthyridin-4-yl trifluoromethanesulfonate (VIIIb)

100 g (357.49 mmol) (R)-8-chloro-2-(3-methylmorpholino)-1,7-naphthyridin-4-ol (IIa) were suspended in 800 ml dichloromethane. At room temperature (~22° C.). Then 40.48 ml (500.485 mmol) pyridine was added and the mixture was cooled to −10° C. At −10° C. 84.2 ml (500.485) trifluoromethanesulfonic anhydride, dissolved in 250 ml dichloromethane was added to the mixture (30 min, temperature increase to −6° C.). After complete addition the mixture was stirred for 1 h at −10° C. 400 ml water were added slowly keeping the temperature between 0-4° C. The phases were separated. The organic phase washed with 400 ml water. The organic phase was washed two times with each 200 ml of an aqueous 0.5 M potassium carbonate solution and one time with 150 ml water. The organic phase was filtered through a charcoal filter and the filtrate was reduced to ~100 ml volume by distilling off dichloromethane at reduced pressure. 400 ml isopropanol was added and again distilled of at reduced pressure to ~100 ml volume (at 50° C.). This was done again. Finally 240 ml isopropanol was added and heated to 50° C. The mixture was stirred over weekend and was finally cooled to 0-3° C. The crystals were collected by filtration and washed with 100 ml isopropanol. The product was dried under vacuum (20 mbar) at 45° C. overnight. Yield: 113.87 g (77.35% th.) of yellow crystals.

HPLC: 100% (Area %) at 7.4 min.

Example 2b (R)-4-(8-chloro-4-(1-methyl-1H-pyrazol-5-yl)-1,7-naphthyridin-2-yl)-3-methyl-morpholine (IXb)

100 g (242.842 mmol) (R)-8-chloro-2-(3-methylmorpholino)-1,7-naphthyridin-4-yl trifluoro-methanesulfonate (VIIIb) and 5.3 g (7.285 mmol) PdCl$_2$(dppf) were dissolved in 400 ml ethyl acetate and were heated to 50° C. To this mixture a solution of 97.2 g (971.370 mmol) potassium hydrogen carbonate, dissolved in 600 ml water was added and the temperature was kept at 40° C. To this mixture a solution of 48.00 g (230.70 mmol) 1-methyl-1H-pyrazole-5-boronic acid pinacol ester (VIb), dissolved in 300 ml ethyl acetate was added over 3 h (at 40° C. inner temperature). The reaction mixture was cooled down to room temperature (+22° C.) and the phases were separated. The water phase was extracted with 300 ml ethyl acetate and the combined organic phases were washed two times with each 750 ml of an aqueous 1N potassium hydroxide solution and two times each with 500 ml water. To the last wash 10 ml of saline was added for a better phase separation. The organic phase was dried over 100 g sodium sulfate, filtered and the filter cake was washed with 200 ml ethyl acetate. Then 70 g of activated charcoal were added to the filtrate and the suspension was stirred 2 hours at room temperature. The charcoal was removed by filtration through diatomaceous earth (50 g) and the filter was washed with 100 ml ethyl acetate. A solvent switch was performed by adding isopropanol and distilling of ethyl acetate at 85° C. When a volume of ~200 ml isopropylacetate was reached (inner temperature 85° C.). It was cooled down to room temperature (by stirring overnight). The crystals were isolated by filtration were washed with 20 ml isopropanol. The product was dried under vacuum (20 mbar) at 45° C. overnight. Yield: 63.2 g (75.7% th.) of yellow crystals.

HPLC: 99.7% (Area %) at 11.9 min

Example 2c

2-[(3R)-3-methylmorpholin-4-yl]-4-(1-methyl-1H-pyrazol-5-yl)-8-(1H-pyrazol-5-yl)-1,7-naphthyridine (I)

120 g of crude (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl)morpholine (VIIc/VIId) dissolved in 480 ml dichloromethane and 480 ml methanol and cooled to 0-5° C. Then 1200 ml of an aqueous 1N hydrochloric acid solution was added and the temperature increased to 20° C. The mixture was stirred for 5 min at 20° C. and then the phases were separated, the water phase was extracted two times each with 480 ml dichloromethane. To the water phase 46.6 g N-acetyl cysteine was added and the solution was stirred at room temperature overnight. Then 960 ml dichloromethane were added and the mixture was cooled to 10° C. The pH was adjusted to pH=13 by adding 480 ml of an aqueous 5N potassium hydroxide solution. The solution was stirred for 30 min. The phases were separated and the water phase was extracted with 252 ml dichloromethane. The organic phases were combined and a solvent switch was performed from dichloromethane to n-butanol: to 631.5 ml n-butanol at 110° C. the filtrate was added slowly and dichloromethane was distilled off. The mixture was cooled down to 22° C. and was stirred overnight, then cooled down to 0-3° C. and stirred for 1 h at this temperature. The product was isolated by filtration and the crystals were washed twice with each 160 ml of cold n-butanol. The product was dried under vacuum (20 mbar) at 45° C. overnight. Yield: 62.87 g (64.13% th.) of yellow crystals.

HPLC: 99.48% (Area %) at 4.3 min.

Example 2d

2-[(3R)-3-methylmorpholin-4-yl]-4-(1-methyl-1H-pyrazol-5-yl)-8-(1H-pyrazol-5-yl)-1,7-naphthyridine (I)

Under nitrogen atmosphere 30 g (87.255 mmol) (R)-4-(8-chloro-4-(1-methyl-1H-pyrazol-5-yl)-1,7-naphthyridin-2-yl)-3-methyl-morpholine (IXb) were dissolved in 105.8 ml ethyl acetate and 1.91 g (2.618 mmol) PdCl$_2$(dppf) were added. Then 53.1 ml water and 55.56 g potassium phosphate were added. This mixture was stirred for 30 min at 22° C. The inner temperature was increased to 55° C. At 55° C. a solution of 31.55 g (113.43 mmol) 1-(tetrahydro-2H-pyran-2-yl)-1H-pyrazole-5-boronic acid pinacol ester (IIIc), dissolved in 162.2 ml ethyl acetate was added over 120 min keeping the temperature constant at 55° C. It was cooled to 35° C. and ethyl acetate was distilled off under vacuum (at 110 mbar, ~100 ml ethyl acetate). Then 164.4 ml dichloromethane and 255.6 ml water were added. The phases were separated and the water phase extracted with 84.5 ml dichloromethane. The combined organic phases were extracted twice with each 147 ml of an aqueous 1N potassium hydroxide solution. The phases were separated and the organic phase was treated with activated charcoal (21 g activated charcoal were added and the suspension was stirred overnight at 22° C.). The charcoal was removed by filtration through diatomaceous earth and the filter cake was washed with 40 ml dichloromethane. To the filtrate was added a mixture of 14.23 g N-acetyl cysteine and 7.8 g potassium hydroxide dissolved in 217.1 ml water (pH=9). The two phase mixture was stirred for 8 h at 20° C. The phases were separated and the organic phase was dried over 35.3 g sodium sulphate, which was then filtered and washed twice with each 35 ml dichloromethane. The solution was kept in the refrigerator and was used then for the next process step. To this solution (~350 ml) 160 ml methanol were added and the solution cooled to 0-5° C. Then 400 ml of an aqueous 1N hydrochloric acid solution was added and stirred for 30 min at room temperature. The phases were separated and the water phase was extracted twice with each 160 ml dichloromethane. To the water phase (pH=1) was added 14.2 g N-acetyl cysteine and the solution was stirred overnight at 20° C. Then 32 0 ml dichloromethane were added and the pH was adjusted to pH=13 by adding 160 ml of an aqueous 5N potassium hydroxide solution. The solution was stirred for 30 min. The phases were separated and water phase was washed with 84 ml dichloromethane. A solvent switch was performed from dichloromethane to n-butanol: to 212 ml n-butanol at 110° C. the filtrate was added slowly and dichloromethane was distilled off. The mixture was cooled down overnight to 22° C., then cooled down to 0-3° C. and stirred for 1 h at this temperature. The product was isolated by filtration and the crystals were washed with 20 ml of cold n-butanol. The product was dried under vacuum (20 mbar) at 45° C. overnight. Yield: 25.60 g (78.34% th.) of yellow crystals.

HPLC: 99.48% (Area %) at 4.3 min.

Example 2e

2-[(3R)-3-methylmorpholin-4-yl]-4-(1-methyl-1H-pyrazol-5-yl)-8-(1H-pyrazol-5-yl)-1,7-naphthyridine (I)

22.5 g (59.93 mmol) 2-[(3R)-3-methylmorpholin-4-yl]-4-(1-methyl-1H-pyrazol-5-yl)-8-(1H-pyrazol-5-yl)-1,7-naphthyridine (1) of example 2d were dissolved in 156.4 ml dichloromethane, 6.75 g of Quadrasil Mercaptopropyl (Pd scavenger from Johnson Matthey, CAS Number 1225327-73-0) and 6.75 g of Isolute Si-TMT (the silica bound equivalent of 2,4,6-trimercaptotriazine (TMT) Pd scavenger from Biotage AB, Sweden, Part No. 9538-1000) were added and the suspension was stirred 22 h at 20° C. The suspension was filtered and the filter cake was washed two times with each 46.8 ml dichloromethane. A solvent switch was performed from dichlormethane to n-butanol: to 85 ml n-butanol at 105° C. the filtrate was added slowly and dichloromethane was distilled off. Finally the temperature was increased to 105° C. (inner temperature) and then all dichloromethane was removed. The mixture was cooled down overnight to 22° C., then cooled down to 0-3° C. and stirred for 1 hour at this temperature. The product was isolated by filtration and the crystals were washed with 24 ml of cold n-butanol. The product was dried under vacuum (20 mbar) at 45° C. overnight. Yield: 19.50 g (86.67% th.) of yellow crystals.

HPLC: 99.97% (Area %)
Boron-content: <1 ppm
Palladium-content: <1 ppm
Polymorphic form of compound (I): B Example 3a (R)-8-chloro-2-(3-methylmorpholino)-1,7-naphthyridin-4-yl trifluoromethanesulfonate (VIIIb)

To a suspension of (R)-8-chloro-2-(3-methylmorpholino)-1,7-naphthyridin-4-ol (IIa) (100 g, qNMR-purity 90% weight based in dichloromethane (1.00 L) at room temperature was added triethylamine (63 mL, 450 mmol) which resulted in the formation of a clear brown solution. The reaction mixture was cooled to 0° C. (inner temperature) using an ice-salt bath. While stirring vigorously trifluoromethanesulfonic anhydride (0.076 L, 450 mmol) was added dropwise over a period of 10 min, which resulted in a 10° C. temperature increase. By the time the last amount of trifluoromethanesulfonic anhydride was added, the inner temperature decreased already. A sample (s1, taken 5 minutes after completion of trifluoromethanesulfonic anhydride addition) was analysed by HPLC indicating that almost complete conversion of the starting material had taken place. The ice-salt bath was removed and water (500 mL) was added. The resulting biphasic mixture was stirred vigorously for 1 minute. The aqueous phase was separated and the organic phase was washed further with water (2×500 mL) to remove all triethylamine and trifluoromethanesulfonic anhydride residues. Then the organic layer was washed with saturated aq. potassium carbonate (500 mL), dried over sodium sulfate, filtered and concentrated under reduced pressure until a volume of 250 mL. isopropanol (300 mL) was added and the mixture was further concentrated until a volume of ~300 mL (weighed 290 g of product solution). More isopropanol was added (100 mL, until an estimated 2 volumes) and the resulting mixture was left standing over night in order to crystallize the product.

The next morning a solid cake of crystalline material was formed. The solids were scratched loose with a spatula after which the mixture was stirred with a magnetic stirring bar to break larger lumps into smaller particles (2 hours). The solids were filtered off and dried over a stream of air to yield 110.3 g (83%) of (R)-8-chloro-2-(3-methylmorpholino)-1,7-naphthyridin-4-yl trifluoromethanesulfonate (intermediate (VIIIb)) as a dark yellow crystalline powder that still contained some larger lumps. HPLC purity 98 area %. The mother liquor was concentrated until 80 g of solution was left in the flask and a second portion of product could be isolated 6.26 g (4.7%).

Example 3b (R)-4-(8-chloro-4-(1-methyl-1H-pyrazol-5-yl)-1,7-naphthyridin-2-yl)-3-methyl-morpholine (IXb)

To a solution of (R)-8-chloro-2-(3-methylmorpholino)-1,7-naphthyridin-4-yl trifluoro-methanesulfonate (VIIIb) (125.0 g, 304 mmol) in 300 mL degassed isopropyl acetate was added $PdCl_2(dppf)$ (6.66 g, 9.1 mmol, 3 mol %). The mixture was heated to 50° C. after which a degassed solution of potassium hydrogen carbonate (122 g, 4 equiv.) in water (750 mL) at 50° C. was added to the reaction mixture. Immediately thereafter a solution of 1-methyl-1H-pyrazole-5-boronic acid pinacol ester (VIb) (63.2 g, 304 mmol, 1.0 equiv.) in 750 mL degassed isopropyl acetate was added over a period of 1.5 hours. After stirring for an additional hour at 50° C. complete conversion was observed in the HPLC analysis.

The reaction mixture was filtered over diatomaceous earth and the filter cake was rinsed with isopropyl acetate (300 mL). After this filtration the two layers were separated. The aqueous phase was extracted with isopropyl acetate (1*600 mL). The combined organic phases were washed with aqueous 1 N sodium hydroxide (4×600 mL) to remove traces of hydrolysed triflate (according to HPLC only ~1 area % was formed). The organic phase was subsequently washed with water (600 mL) and brine (600 mL) and dried over sodium sulfate. Forty minutes later activated charcoal (~10 g per 100 g starting material) was added and the resulting suspension was stirred overnight. The next morning the solids were filtered off over diatomaceous earth, the filter cake was rinsed with isopropyl acetate (200 mL) and the filtrate was concentrated to yield the crude (R)-4-(8-chloro-4-(1-methyl-1H-pyrazol-5-yl)-1,7-naphthyridin-2-yl)-3-methylmorpholine (IXb) as a brown foam (100.5 g, 96%).

Purification of Crude Intermediate (IXb)

A 2 L round bottom flask was charged with crude (R)-4-(8-chloro-4-(1-methyl-1H-pyrazol-5-yl)-1,7-naphthyridin-2-yl)-3-methylmorpholine (IXb) (98 g, 268 mmol) and isopropanol (500 ml). Upon heating to 82° C. a clear brown solution was formed. Activated charcoal (10 g, 833 mmol) was added and the black suspension was stirred at 82° C. for 3 hours. The carbon was removed by filtration through diatomaceous earth using a preheated filtration setup. The filter was rinsed with 50 ml isopropanol and the filtrate was concentrated under reduced pressure to yield 92.87 g of a light brown solid. The filter used for removal of the charcoal was washed with dichloromethane and the yellow filtrate was concentrated in vacuo. The material was redissolved in 400 ml isopropanol at 83° C. which gave a clear dark brown solution. Upon cooling a light brown solid precipitated. The suspension was stirred for 3 hours at room temperature. The solid material was collected by filtration and was washed on the filter with isopropanol (2×30 ml). After drying 72.5 g of purified (R)-4-(8-chloro-4-(1-methyl-1H-pyrazol-5-yl)-1,7-naphthyridin-2-yl)-3-methyl-morpholine (IXb) was collected (72.5 g, 79% yield). The mother liquor still contained large amounts of the desired product and was concentrated in vacuum to yield 20.8 g of a brown solid.

Example 4a (R)-8-chloro-2-(3-methylmorpholino)-1,7-naphthyridin-4-yl-trifluoromethanesulfonate (VIIIb)

3.00 kg (R)-8-chloro-2-(3-methylmorpholino)-1,7-naphthyridin-4-ol (IIa) were dissolved in 31.9 kg dichloromethane at 20. Then 1190 g pyridine was added. The solution was cooled to −10° C. (inner temperature) and a solution of 4.236 kg bis(trifluoro-methanesulfonic anhydride), dissolved in 10 kg dichloromethane was added, keeping the inner temperature at −10° C. The addition time was approximately 1 hour. After complete reaction 12.0 kg water was added, keeping the inner temperature at 0° C. to 15° C. After addition the mixture was stirred for 5 min. The organic phase was separated and washed with 12.0 kg water. The organic phase was washed 2 times with each 6 kg of an aqueous 0.5 N potassium carbonate solution and finally with 4.5 kg water. The organic phase was filtered over activated charcoal (Seitz charcoal filter plates) and the filtrate was distilled over to isopropanol (solvent switch). First dichloromethane was distilled under vacuum (100 mbar) to a concentrated solution (until it is stirrable), then 9.5 kg isopropanol were added and distilled (100 mbar) off (until it is stirrable). Another 9.5 kg isopropanol were added and distilled of (until it is stirrable), finally 1 kg isopropanol was added (in total ~8-9 kg isopropanol).

For crystallization the temperature was cooled down from 50° C. to 18° C. in 90 min (ramp). It was steered for 12 min at 18° C. and then cooled down to 0° C. (ramp, over 180 min). Then it was stirred for 60 min at 0° C. The crystals were isolated by filtration and washed with 2.4 kg cold isopropanol. The product was dried under vacuum at 45° C. for at least 12 h (until constant weight).

Four batches were prepared according to this protocol:

| (R)-8-chloro-2-(3-methylmorpholino)-1,7-naphthyridin-4-ol (II) Batch entry | (R)-8-chloro-2-(3-methylmorpholino)-1,7-naphthyridin-4-yl-trifluoromethanesulfonate (VIIIb) yield | Yield (% th.) |
|---|---|---|
| 3.00 kg | 3.139 kg | 71% |
| 3.00 kg | 3.264 kg | 74% |
| 3.00 kg | 2.987 kg | 68% |
| 3.00 kg | 3.291 kg | 74% |

Example 4b (R)-4-(8-chloro-4-(1-methyl-1H-pyrazol-5-yl)-1,7-naphthyridin-2-yl)-3-methyl-morpholine (IXb)

Under nitrogen 2.1 kg (R)-8-chloro-2-(3-methylmorpholino)-1,7-naphthyridin-4-yl-trifluoromethane-sulfonate (VIIIb) were dissolved in 8.4 liter ethyl acetate and 112 g $PdCl_2(dppf)$ were added. The solution was warmed up to 50° C. (inner temperature) and then 2.042 kg potassium hydrogen carbonate ($KHCO_3$), dissolved in 11.0 liter water was added, followed by 1.6 liter water (for cleaning the pipes). The inner temperature was put to 43° C. and then 1.061 kg 1-methyl-1H-pyrazole-5-boronic acid pinacol ester, dissolved in 6.0 liter ethyl acetate were added over 3 h, keeping the inner temperature at 43° C. After complete addition it was stirred for 75 min at 43° C.

Work-up: the mixture was cooled to 22° C. and the organic phase was separated (~15.4 l). The water phase was extracted with 6.3 liter ethyl acetate. The organic phases were combined and cooled to 10° C. and then washed with 15.75 liter of 5.3% aqueous potassium hydroxide solution (15 min stirring at 10). The phases were separated and the organic phase was washed again at 10° C. with 15.75 liter of 5.3% aqueous potassium hydroxide solution. After that the organic phase was separated and washed two times with each 10.5 liter water. To the organic phase 2.10 kg magnesium sulfate was added and stirred for 70 min at 22° C. Then magnesium sulfate is filtered off, washed two times with each 4.2 liter ethyl acetate. To the filtrate were added 1.47 active charcoal and the suspension was stirred for 2.5 h at 22° C. The charcoal was removed by filtration through diatomaceous earth and washed with ethyl acetate (twice, each 4.2 liter). 27.0 kg filtrate were obtained (product in ethyl acetate).

Five batches were prepared according to this protocol:

| Batch Entry | (R)-4-(8-chloro-4-(1-methyl-1H-pyrazol-5-yl)-1,7-naphthyridin-2-yl)-3-methyl-morpholine (IXb) in ethylacetate |
|---|---|
| 1 | 27.0 kg |
| 2 | 32.0 kg |
| 3 | 26.0 kg |
| 4 | 26.5 kg |
| 5 | 25.7 kg |

Crystallization from Isopropanol:

27.0 kg (entry 1) and 32.0 kg (entry 2) of (R)-4-(8-chloro-4-(1-methyl-1H-pyrazol-5-yl)-1,7-naphthyridin-2-yl)-3-methyl-morpholine (IXb) in ethyl acetate Total: 59.0 kg) were combined and a solvent switch to isopropanol was performed. Ethyl acetate was distilled of at normal pressure (inner temperature: 73° C. at the beginning 78° C. at the end). When 57.5 liter was distilled of 10.5 kg isopropanol were added and 13.5 liter were distilled off (at normal pressure, (inner temperature: 81° C. at the beginning 83° C. at the end). Another 10.5 kg isopropanol were added and 13.5 liter were distilled off (at normal pressure, (inner temperature: 80° C. at the beginning 83° C. at the end). Then another 10.5 kg isopropanol were added and 14.0 liter was distilled off (at normal pressure, (inner temperature: 82° C. at the beginning 84-85° C. at the end). The solution was cooled to 18° C. (ramp over 42 0 min). The suspension was stirred 1 h at 20° C. The product was isolated by filtration, washed with isopropanol (in total 2.4 kg). The product was dried under vacuum at 50° C. for at least 12 h (until constant weight). Yield: 2.69 kg (77% th.)

In a similar way batch entries 3 to 5 were combined (in total 78.2 kg) and the same solvent switch was performed yielding 4.042 kg (77% th.)

The following table summarizes the results:

| (R)-8-chloro-2-(3-methylmorpholino)-1,7-naphthyridin-4-yl-trifluoromethanesulfonate (VIIIb) | Batch Entry | (R)-4-(8-chloro-4-(1-methyl-1H-pyrazol-5-yl)-1,7-naphthyridin-2-yl)-3-methyl-morpholine (IXb) in ethylacetate | (R)-4-(8-chloro-4-(1-methyl-1H-pyrazol-5-yl)-1,7-naphthyridin-2-yl)-3-methyl-morpholine (IXb) |
|---|---|---|---|
| 4.2 kg | 1 | 27.0 kg | 2.69 kg |
|  | 2 | 32.0 kg | (77% th.) |
| 6.3 kg | 3 | 26.0 kg | 4.042 kg |
|  | 4 | 26.5 kg | (77% th.) |
|  | 5 | 25.7 kg |  |

The following table summarizes the analytical results of the two batches (2.69 kg batch IXb and 4.042 kg batch IXb):

| Test parameter | Acceptance criteria | Compound (IXb) (2.69 kg batch) | Compound (IXb) (4.042 kg batch) |
|---|---|---|---|
| Sulfate |  | <0.010% | <0.010% |
| Trifluoromethanesulfonic anhydride |  | 0.17% | 0.023% |
| Boric acid |  | <0.026% | <0.026% |
| Chloride |  | 0.053% | 0.035% |
| Total carbonate |  | <2 mg/L | <2 mg/L |
| Sum of elements (ICP) | % | 0.56 | 0.30 |
| Boron | mg/kg | <10 | <10 |
| Iron | mg/kg | 1400 | 760 |
| Potassium | mg/kg | <10 | <10 |
| Sodium | mg/kg | <10 | <10 |
| Paladium | mg/kg | 2700 | 1400 |
| Phosphorous | mg/kg | 1500 | 765 |
| Water |  | 0.0822% | 0.0511% |
| Dichloromethane |  | n.d. | n.d. |
| Ethyl acetate |  | n.d. | n.d. |
| Pyridine |  | n.d. | n.d. |
| 2-Propanol |  | 0.51154% | 0.25021% |
| Sum of all organic impurities | max. 1.0% | 0.5% | 0.3% |
| (VIb) |  | <0.05% (n.d.) | <0.05% (n.d.) |

| Test parameter | Acceptance criteria | Compound (IXb) (2.69 kg batch) | Compound (IXb) (4.042 kg batch) |
|---|---|---|---|
| (II) | | <0.05% (n.d.) | <0.05% (n.d.) |
| [structure] | max. 0.50% | 0.26% | 0.17% |
| (VIIIb) | | <0.05% | <0.05% (n.d.) |
| Impurities at RRT | | | |
| RRT 1.07 | max. 0.30% | <0.05% | <0.05% (n.d.) |
| RRT 0.93 | | n.d. | <0.05% |
| RRT 1.02 | | 0.05% | n.d. |
| RRT 1.04 | | <0.05% | n.d. |
| RRT 1.08 | | <0.05% | n.d. |
| RRT 1.12 | | 0.06% | 0.08% |
| RRT 1.15 | | 0.06% | n.d. |
| Purity (UHPLC) | | 99.5% | 99.7% |
| Assay (UHPLC) | | 96.5% | 97.9% |

Example 4c

2-[(3R)-3-methylmorpholin-4-yl]-4-(1-methyl-1H-pyrazol-5-yl)-8-(1H-pyrazol-5-yl)-1,7-naphthyridine (I)

Under nitrogen atmosphere 3.40 kg (R)-4-(8-chloro-4-(1-methyl-1H-pyrazol-5-yl)-1,7-naphthyridin-2-yl)-3-methyl-morpholine (IXb) were dissolved in 10.8 kg ethyl acetate and 221 g PdCl$_2$(dppf) were added. Then 6.0 kg water and 6.2 kg potassium phosphate were added. This mixture was stirred for 30 min at 22° C. The inner temperature was increased to 55° C. At 55° C. a solution of 3.8 kg 1-(tetrahydro-2H-pyran-2-yl)-1H-pyrazole-5-boronic acid pinacol ester (IIIc), dissolved in 16.4 kg ethyl acetate was added over 120 min keeping the temperature constant at 55° C. and the resulting mixture was stirred at 200 rpm. 2 kg ethyl acetate were added (used for washing the pipes). After addition the mixture is stirred for 10 min at 55° C.

For workup the temperature is decreased to 35° C. and 26.6 kg ethyl acetate is distilled off under vacuum. The mixture is cooled to 20° C. and 24.7 kg dichloromethane and 29.0 kg water were added. It was stirred for 10 min. The organic phase was separated and the water phase was extracted with 12.8 kg dichloromethane. The combined organic phases were washed with 17.7 kg of an aqueous 1N potassium hydroxide solution (stirring for 10 min). The phases were separated and the organic phase was washed again with 17.7 kg of an aqueous 1N potassium hydroxide solution (stirring for 10 min). The organic phase was separated and filtered over active charcoal (Seitz charcoal filter plates) for 3 h (running filtrate in circle). The charcoal was washed two times with each 13.3 kg dichloromethane, one time with 6.6 kg dichloromethane. The combined filtrates are added to a solution of 1.61 N-acetyl-cysteine in 9.0 kg aqueous potassium hydroxide solution (1099 g potassium hydroxide dissolved in 8.0 kg water). The mixture was stirred for 18 h at 20° C. The phases are separated. 35.72 kg of the organic phase were obtained.

In a similar way in total 3 batches, starting from 3.40 kg (R)-4-(8-chloro-4-(1-methyl-1H-pyrazol-5-yl)-1,7-naphthyridin-2-yl)-3-methyl-morpholine (IXb) were converted to (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl)morpholine (VIIc/VIId) in dichloromethane:

| Batch Entry | (R)-4-(8-chloro-4-(1-methyl-1H-pyrazol-5-yl)-1,7-naphthyridin-2-yl)-3-methyl-morpholine (IXb) | (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl)morpholine (VIIc/VIId) in dichloromethane |
|---|---|---|
| 1 | 3.4 kg | 37.52 kg |
| 2 | 3.4 kg | 34.70 kg |
| 3 | 3.4 kg | 33.56 kg |

The three batches were divided into 6 portions (two times half of each batch) and each batch was processed in the next reaction step.

The principal is described for a divided batch of 17.8 kg (VIIc/VIId) in dichloromethane. 17.8 kg of (VIIc/VIId) in dichloromethane was taken from a barrel and the barrel was washed with 800 g dichloromethane. Then 9 L dichloromethane were distilled off at normal pressure (60° C.). The solution was cooled to 22° C. and 3.3 kg dichloromethane and 7.2 kg methanol were added. The mixture was cooled to 0-5° C. and 16.8 kg of aqueous hydrochloric acid solution were added, keeping the temperature between 0-20° C. The mixture was stirred for 10 min at 20-22° C. Phases were separated and the water phase was extracted two times with each 8.8 kg dichloromethane. The water phase was separated and 800 g N-acetyl cysteine was added, the solution was stirred for 12 h at 20° C. Then 17.6 kg dichloromethane were added and 8246 g of an aqueous 5N potassium hydroxide solution were added and the mixture stirred for 30 min. The final pH of the aqueous phase was pH=13.6 (at this point the pH has to be 12-14). The phases were separated, the water phase extracted with 5.2 kg dichloromethane and the organic phases combined. 22.7 kg of compound (I) in dichloromethane were obtained.

The following table summarizes the result of 6 batches prepared in the described manner:

| Batch Entry | (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl)morpholine (VIIc/VIId) in dichloromethane | Batch splitting (VIIc/VIId) in dichloromethane Batch entry | Compound (I) in dichloromethane after cleavage of THP group |
|---|---|---|---|
| 1 | 37.52 kg | 1) 17.8 kg | 23.9 kg |
|   | Splitted in two batches 1&2 | 2) 17.8 kg | 23.6 kg |
| 2 | 34.70 kg | 3) 17.3 kg | 23.0 kg |
|   | Splitted in two batches 3&4 | 4) 17.3 kg | 24.0 kg |
| 3 | 33.56 kg | 5) 16.8 kg | 23.8 kg |
|   | Splitted in two batches 5&5 | 6) 16.7 kg | 22.7 kg |

For the next process step two times 3 batches of the previous prepared batches were combined and converted into the final product:

Solvent switch dichloromethane to n-butanol: 23.9 kg, 23.6 kg and 23.0 kg of compound (I) were combined (total 70.5 kg+5.0 kg for washing) and were slowly added to a 16.6 kg n-butanol which was preheated to 98° C. 59 liter dichloromethane were distilled off at normal pressure. The inner temperature during distillation was 81 to 90° C. Then 5.0 kg dichloromethane which was used to clean the pipes were also distilled off (5 liter). 15.5 kg n butanol were added and 10 l were distilled off at normal pressure (88 to 93° C.). The temperature was increased to 108° C. (inner temperature, 100 ml n-butanol distilled off). This is the point, where no dichloromethane is left. The solution is cooled to 20-22° C. (over 7 h (ramp)). The suspension is stirred for 1 h at 20° C., then cooled down to 2-3° C., stirred for 1 h at this temperature. The crystals were isolated by filtration and were washed with 8.0 kg cold n-butanol. The wet filter cake containing the product (1) was dissolved directly from the filter (without isolation) using 47.5 kg of 30° C. warm dichloromethane (in the case that this amount is not enough, more dichloromethane could be used and later distilled off). The solution was cooled to 20° C. and 1020 g of Quadrasil Mercaptopropyl (Pd scavenger from Johnson Matthey, CAS Number 1225327-73-0) and 1020 g of Isolute Si-TMT (the silica bound equivalent of 2,4,6-trimercaptotriazine (TMT), a Pd scavenger from Biotage AB, Sweden, Part No. 9538-1000) were added. The suspension was stirred for 12 h at 20-21° C. The suspension was filtered and the filter cake was washed two times with each 13.3 kg dichloromethane. The filtrate was filtered again (GMP particle filtration).

Final Crystallization Process

Solvent switch form dichloromethane to n-butanol: the filtrate of compound (I) was slowly added to a 16.5 kg n-butanol which was preheated to 98° C. 53 liter dichloromethane were distilled off at normal pressure. The inner temperature during distillation was 93 to 98° C. Then 5.0 kg dichloromethane which was used to clean the pipes were also distilled off (4 liter). 9.0 kg n-butanol was added and 10.5 l were distilled off at normal pressure (90 to 91° C.). The temperature was increased to 109° C. (inner temperature, 100 ml n-butanol distilled off). This is the point, where no dichloromethane is left. The solution is cooled to 20-22° C. (over 7 h (ramp)). The suspension is stirred for 1 h at 20, then cooled down to 2-30, stirred for 1 h at this temperature. The crystals were isolated by filtration and were washed with 8.0 kg cold n-butanol. The product was dried under vacuum (30 mbar) at 50° C. for at least 12 h (until constant weight).

3.753 kg (67% th.) of yellow crystals were obtained.

| Batch splitting (VIIc/VIId) in dichloromethane | Compound (I) in dichloromethane | Compound (I) in dichloromethane | Compound (I) |
|---|---|---|---|
| 1) 17.8 kg | 23.9 kg | 1 + 2 + 3: | 3.753 kg |
| 2) 17.8 kg | 23.6 kg | Total 70.5 kg |  |
| 3) 17.3 kg | 23.0 kg |  |  |
| 4) 17.3 kg | 24.0 kg | 4 + 5 + 6: | 4.066 kg |
| 5) 16.8 kg | 23.8 kg | Total 70.5 kg |  |
| 6) 16.7 kg | 22.7 kg |  |  |

Yield calculation: from 3 times 3.4 kg (IXb)=10.2 kg:7.819 kg of desired product (I) in 70.25% th. yield were obtained:

| Batch Entry | (R)-4-(8-chloro-4-(1-methyl-1H-pyrazol-5-yl)-1,7-naphthyridin-2-yl)-3-methyl-morpholine (IXb) | Compound (I): 2-[(3R)-3-methylmorpholin-4-yl]-4-(1-methyl-1H-pyrazol-5-yl)-8-(1H-pyrazol-5-yl)-1,7-naphthyridine |
|---|---|---|
| 1 | 3.4 kg | 3.753 kg + 4.066 kg = 7.819 kg (70.25% th.) |
| 2 | 3.4 kg |  |
| 3 | 3.4 kg |  |

Analytical Results:

| Test parameter | 3.753 kg Batch Compound (I) | 4.066 kg Batch Compound (I) |
|---|---|---|
| Material | solid | solid |
| Color | yellow | yellow |
| Identity (HPLC) | complies | complies |
| 1-butanol | 0.08565% | 0.09644% |
| Dichloromethane | n.n. | n.n. |
| Ethyl acetate | n.n. | n.n. |
| Isopropanol | n.n. | n.n. |
| Methanol | n.n | n.n. |
| n-Acetylcysteine | n.n. | n.n. |
| (IXb) | <0.05% | <0.05% |
| (VIb) | <0.05% | <0.05% |
| Dihydropyrane | <0.05% | <0.05% |
| (IIIc) | <0.05% | <0.05% |

-continued

| Test parameter | 3.753 kg Batch Compound (I) | 4.066 kg Batch Compound (I) |
|---|---|---|
| [structure of Compound (I)] | <0.05% | <0.05% |
| (VIIc/VIId) | <0.05% | <0.05% |
| Unspecified impurities | <0.05% | <0.05% |
| Sum of all organic impurities | 0.06% | 0.07% |
| Purity (UHPLC) | 99.94% | 99.93% |
| Assay (UHPLC) | 99.9% | 100.1% |
| Water | 0.045% | 0.050% |
| Polymorphic Modification (XRPD) | Polymorphic form B | Polymorphic form B |

Example 5

Pilot Plant Campaign

A pilot plant campaign was performed. Six batches (each 16.3 kg) were converted in the same way as described in example 4c (without cleaning the reactors and filter units during the campaign). In total 97.8 kg (IXb) were yielding 75.4 kg of desired compound (I)

| Entry batch (IXb) | Compound (I) | Yield (% th.) |
|---|---|---|
| 1) 16.3 kg | 10.4 kg | 58.5 |
| 2) 16.3 kg | 13.5 kg | 75.9 |
| 3) 16.3 kg | 11.6 kg | 65.2 |
| 4) 16.3 kg | 14.4 kg | 81.0 |
| 5) 16.3 kg | 12.1 kg | 68.0 |
| 6) 16.3 kg | 13.4 kg | 75.3 |

Average yield: 70.7% (th.)

The following table summarizes the analytical results:

| Test parameter | Entry 1 (10.4 kg) Compound (I) | Entry 2 (13.5 kg) Compound (I) | Entry 3 (11.6 kg) Compound (I) |
|---|---|---|---|
| 1-Butanol | 0.15226% | n.n. | 0.183% |
| Dichloromethane | 0.00644% | n.n. | n.n. |
| Ethyl acetate | n.n. | n.n. | n.n. |
| Isopropanol | n.n. | 0.12601% | n.n. |
| Methanol | n.n. | n.n. | n.n. |
| n-Acetylcysteine | n.n. | n.n. | n.n. |
| (IXb) | <0.05% | <0.05% | <0.05% |
| (VIb) | <0.05% | <0.05% | <0.05% |
| Dihydropyrane | <0.05% | <0.05% | <0.05% |
| (IIIc) | <0.05% | <0.05% | <0.05% |
| Pinacol | <0.05% | <0.05% | <0.05% |
| [structure of Compound (I)] | <0.05% | <0.05% | <0.05% |
| (VIIc/VIId) | <0.05% | <0.05% | <0.05% |
| Sum of all organic impurities | <0.05% | <0.05% | <0.05% |
| Purity | >99.95% | >99.95% | >99.95% |
| Assay | 99.9% | 100.0% | 100.0% |
| Water | 0.1008% | 0.0707% | 0.0902% |
| Polymorphic Modification | Polymorphic form B | Polymorphic form B | Polymorphic form B |
| Batch size | 10.40 kg | 13.50 kg | 14.40 kg |

| Test parameter | Entry 4 (14.40 kg) Compound (I) | Entry 5 (12.1 kg) Compound (I) | Entry 6 (13.4 kg) Compound (I) |
|---|---|---|---|
| 1-Butanol | 0.183% | 0.157% | 0.188% |
| Dichloromethane | n.n. | n.n. | n.n. |
| Ethyl acetate | n.n. | n.n. | n.n. |
| Isopropanol | n.n. | n.n. | n.n. |
| Methanol | n.n. | n.n. | n.n. |
| n-Acetylcystein | n.n. | n.n. | n.n. |
| (IXb) | <0.05% | <0.05% | <0.05% |

-continued

| | | | |
|---|---|---|---|
| (VIb) | <0.05% | <0.05% | <0.05% |
| Dihydropyrane | <0.05% | <0.05% | <0.05% |
| (IIIc) | <0.05% | <0.05% | <0.05% |
| Pinacol | <0.05% | <0.05% | <0.05% |
| 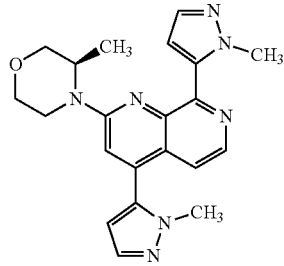 [SMILES: C[C@@H]1COCCN1c1cc(-c2ccnn2C)c2ccnc(-c3ccnn3C)c2n1] | <0.05% | <0.05% | <0.05% |
| (VIIc/VIId) | <0.05% | <0.05% | <0.05% |
| Sum of all organic impurities | <0.05% | <0.05% | <0.05% |
| Purity | >99.95% | >99.95% | >99.95% |
| Assay | 100.0% | 100.6% | 100.8% |
| Water | 0.0902% | 0.118% | 0.103% |
| Polymorphic Modification | Polymorphic form B | Polymorphic form B | Polymorphic form B |
| Batch size | 14.40 kg | 12.10 kg | 13.4 kg |

Two of those batches (entry 1 10.40 kg l and entry 2 13.50 kg l) were combined and analyzed.

The analytical data are shown in the following table:

| Test parameter (method) | Compound of formula (I) (23.322 kg) |
|---|---|
| Chloride (IC) | <0.010% |
| Sulfate (IC) | <0.010% |
| Phosphate (IC) | <0.010% |
| Sum of elements (ICP-MS) | |
| Boron (ICP-MS) | <10 mg/kg |
| Palladium (ICP-MS) | 0.3 mg/kg |
| Iron (ICP-MS) | <39 mg/kg |
| Potassium (ICP-MS) | <10 mg/kg |
| Sodium (ICP-MS) | <10 mg/kg |
| 1-Butanol (GC) | n.n. |
| Dichloromethane (GC) | n.n. |
| Ethyl acetate (GC) | n.n. |
| Isopropanol (GC) | <0.050% |
| Methanol (GC) | n.n. |
| n-Acetylcysteine (HPLC) | n.n. |
| (IXb) (UHPLC) | <0.05% |
| (VIb) (UHPLC) | <0.05% |
| Dihydropyrane (UHPLC) | <0.05% |
| (IIIc) (UHPLC) | <0.05% |
| Pinacol (GC) | <0.05% |
| 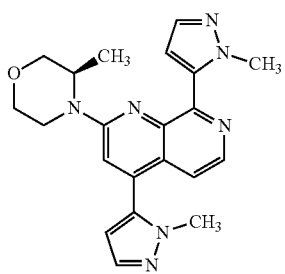 [SMILES: C[C@@H]1COCCN1c1cc(-c2ccnn2C)c2ccnc(-c3ccnn3C)c2n1] | <0.05% |
| (VIIc/VIId) (UHPLC) | <0.05% |
| Sum of all organic impurities (UHPLC) | <0.05% |
| Purity (UHPLC) | >99.95% |
| Enantiomeric purity (HPLC) | >99.85% |
| Assay (UHPLC) | 100.2% |

-continued

| Test parameter (method) | Compound of formula (I) (23.322 kg) |
|---|---|
| Water (Karl Fischer) | 0.163% |
| Polymorphic Modification (XRPD) | Polymorphic form B |
| Batch size | 23.322 kg |

Example 6

2-[(3R)-3-methylmorpholin-4-yl]-4-(1-methyl-1H-pyrazol-5-yl)-8-(1H-pyrazol-5-yl)-1,7-naphthyridine (I)

Under nitrogen atmosphere 30 g (87.255 mmol) (R)-4-(8-chloro-4-(1-methyl-1H-pyrazol-5-yl)-1,7-naphthyridin-2-yl)-3-methyl-morpholine (IXb) were dissolved in 105.8 ml ethyl acetate and 1.91 g (2.618 mmol) PdCl$_2$(dppf) were added. Then 53.1 ml water and 55.56 g potassium phosphate were added. This mixture was stirred for 30 min at 22° C. The inner temperature was increased to 55° C. At 55° C. a solution of 31.55 g (113.43 mmol) 1-(tetrahydro-2H-pyran-2-yl)-1H-pyrazole-5-boronic acid pinacol ester (IIIc), dissolved in 162.2 ml ethyl acetate was added over 120 min keeping the temperature constant at 55° C. It was cooled to room temperature (~22° C.) and 150 ml water was added. The phases were separated and the water phase extracted with 100 ml ethyl acetate. The combined organic phases were treated with activated charcoal (21 g activated charcoal were added and the suspension was stirred overnight at 22° C.). The charcoal was removed by filtration through diatomaceous earth and the filter cake was washed with 30 ml ethyl acetate. To the filtrate 100 ml methanol and 300 ml of an aqueous 1N hydrochloric acid solution was added and stirred for 30 min at room temperature. The phases were separated and the water phase extracted with 100 ml ethyl acetate. To the water phase (pH=1) was added 14.82 g N-acetyl cysteine and the solution was stirred overnight at 20° C. 300 ml dichloromethane were added and the pH was adjusted to pH=13 by adding 190 ml of an aqueous 5N potassium hydroxide solution. The solution was stirred for 30 min. The phases were separated and the organic phase was washed with 150 ml water. To the organic phase 6 g of Quadrasil Mercaptopropyl (Pd scavenger from Johnson Matthey, CAS Number 1225327-73-0) and 6 g of Isolute Si-TMT (the silica bound equivalent of 2,4,6-trimercaptotriazine (TMT) Pd scavenger from Biotage AB, Sweden, Part No. 9538-1000) were added and the suspension was stirred overnight at 20° C. The suspension was filtered and the filter cake was washed two times with each 25 ml dichloromethane. A solvent switch was performed from dichloromethane to n-butanol: to 60 ml n-butanol at 85° C. the filtrate was added slowly and dichloromethane was distilled off. Finally the temperature was increased to 105° C. (inner temperature) and then all dichloromethane was removed. The mixture was cooled down overnight to 22° C., then cooled down to 0-3° C. and stirred for 1 h at this temperature. The product was isolated by filtration and the crystals were washed with 20 ml of cold n-butanol. The product was dried under vacuum (20 mbar) at 45° C. overnight. Yield: 21.27 g (64.93% th.) of yellow crystals.

HPLC: 99.19% (Area %)

Boron-content: <1 ppm

Palladium-content: <1 ppm

Modification (Mod): B

The invention claimed is:

1. A method for preparing a compound of formula (I)

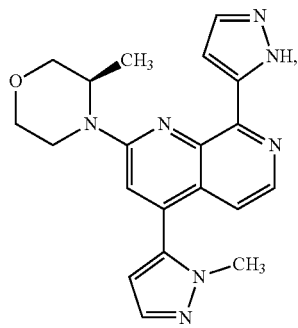

(I)

or its tautomer of formula (Ia)

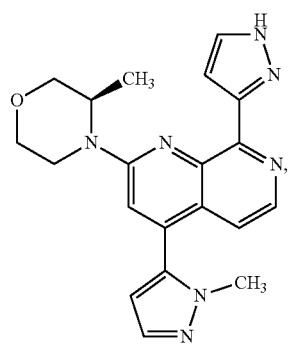

(Ia)

or a mixture thereof, said method comprising the successive steps of:

(a) reacting an intermediate compound of formula (IXa)

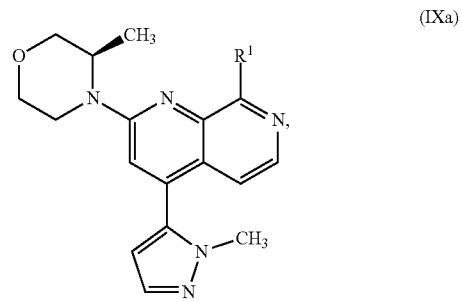

(IXa)

wherein $R^1$ is a chlorine, bromine or iodine atom or is a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy;

with a compound of formula (IIIa) or (IIIb)

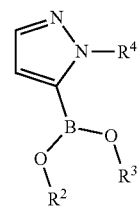

(IIIa)

or

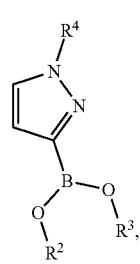

(IIIb)

or a mixture thereof, wherein $R^2$ and $R^3$ are independently a hydrogen atom or a $C_1$-$C_6$-alkyl group;

or $R^2$ and $R^3$ together represent a —$CH_2$—$CH_2$— group or a —$CH_2$—$CH_2$—$CH_2$— group, wherein said —$CH_2$—$CH_2$— group or —$CH_2$—$CH_2$—$CH_2$— group is optionally substituted one, two, three or four times with a group selected from methyl or ethyl; or R² and R³ together represent a group

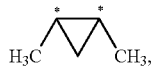

wherein "*" represents the point of attachment to the rest of the molecule; and

R⁴ is a group selected from the group consisting of tetrahydro-2H-pyran-2-yl, 1-methyl-1-methoxyethyl, 1-methyl-1-phenoxyethyl, and 1-methyl-1-benzyloxyethyl;

to give an intermediate compound of formula (VIIa) or (VIIb)

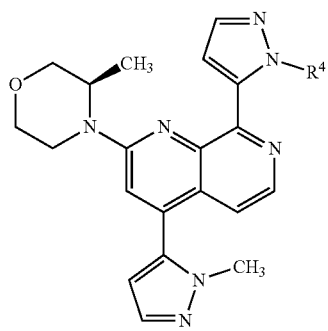

(VIIa)

or

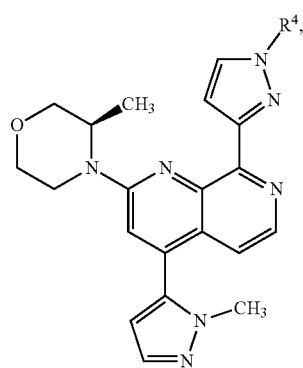

(VIIb)

or a mixture thereof; and (b) removing the group R⁴ from the intermediate compound of formula (VIIa) or (VIIb), thus providing a compound of formula (I), or its tautomer of formula (Ia), or a mixture thereof.

2. The method according to claim 1, wherein the compound of formula (IXa) is (R)-4-(8-chloro-4-(1-methyl-1H-pyrazol-5-yl)-1,7-naphthyridin-2-yl)-3-methyl-morpholine; and/or
wherein the compound of formula (IIIa) is 1-(tetrahydro-2H-pyran-2-yl)-1H-pyrazole-5-boronic acid pinacol ester; and/or wherein the compound of formula (VIIa) is (3R)-3-methyl-4-(4-(1-methyl-1H-pyrazol-5-yl)-8-(1-(tetrahydro-2H-pyran-2-yl)-1H-pyrazol-5-yl)-1,7-naphthyridin-2-yl) morpholine.

3. The method according to claim 1, wherein the reaction of the intermediate compound of formula (IXa) with a compound of formula (IIIa) or of formula (IIIb) is performed in the presence of a palladium catalyst and/or a base.

4. The method according to claim 1, wherein the reaction of the intermediate compound of formula (IXa) with a compound of formula (IIIa) or (IIIb) is performed in an organic solvent, wherein the solvent comprises isopropyl acetate, ethyl acetate, 1,2-dimethoxyethane, 1,4-dioxane, dimethylformamide, tetrahydrofuran, 2-methyltetrahydrofuran, methanol, ethanol, 1-propanol, isopropanol, 1-butanol or 2-butanol; or wherein said reaction is performed in a solvent mixture comprising one or more of said solvents and water.

5. The method according to claim 1, wherein the group R⁴ is removed from the intermediate compound of formula (VIIa) or (VIIb) by reacting the intermediate compound of formula (VIIa) or (VIIb) with an acid in a solvent or in a solvent mixture.

6. The method according to claim 1, wherein the intermediate compound of formula (VIIa) or (VIIb) is the compound of formula (VIIc), (VIId) or a mixture of (VIIc) and (VIId)

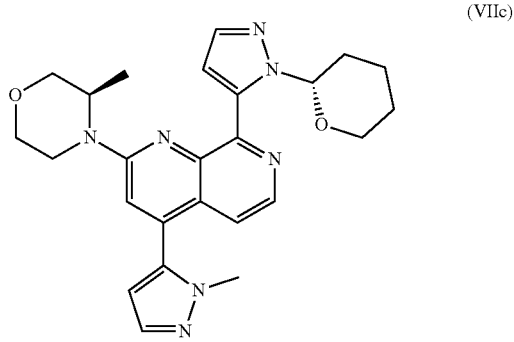

(VIIc)

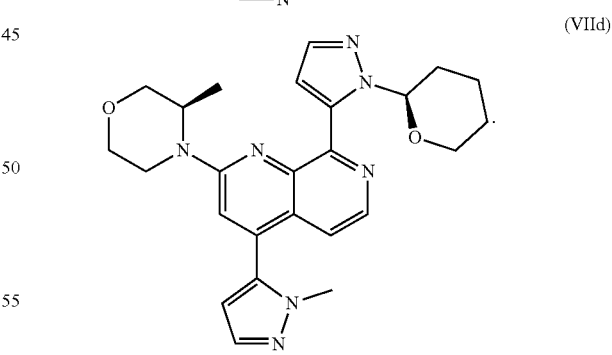

(VIId)

7. The method according to claim 1, wherein the intermediate compound of formula (VIIa) or (VIIb) is not isolated and/or is not purified prior to the step of removing the group R⁴ from the intermediate compound of formula (VIIa) or (VIIb).

8. The method according to claim 1, wherein the group R⁴ is removed from the intermediate compound of formula (VIIa) or (VIIb) by reacting the intermediate compound of formula (VIIa) or (VIIb) with aqueous hydrochloric acid in a solvent mixture comprising dichloromethane, methanol and water, to give the crude compound of formula (I) dissolved in an acidified aqueous phase, wherein the pH of the resulting acidified aqueous solution is less than 3 (pH<3).

9. The method according to claim 8, wherein
   (a) the acidified aqueous solution of the crude compound of formula (I) is extracted one or more times with solvent A, wherein solvent A comprises dichloromethane, ethyl acetate, isopropyl acetate, tetrahydrofuran, 2-methyl-tetrahydrofuran, toluol, or chloroform; and/or the acidified aqueous solution of the crude compound of formula (I) is treated one or more times with a Pd scavenger;
   (b) the acidified aqueous solution of the crude compound of formula (I) obtained by previous step (a) is treated with solvent A and with an aqueous solution of a base to give a two-phase system, wherein the aqueous phase of said two-phase system has a pH>12;
   (c) the aqueous phase with pH>12 obtained by step (b) is separated from the two-phase system to give a solution of the crude compound of formula (I) in solvent A; and, optionally,
   (d) replacing the solvent A of the solution of the crude compound of formula (I) in solvent A by solvent B, wherein solvent B comprises ethanol, n-propanol, n-butanol, 2-butanol, or isopropanol; to give a solution of the crude compound of formula (I) in solvent B.

10. The method according to claim 9, wherein solvent A comprises dichloromethane, and wherein the aqueous solution of a base comprises an aqueous solution of potassium hydroxide, and wherein solvent B comprises n-butanol.

11. The method according to claim 9, wherein the crude compound of formula (I) is crystallized in solvent B to give the polymorphic form B of the compound of formula (I).

12. The method according to claim 1, further comprising prior to step (a) according to claim 1 the step of
    (a) reacting an intermediate compound of formula (VIIIa)

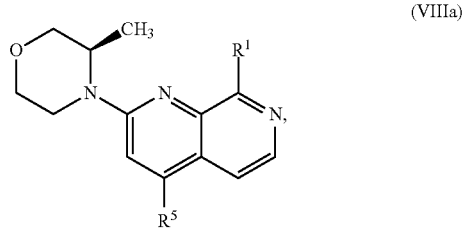

(VIIIa)

wherein
   $R^1$ is a chlorine, bromine or iodine atom or is a group selected from the group consisting of [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy; and
   $R^5$ is a chlorine, bromine or iodine atom or is a group selected from the group consisting of [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy;
with a compound of formula (VIa)

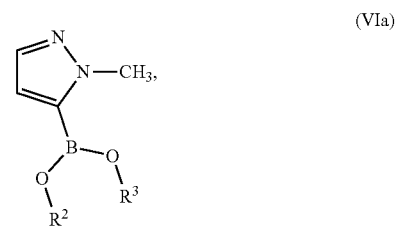

(VIa)

wherein
   $R^2$ and $R^3$ are independently a hydrogen atom or a $C_1$-$C_6$-alkyl group;
   or
   $R^2$ and $R^3$ together represent a —$CH_2$—$CH_2$— group or a —$CH_2$—$CH_2$—$CH_2$— group, wherein said —$CH_2$—$CH_2$— group or —$CH_2$—$CH_2$—$CH_2$— group is optionally substituted one, two, three or four times with a group selected from methyl and ethyl;
   or
   $R^2$ and $R^3$ together represent a group

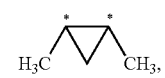

wherein "*" represents the point of attachment to the rest of the molecule;
to give an intermediate compound of formula (IXa)

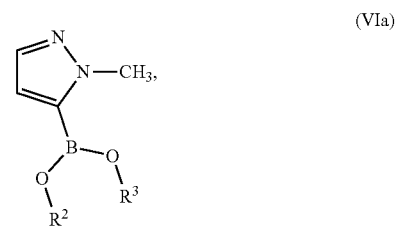

(IXa)

13. The method according to claim 12, wherein the compound of formula (VIIIa) is (R)-8-chloro-2-(3-methylmorpholino)-1,7-naphthyridin-4-yl trifluoro-methanesulfonate; and/or wherein the compound of formula (VIa) is 1-methyl-1H-pyrazole-5-boronic acid pinacol ester.

14. The method according to claim 12, wherein the reaction of the intermediate compound of formula (VIIIa) with a compound of formula (VIa) is performed in the presence of a palladium catalyst and/or a base.

15. The method according to claim 12, further comprising—prior to step (a) according to claim 12—the step of reacting an intermediate compound of formula (II)

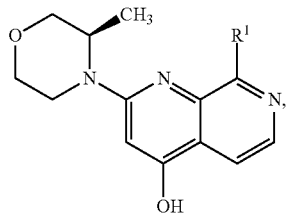

(II)

wherein $R^1$ is a chlorine, bromine or iodine atom or is a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy or [(4-methoxyphenyl)sulfonyl]oxy;

with a compound selected from N-phenyl-bis (trifluoromethanesulfonimide, trifluoromethanesulfonic anhydride, methanesulfonic acid chloride, p-toluenesulfonyl chloride, nonafluorobutanesulfonyl chloride, nonafluorobutanesulfonyl fluoride, benzenesulfonyl chloride, 4-bromobenzenesulfonyl chloride, 4-nitrobenzenesulfonyl chloride, 2-nitrobenzenesulfonyl chloride, 4-isopropylbenzenesulfonyl chloride, 2,4,6-triisopropylbenzenesulfonyl chloride, 2-mesitylenesulfonyl chloride (=2,4,6-trimethylbenzenesulfonyl chloride), 4-tert-butylbenzenesulfonyl chloride or 4-methoxybenzenesulfonyl chloride;

to give an intermediate compound of formula (VIIIa)

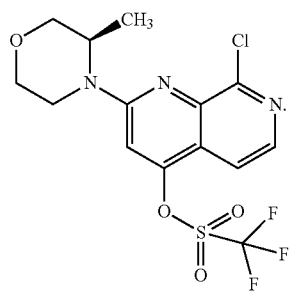

(VIIIa)

$R^5$ is a chlorine, bromine or iodine atom or is a group selected from [(trifluoromethyl)sulfonyl]oxy, [(nonafluorobutyl)sulfonyl]oxy, (methylsulfonyl)oxy, (p-toluenesulfonyl)oxy, (phenylsulfonyl)oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy or [(4-methoxyphenyl)sulfonyl]oxy.

16. The method according to claim 15, wherein the compound of formula (II) is (R)-8-chloro-2-(3-methylmorpholino)-1,7-naphthyridin-4-ol, which is reacted with trifluoromethanesulfonic anhydride to give an intermediate compound of formula (VIIIb)

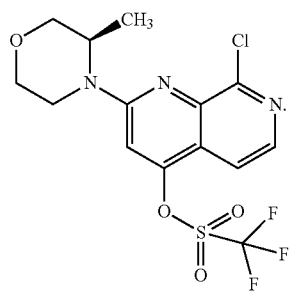

(VIIIb)

* * * * *